(12) United States Patent
Phadke et al.

(10) Patent No.: US 11,814,363 B2
(45) Date of Patent: Nov. 14, 2023

(54) MORPHIC FORMS OF DANICOPAN

(71) Applicant: Achillion Pharmaceuticals, Inc., Blue Bell, PA (US)

(72) Inventors: Avinash Phadke, Branford, CT (US); Akihiro Hashimoto, Branford, CT (US); Wei Ma, Cary, NC (US); Lee M. Katrincic, Durham, NC (US)

(73) Assignee: Achillion Pharmaceuticals, Inc., Boston, MA (US)

( * ) Notice: Subject to any disclaimer, the term of this patent is extended or adjusted under 35 U.S.C. 154(b) by 78 days.

(21) Appl. No.: 17/272,924

(22) PCT Filed: Sep. 6, 2019

(86) PCT No.: PCT/US2019/050073
§ 371 (c)(1),
(2) Date: Mar. 2, 2021

(87) PCT Pub. No.: WO2020/051538
PCT Pub. Date: Mar. 12, 2020

(65) Prior Publication Data
US 2023/0094124 A1    Mar. 30, 2023

Related U.S. Application Data

(60) Provisional application No. 62/727,954, filed on Sep. 6, 2018.

(51) Int. Cl.
*C07D 401/14*    (2006.01)
(52) U.S. Cl.
CPC ........ *C07D 401/14* (2013.01); *C07B 2200/13* (2013.01)

(58) Field of Classification Search
CPC ............. C07D 401/14; C07B 2200/13; A61K 31/506; A61K 45/06; A61P 21/00; A61P 27/02; A61P 29/00; A61P 37/00
See application file for complete search history.

(56) References Cited

U.S. PATENT DOCUMENTS

| | | |
|---|---|---|
| 5,628,984 A | 5/1997 | Boucher, Jr. |
| 6,319,897 B1 | 11/2001 | Lambris et al. |
| 6,489,476 B1 | 12/2002 | Dang et al. |
| 6,492,402 B1 | 12/2002 | Lee et al. |
| 6,653,340 B1 | 11/2003 | Babu et al. |
| 7,482,376 B2 | 1/2009 | Subasinghe et al. |
| 7,629,340 B2 | 12/2009 | Schmitz et al. |

(Continued)

FOREIGN PATENT DOCUMENTS

| | | |
|---|---|---|
| CN | 103402996 A | 11/2013 |
| EA | 201890594 A1 | 8/2018 |

(Continued)

OTHER PUBLICATIONS

U.S. Appl. No. 16/006,476, Wiles et al.
(Continued)

*Primary Examiner* — Joseph K McKane
*Assistant Examiner* — David M Shim
(74) *Attorney, Agent, or Firm* — Clark & Elbing LLP

(57) ABSTRACT

This invention provides stable, highly crystalline forms of Complement factor D inhibitors Compound 1 for advantageous therapeutic pharmaceutical efficacy and dosage form stability.

15 Claims, 24 Drawing Sheets

(56) References Cited

U.S. PATENT DOCUMENTS

| | | | |
|---|---|---|---|
| 7,888,323 B2 | 2/2011 | Lambris et al. | |
| 7,989,589 B2 | 8/2011 | Lambris | |
| 7,999,081 B2 | 8/2011 | Tedesco et al. | |
| 8,168,584 B2 | 5/2012 | Deschatelets et al. | |
| 8,241,628 B2 | 8/2012 | Diefenbach-Streiber et al. | |
| 8,524,716 B2 | 9/2013 | Raboisson et al. | |
| 8,580,735 B2 | 11/2013 | Francois et al. | |
| 8,883,158 B2 | 11/2014 | Diefenbach-Streiber et al. | |
| 8,946,145 B2 | 2/2015 | Lambris et al. | |
| 9,056,076 B2 | 6/2015 | Deschatelets et al. | |
| 9,085,555 B2 | 7/2015 | Altmann et al. | |
| 9,169,307 B2 | 10/2015 | Lambris et al. | |
| 9,291,622 B2 | 3/2016 | Zhang et al. | |
| 9,371,365 B2 | 6/2016 | Lambris et al. | |
| 9,421,240 B2 | 8/2016 | Francois et al. | |
| 9,468,661 B2 | 10/2016 | Altmann et al. | |
| 9,598,446 B2 | 3/2017 | Gadhachanda et al. | |
| 9,643,986 B2 | 5/2017 | Wiles et al. | |
| 9,663,543 B2 | 5/2017 | Wiles et al. | |
| 9,695,205 B2 | 7/2017 | Wiles et al. | |
| 9,732,103 B2 | 8/2017 | Wiles et al. | |
| 9,732,104 B2 | 8/2017 | Gadhachanda et al. | |
| 9,758,537 B2 | 9/2017 | Wiles et al. | |
| 9,796,741 B2 * | 10/2017 | Gadhachanda | C07D 403/14 |
| 9,828,396 B2 | 11/2017 | Wiles et al. | |
| 9,851,351 B2 | 12/2017 | Reich et al. | |
| 10,000,516 B2 | 6/2018 | Wiles et al. | |
| 10,005,802 B2 | 6/2018 | Wiles et al. | |
| 10,011,612 B2 | 7/2018 | Wiles et al. | |
| 10,081,645 B2 | 9/2018 | Wiles et al. | |
| 10,087,203 B2 | 10/2018 | Wiles et al. | |
| 10,092,547 B2 | 10/2018 | Wiles et al. | |
| 10,092,584 B2 | 10/2018 | Wiles et al. | |
| 10,100,072 B2 | 10/2018 | Wiles et al. | |
| 10,106,563 B2 | 10/2018 | Wiles et al. | |
| 10,138,225 B2 | 11/2018 | Wiles et al. | |
| 10,189,869 B2 | 1/2019 | Gadhachanda et al. | |
| 10,253,053 B2 | 4/2019 | Wiles et al. | |
| 10,287,301 B2 | 5/2019 | Wiles et al. | |
| 10,301,336 B2 | 5/2019 | Wiles et al. | |
| 10,370,394 B2 | 8/2019 | Wiles et al. | |
| 10,385,097 B2 | 8/2019 | Wiles et al. | |
| 10,428,094 B2 | 10/2019 | Wiles et al. | |
| 10,428,095 B2 | 10/2019 | Wiles et al. | |
| 10,464,956 B2 | 11/2019 | Wiles et al. | |
| 10,550,140 B2 | 2/2020 | Wiles et al. | |
| 10,660,876 B2 | 5/2020 | Wiles et al. | |
| 10,662,175 B2 | 5/2020 | Wiles et al. | |
| 10,807,952 B2 | 10/2020 | Wiles et al. | |
| 10,822,352 B2 | 11/2020 | Wiles et al. | |
| 10,906,887 B2 | 2/2021 | Wiles et al. | |
| 10,919,884 B2 | 2/2021 | Wiles et al. | |
| 11,001,600 B2 | 5/2021 | Wiles et al. | |
| 11,053,253 B2 | 7/2021 | Wiles et al. | |
| 11,084,800 B2 | 8/2021 | Wiles et al. | |
| 11,407,738 B2 | 8/2022 | Wiles et al. | |
| 11,447,465 B2 | 9/2022 | Wiles et al. | |
| 2002/0133004 A1 | 9/2002 | Sekiyama et al. | |
| 2005/0228000 A1 | 10/2005 | Smallheer et al. | |
| 2005/0245497 A1 | 11/2005 | Penfold et al. | |
| 2005/0267108 A1 | 12/2005 | Hsieh et al. | |
| 2006/0004000 A1 | 1/2006 | D'Orchymont et al. | |
| 2007/0155712 A1 | 7/2007 | Zahn et al. | |
| 2008/0075720 A1 | 3/2008 | Holers et al. | |
| 2008/0075728 A1 | 3/2008 | Newman | |
| 2008/0108691 A1 | 5/2008 | Hamann et al. | |
| 2009/0162358 A1 | 6/2009 | Alard et al. | |
| 2010/0041628 A1 | 2/2010 | Enomoto et al. | |
| 2011/0280808 A1 | 11/2011 | Kroth et al. | |
| 2012/0231471 A1 | 9/2012 | Sato et al. | |
| 2012/0237515 A1 | 9/2012 | Bell et al. | |
| 2012/0295884 A1 | 11/2012 | Altmann et al. | |
| 2013/0029912 A1 | 1/2013 | Holers et al. | |
| 2013/0035392 A1 | 2/2013 | McGeer et al. | |
| 2013/0296377 A1 | 11/2013 | Adams et al. | |
| 2013/0324482 A1 | 12/2013 | Francois et al. | |
| 2013/0344073 A1 | 12/2013 | Schwaeble et al. | |
| 2014/0050739 A1 | 2/2014 | Francois et al. | |
| 2014/0323407 A1 | 10/2014 | Francois et al. | |
| 2014/0371133 A1 | 12/2014 | Francois et al. | |
| 2015/0141455 A1 | 5/2015 | Altmann et al. | |
| 2015/0148374 A1 | 5/2015 | Hommel et al. | |
| 2015/0158915 A1 | 6/2015 | Lambris et al. | |
| 2015/0191462 A1 | 7/2015 | Hommel et al. | |
| 2015/0239837 A1 | 8/2015 | Wiles et al. | |
| 2015/0239838 A1 | 8/2015 | Phadke et al. | |
| 2015/0239868 A1 | 8/2015 | Pais et al. | |
| 2015/0239893 A1 | 8/2015 | Wang et al. | |
| 2015/0239894 A1 | 8/2015 | Gadhachanda et al. | |
| 2015/0239895 A1 | 8/2015 | Gadhachanda et al. | |
| 2015/0239919 A1 | 8/2015 | Gadhachanda et al. | |
| 2015/0239920 A1 | 8/2015 | Gadhachanda et al. | |
| 2015/0239921 A1 | 8/2015 | Wiles et al. | |
| 2015/0322060 A1 | 11/2015 | Flohr et al. | |
| 2015/0368271 A1 | 12/2015 | Su et al. | |
| 2016/0015810 A1 | 1/2016 | Deschatelets et al. | |
| 2016/0024079 A1 | 1/2016 | Adams et al. | |
| 2016/0060297 A1 | 3/2016 | Deschatelets et al. | |
| 2016/0194359 A1 | 7/2016 | Francois et al. | |
| 2016/0215020 A1 | 7/2016 | Francois et al. | |
| 2016/0215022 A1 | 7/2016 | Francois et al. | |
| 2016/0361329 A1 | 12/2016 | Wiles et al. | |
| 2016/0362398 A1 | 12/2016 | Wiles et al. | |
| 2016/0362399 A1 | 12/2016 | Wiles et al. | |
| 2016/0362432 A1 | 12/2016 | Wiles et al. | |
| 2016/0362433 A1 | 12/2016 | Wiles et al. | |
| 2017/0056428 A1 | 3/2017 | Wiles et al. | |
| 2017/0057950 A1 | 3/2017 | Wiles et al. | |
| 2017/0057983 A1 | 3/2017 | Wiles et al. | |
| 2017/0057993 A1 | 3/2017 | Wiles et al. | |
| 2017/0066783 A1 | 3/2017 | Wiles et al. | |
| 2017/0189410 A1 | 7/2017 | Gadhachanda et al. | |
| 2017/0202821 A1 | 7/2017 | Bekker | |
| 2017/0202935 A1 | 7/2017 | Lambris et al. | |
| 2017/0226142 A1 | 8/2017 | Wiles et al. | |
| 2017/0260219 A1 | 9/2017 | Wiles et al. | |
| 2017/0298084 A1 | 10/2017 | Wiles et al. | |
| 2017/0298085 A1 | 10/2017 | Wiles et al. | |
| 2018/0022766 A1 | 1/2018 | Wiles et al. | |
| 2018/0022767 A1 | 1/2018 | Wiles et al. | |
| 2018/0030075 A1 | 2/2018 | Wiles et al. | |
| 2018/0072762 A1 | 3/2018 | Wiles et al. | |
| 2018/0177761 A1 | 6/2018 | Wiles et al. | |
| 2018/0179185 A1 | 6/2018 | Wiles et al. | |
| 2018/0179186 A1 | 6/2018 | Wiles et al. | |
| 2018/0179236 A1 | 6/2018 | Wiles et al. | |
| 2018/0186782 A1 | 7/2018 | Wiles et al. | |
| 2018/0201580 A1 | 7/2018 | Wiles et al. | |
| 2018/0305375 A1 | 10/2018 | Wiles et al. | |
| 2019/0023729 A1 | 1/2019 | Wiles et al. | |
| 2019/0031692 A1 | 1/2019 | Wiles et al. | |
| 2019/0038623 A1 | 2/2019 | Huang et al. | |
| 2019/0048033 A1 | 2/2019 | Wiles et al. | |
| 2019/0085005 A1 | 3/2019 | Wiles et al. | |
| 2019/0144473 A1 | 5/2019 | Gadhachanda et al. | |
| 2019/0151334 A1 | 5/2019 | Bosworth et al. | |
| 2019/0211033 A1 | 7/2019 | Wiles et al. | |
| 2019/0359645 A1 | 11/2019 | Birkus et al. | |
| 2019/0382376 A1 | 12/2019 | Wiles et al. | |
| 2020/0002347 A1 | 1/2020 | Wiles et al. | |
| 2020/0062790 A1 | 2/2020 | Wiles et al. | |
| 2020/0071301 A1 | 3/2020 | Wiles et al. | |
| 2020/0101071 A1 | 4/2020 | Huang et al. | |
| 2020/0262818 A1 | 8/2020 | Wiles et al. | |
| 2021/0332026 A1 | 10/2021 | Phadke et al. | |
| 2022/0079943 A1 | 3/2022 | Huang et al. | |

FOREIGN PATENT DOCUMENTS

| | | |
|---|---|---|
| JP | 2014-506877 A | 3/2014 |
| JP | 2015-522005 A | 8/2015 |
| JP | 2015-522006 A | 8/2015 |
| JP | 2015-522007 A | 8/2015 |
| JP | 2015-522008 A | 8/2015 |

(56) References Cited

FOREIGN PATENT DOCUMENTS

| | | |
|---|---|---|
| JP | 2015-522062 A | 8/2015 |
| JP | 2017-511815 A | 4/2017 |
| JP | 6400738 B2 | 10/2018 |
| JP | 2018-199714 A | 12/2018 |
| JP | 6537532 B2 | 7/2019 |
| JP | 6688352 B2 | 4/2020 |
| JP | 6877406 B2 | 5/2021 |
| RU | 2202344 C2 | 4/2003 |
| RU | 2470918 C2 | 12/2012 |
| WO | WO-93/20099 A2 | 10/1993 |
| WO | WO-95/29697 A1 | 11/1995 |
| WO | WO-99/48492 A1 | 9/1999 |
| WO | WO-2004/007501 A1 | 1/2004 |
| WO | WO-2004/045518 A2 | 6/2004 |
| WO | WO-2004/111041 A1 | 12/2004 |
| WO | WO-2008/047831 A1 | 4/2008 |
| WO | WO-2009/091826 A2 | 7/2009 |
| WO | WO-2011/057158 A1 | 5/2011 |
| WO | WO-2012/093101 A1 | 7/2012 |
| WO | WO-2012/177782 A1 | 12/2012 |
| WO | WO-2013/166436 A1 | 11/2013 |
| WO | WO-2013/192345 A1 | 12/2013 |
| WO | WO-2014/002051 A2 | 1/2014 |
| WO | WO-2014/002052 A1 | 1/2014 |
| WO | WO-2014/002053 A1 | 1/2014 |
| WO | WO-2014/002054 A1 | 1/2014 |
| WO | WO-2014/002057 A1 | 1/2014 |
| WO | WO-2014/002058 A2 | 1/2014 |
| WO | WO-2014/002059 A1 | 1/2014 |
| WO | WO-2014/005150 A1 | 1/2014 |
| WO | WO-2014/009833 A2 | 1/2014 |
| WO | WO-2014/037480 A1 | 3/2014 |
| WO | WO-2014/116880 A1 | 7/2014 |
| WO | WO-2015/008861 A1 | 1/2015 |
| WO | WO-2015/021166 A2 | 2/2015 |
| WO | WO-2015/054569 A1 | 4/2015 |
| WO | WO-2015/130784 A1 | 9/2015 |
| WO | WO-2015/130795 A1 | 9/2015 |
| WO | WO-2015/130806 A1 | 9/2015 |
| WO | WO-2015/130830 A1 | 9/2015 |
| WO | WO-2015/130838 A1 | 9/2015 |
| WO | WO-2015/130842 A2 | 9/2015 |
| WO | WO-2015/130845 A1 | 9/2015 |
| WO | WO-2015/130854 A1 | 9/2015 |
| WO | WO-2017/035348 A1 | 3/2017 |
| WO | WO-2017/035349 A1 | 3/2017 |
| WO | WO-2017/035351 A1 | 3/2017 |
| WO | WO-2017/035352 A1 | 3/2017 |
| WO | WO-2017/035353 A1 | 3/2017 |
| WO | WO-2017/035355 A1 | 3/2017 |
| WO | WO-2017/035357 A1 | 3/2017 |
| WO | WO-2017/035360 A1 | 3/2017 |
| WO | WO-2017/035361 A1 | 3/2017 |
| WO | WO-2017/035362 A1 | 3/2017 |
| WO | WO-2017/035401 A1 | 3/2017 |
| WO | WO-2017/035405 A1 | 3/2017 |
| WO | WO-2017/035408 A1 | 3/2017 |
| WO | WO-2017/035409 A1 | 3/2017 |
| WO | WO-2017/035411 A1 | 3/2017 |
| WO | WO-2017/035413 A2 | 3/2017 |
| WO | WO-2017/035415 A1 | 3/2017 |
| WO | WO-2017/035417 A1 | 3/2017 |
| WO | WO-2017/035418 A1 | 3/2017 |
| WO | WO-2017/098328 A2 | 6/2017 |
| WO | WO-2017/127761 A1 | 7/2017 |
| WO | WO-2017/136395 A1 | 8/2017 |
| WO | WO-2018/005552 A1 | 1/2018 |
| WO | WO-2018/026722 A1 | 2/2018 |
| WO | WO-2018/160889 A1 | 9/2018 |
| WO | WO-2018/160891 A1 | 9/2018 |
| WO | WO-2018/160892 A1 | 9/2018 |
| WO | WO-2019/028284 A1 | 2/2019 |
| WO | WO-2019/070714 A1 | 4/2019 |
| WO | WO-2020/069024 A1 | 4/2020 |
| WO | WO-2020/109343 A1 | 6/2020 |
| WO | WO-2021/021909 A1 | 2/2021 |

OTHER PUBLICATIONS

U.S. Appl. No. 16/006,533, Wiles et al.
"Are There Any Treatments for ALS?" WebMD, <https://www.webmd.com/brain/understanding-als-treatment#1>, retrieved on May 3, 2019 (8 pages).
"Arteriosclerosis/atherosclerosis," Mayo Clinic, <https://www.mayoclinic.org/diseases-conditions/arteriosclerosis-atherosclerosis/diagnosis-treatment/drc-20350575>, retrieved on Apr. 24, 2018 (10 pages).
"Cancer," MedLine Plus, <http://www.nlm.nih.gov/medlineplus/cancer.html>, retrieved Jul. 6, 2007 (10 pages).
"Dermatomyositis," Mayo Clinic, <https://www.mayoclinic.org/diseases-conditions/dermatomyositis/diagnosis-treatment/drc-20353192>, retrieved on Aug. 1, 2017 (7 pages).
"History of Changes for Study: NCT03053102—A Treatment Study of ACH-0144471 in Patients With Paroxysmal Nocturnal Hemoglobinuria (PNH)," U.S. National Library of Medicine, available at: <https://clinicaltrials.gov/ct2/history/NCT03053102?V_4=View#StudyPageTop>, submitted Jun. 6, 2017, retrieved Mar. 9, 2021 (3 pages).
"NCT03472885—A Treatment Study of ACH-0144471 in Patients With Paroxysmal Nocturnal Hemoglobinuria (PNH) With Inadequate Response to Eculizumab (PNH)," U.S. National Library of Medicine, available at: <https://clinicaltrials.gov/ct2/show/NCT03472885>, first posted Mar. 21, 2018, last update posted Dec. 3, 2019, retrieved Mar. 27, 2020 (7 pages).
"Patient Information for TARPEYO (tar-PAY-oh) (budesonide) delayed release capsules," Calliditas Therapeutics AB, 2021 (2 pages).
"Reperfusion injury," Wikipedia, <https://en.wikipedia.org/wiki/Reperfusion_injury>, retrieved Apr. 30, 2020 (8 pages).
"Treatment for Multiple Sclerosis," WebMD, <https://www.webmd.com/multiple-sclerosis/ms-treatment#1>, retrieved on May 3, 2019 (24 pages).
"What Are the Treatments for Cirrhosis?," WebMD, <https://www.webmd.com/digestive-disorders/understanding-cirrhosis-treatment#1>, retrieved May 3, 2019 (15 pages).
"What is Cardiovascular Disease?" American Heart Association, <https://www.heart.org/en/health-topics/consumer-healthcare/what-is-cardiovascular-disease>, last reviewed May 31, 2017 (4 pages).
"What is Dementia?" Alzheimer's Association, <https://www.alz.org/alzheimers-dementia/what-is-dementia>, retrieved on Nov. 17, 2020 (6 pages).
Airey et al., "A Convenient Preparation of Thieno[3,2-c]pyrazole," Synthesis. 46: 96-100 (2014).
Andrighetto et al., "Complement and Complement Targeting Therapies in Glomerular Diseases," Int J Mol Sci. 20(24):6336 (Dec. 2019), available <https://www.ncbi.nlm.nih.gov/pmc/articles/PMC6940904/>, retrieved on May 26, 2022 (21 pages).
Armand, "Fatty liver disease: What it is and what to do about it," Harvard Health Publishing, <https://www.health.harvard.edu/blog/fatty-liver-disease-what-it-is-and-what-to-do-about-it-2019011015746>, dated Jan. 10, 2019, retrieved May 2, 2019 (3 pages).
Babiker et al., "Transfer of prostasomal CD59 to CD59-deficient red blood cells results in protection against complement-mediated hemolysis," Am J Reprod Immunol. 47(3): 183-92 (2002) (Abstract Only).
Barraclough et al., "Synthesis of (2S,3R)- and (2S,3S)-[3-$^2$H$_1$]-proline via highly selective hydrolysis of a silyl enol ether," Tetrahedron Letters. 46(1): 4653-4655 (2005).
Barraclough et al., "Two separate and distinct syntheses of stereospecifically deuteriated samples of (2S)-proline," Org Biomol Chem. 4(8):1483-1491 (2006).
Borowitz et al., "Guidelines for the Diagnosis and Monitoring of Paroxysmal Nocturnal Hemoglobinuria and Related Disorders by Flow Cytometry," Cytometry B Clin Cytom. 78B(4): 211-230 (2010).

(56) References Cited

OTHER PUBLICATIONS

Brodsky, "Eculizumab: another breakthrough," Blood. 129(8):922-3 (2017).
Carter, "Complement Activation: An Emerging Player in the Pathogenesis of Cardiovascular Disease," Scientifica. 2012:402783 (2012) (14 pages).
CAS RN 1236228-05-9, dated Aug. 16, 2010 (1 page).
CAS RN 1236251-51-6, dated Aug. 17, 2010 (2 pages).
CAS RN 1270608-88-2, dated 2019 (1 page).
CAS RN 1277041-86-7, dated Apr. 8, 2011 (2 pages).
Cofiell et al., "Eculizumab reduces complement activation, inflammation, endothelial damage, thrombosis, and renal injury markers in aHUS," Blood. 125(21):3253-62 (2015).
Cole et al. "Structure of 3,4-Dichloroisocoumarin-Inhibited Factor D," Acta Crystallogr D Biol Crystallogr. 54(Pt 5): 711-717 (1998).
Compound Summary for CID 1129904, PubChem. <https://pubchem.ncbi.nlm.nih.gOv/compound/1129904> retrieved Jul. 14, 2020, created Jul. 10, 2005 (10 pages).
Compound Summary for CID 118324207, PubChem, <https://pubchem.ncbi.nlm.nih.gov/compound/118324207>, created Feb. 23, 2016, retrieved on Jul. 14, 2020 (8 pages).
Compound Summary for CID 123543544, PubChem, <https://pubchem.ncbi.nlm.nih.gov/compound/123543544>, created on Jan. 25, 2017, retrieved on Jul. 13, 2020 (8 pages).
Compound Summary for CID 134222466, PubChem, <https://pubchem.ncbi.nlm.nih.gov/compound/134222466>, created on Jun. 23, 2018, retrieved on Jul. 14, 2020 (11 pages).
Compound Summary for CID 59912842, PubChem, <https://pubchem.ncbi.nlm.nih.gov/compound/59912842>, created Aug. 20, 2012, retrieved Jul. 14, 2020 (9 pages).
Damasio, "Alzheimer's disease and related dementias," Cecil Textbook of Medicine, 20th Edition, vol. 2. Bennett and Plum, 1992-6 (1996).
Database Registry Chemical Abstracts Service, Columbus, Ohio, Accession No. RN1236248-20-6, Entered STN: Aug. 16, 2010 (1 page).
Database Registry Chemical Abstracts Service, Columbus, Ohio, Accession No. RN1380849-41-1, Entered STN: Jul. 3, 2012 (2 pages).
De Luca et al., "HIV-1 integrase strand-transfer inhibitors: Design, synthesis and molecular modeling investigation," Eur J Med Chem. 46(2): 756-764 (2011).
DeZern et al., "Paroxysmal nocturnal hemoglobinuria: a complement-mediated hemolytic anemia," available in PMC Dec. 30, 2015, published in final edited form as: Hematol Oncol Clin North Am. 29(3):479-94 (2015) (18 pages).
Donthiri et al., "Copper-Catalyzed C-H Functionalization of Pyridines and Isoquinolines with Vinyl Azides: Synthesis of Imidazo Heterocycles," J Org Chem. 79(22): 11277-11284 (2014).
Dormoy et al., "Synthesis of N-t-Butoxycarbonyl-4,4-dideuterio-L-proline," Synthesis. 1: 81-82 (1986).
Ellis-Pegler et al., "An Orally Administered Small Molecule Factor D Inhibitor (ACH-4471) For Treatment of PNH and Complement Diseases: Preliminary Phase 1 Results In Healthy Volunteers," European Hematology Association. Abstract LB2250, available <https://library.ehaweb.org/eha/2016/21st/135361/roderick.b.ellis-pegler.an.orally.administered.small.molecule.factor.d.html>, dated May 19, 2016 (2 pages).
Ellis-Pegler et al., "An Orally Administered Small Molecule Factor D Inhibitor (ACH-4471) For Treatment of PNH, C3G and Complement—Mediated Diseases: Interim Phase 1 Results In Healthy Volunteers," European Hematology Association, Copenhagen 21st Congress, June 9-12, Abstract ID: EHA-4145 (2016) (1 page).
Extended European Search Report for European Application No. 18761960.6, dated Mar. 1, 2021 (10 pages).
Extended European Search Report for European Application No. 18840849.6, dated Mar. 17, 2021 (11 pages).
Extended European Search Report for European Application No. 19807154.0, dated Feb. 7, 2022 (9 pages).
Extended European Search Report for European Application No. 19857780.1, dated May 13, 2022 (9 pages).
Extended European Search Report for European Application No. 19897806.6, dated Jul. 18, 2022 (12 pages).
Gadhachanda et al., CAplus Database Summary Sheet for Document No. 164:507515, Accession No. 2016:627420, CAplus on STN. (2016) (6 pages).
Gavrillaki et al., "275 Small Molecule Factor D Inhibitors Block Complement Activation in Paroxysmal Nocturnal Hemoglobinuria and Atypical Hemolytic Uremic Syndrome," ASH 57th Annual Meeting & Exposition, Session: 101. Dec. 6, 2015 (2 pages).
Gilkeson, "Complement-Targeted Therapies in Lupus," Curr Treat Options in Rheum. 1:10-18 (Jan. 22, 2015).
Golub et al., "Molecular classification of cancer: class discovery and class prediction by gene expression monitoring," Science. 286(5439):531-537 (1999) (8 pages).
Gura, "Systems for identifying new drugs are often faulty," Science. 278(5340):1041-2 (1997).
Haddrill, "Stargardt's Disease (Fundus Flavimaculatus)," All About Vision, <https://www.allaboutvision.com/conditions/stargardts.htm#article-section-2>, published Mar. 4, 2019, retrieved May 3, 2019 (5 pages).
Harder et al., "Incomplete inhibition by eculizumab: mechanistic evidence for residual C5 activity during strong complement activation," Blood.129(8):970-80 (2017).
Harris et al., "Developments in anti-complement therapy; from disease to clinical trial," Mol Immunol. 102:89-119 (Oct. 2018).
Hartmann et al., "Diagnostic Specificity of Sucrose Hemolysis Test for Paroxysmal Nocturnal Hemoglobinuria," Blood. 35(4):462-475 (1970).
Hecker et al., "Liver-Targeted Prodrugs of 2'-C-Methyladenosine for Therapy of Hepatitis C Virus Infection," J Med Chem. 50(16): 3891-3896 (2007).
Hom et al., "Complement Inhibitors for Treatment of Geographic Atrophy and Advanced Nonexudative AMD," Retinal Physician. 16:28-31 (Mar. 1, 2019) (7 pages).
Hruby et al., "$^{13}$C Nuclear Magnetic Resonance Studies of the Peptide Hormones Oxytocin, Arginine Vasopressin, Isotocin, Mesotocin, Glumitocin, Aspartocin, Related Analogues, and Diastereoisomers. Use of Specifically Deuterated Hormone Derivatives for Assignments and Effects of Structural Changes on $^{13}$C NMR Chemical Shifts in Peptides," J Am Chem Soc. 101(1):202-212 (1979).
Hu et al., "Evidence of complement dysregulation in outer retina of Stargardt disease donor eyes," Redox Biol. 37:101787 (2020) (10 pages).
International Search Report and Written Opinion for International Application No. PCT/US2015/017523, dated May 14, 2015 (7 pages).
International Search Report and Written Opinion for International Application No. PCT/US2015/017538, dated May 14, 2015 (8 pages).
International Search Report and Written Opinion for International Application No. PCT/US2015/017554, dated May 14, 2015 (7 pages).
International Search Report and Written Opinion for International Application No. PCT/US2015/017583, dated May 27, 2015 (12 pages).
International Search Report and Written Opinion for International Application No. PCT/US2015/017593, dated Jun. 16, 2015 (6 pages).
International Search Report and Written Opinion for International Application No. PCT/US2015/017597, dated Jan. 29, 2016 (10 pages).
International Search Report and Written Opinion for International Application No. PCT/US2015/017600, dated May 27, 2015 (12 pages).
International Search Report and Written Opinion for International Application No. PCT/US2015/017609, dated May 29, 2015 (6 pages).
International Search Report and Written Opinion for International Application No. PCT/US2016/048688, dated Dec. 28, 2016 (11 pages).

(56) References Cited

OTHER PUBLICATIONS

International Search Report and Written Opinion for International Application No. PCT/US2016/048690, dated Dec. 28, 2016 (11 pages).
International Search Report and Written Opinion for International Application No. PCT/US2016/048693, dated Jan. 13, 2017 (11 pages).
International Search Report and Written Opinion for International Application No. PCT/US2016/048695, dated Dec. 30, 2016 (10 pages).
International Search Report and Written Opinion for International Application No. PCT/US2016/048696, dated Jan. 5, 2017 (10 pages).
International Search Report and Written Opinion for International Application No. PCT/US2016/048701, dated Jan. 10, 2017 (10 pages).
International Search Report and Written Opinion for International Application No. PCT/US2016/048704, dated Dec. 27, 2016 (7 pages).
International Search Report and Written Opinion for International Application No. PCT/US2016/048707, dated Jan. 5, 2017 (10 pages).
International Search Report and Written Opinion for International Application No. PCT/US2016/048709, dated Jan. 17, 2017 (9 pages).
International Search Report and Written Opinion for International Application No. PCT/US2016/048710, dated Jan. 5, 2017 (8 pages).
International Search Report and Written Opinion for International Application No. PCT/US2016/048779, dated Dec. 27, 2016 (8 pages).
International Search Report and Written Opinion for International Application No. PCT/US2016/048783, dated Feb. 3, 2017 (8 pages).
International Search Report and Written Opinion for International Application No. PCT/US2016/048787, dated Jan. 5, 2017 (13 pages).
International Search Report and Written Opinion for International Application No. PCT/US2016/048788, dated Jan. 5, 2017 (12 pages).
International Search Report and Written Opinion for International Application No. PCT/US2016/048793, dated Dec. 28, 2016 (8 pages).
International Search Report and Written Opinion for International Application No. PCT/US2016/048795, dated Feb. 17, 2017 (12 pages).
International Search Report and Written Opinion for International Application No. PCT/US2016/048797, dated Jan. 5, 2017 (12 pages).
International Search Report and Written Opinion for International Application No. PCT/US2016/048799, dated Nov. 15, 2016 (7 pages).
International Search Report and Written Opinion for International Application No. PCT/US2016/048800, dated Jan. 5, 2017 (12 pages).
International Search Report and Written Opinion for International Application No. PCT/US21/18871, dated May 24, 2021 (24 pages).
International Search Report and Written Opinion for International Application No. PCT/US21/21563, dated May 18, 2021 (15 pages).
International Search Report for International Application No. PCT/US18/20530, dated Jun. 25, 2018 (3 pages).
International Search Report for International Application No. PCT/US18/20531, dated May 15, 2018 (3 pages).
International Search Report for International Application No. PCT/US20/24017, dated Jun. 26, 2020 (3 pages).
International Search Report for International Application No. PCT/US2018/020528, dated Apr. 24, 2018 (3 pages).
International Search Report for International Application No. PCT/US2018/045057, dated Nov. 15, 2018 (5 pages).
International Search Report for International Application No. PCT/US2019/034210, dated Sep. 13, 2019 (4 pages).
International Search Report for International Application No. PCT/US2019/047252, dated Dec. 17, 2019 (4 pages).
International Search Report for International Application No. PCT/US2019/050065, dated Feb. 25, 2020 (4 pages).
International Search Report for International Application No. PCT/US2019/050073, dated Nov. 21, 2019 (3 pages).
International Search Report for International Application No. PCT/US2019/053012, dated Jan. 28, 2020 (4 pages).
International Search Report for International Application No. PCT/US2019/066999, dated Feb. 12, 2020 (3 pages).
Ishibashi et al., "Four-year outcomes of intravitreal aflibercept treatment for neovascular age-related macular degeneration using a treat-and-extend regimen in Japanese patients," Ther Adv Ophthalmol. 13:1-5 (2021).
Jensen et al., "Associations between the Complement System and Choroidal Neovascularization in Wet Age-Related Macular Degeneration," Int J Mol Sci. 21(24):9752 (2020) (28 pages).
Johnson et al., "Relationships between drug activity in NCI preclinical in vitro and in vivo models and early clinical trials," Br J Cancer. 84(10):1424-31 (2001).
Józsi, "Anti-Complement Autoantibodies in Membranoproliferative Glomerulonephritis and Dense Deposit Disease", *An Update on Glomerulopathies—Etiology and Pathogenesis*. Prof. Sharma Prabhakar, 31-46 (2011) (18 pages).
Kathuria, "Membranoproliferative Glomerulonephritis Medication," Medscape, <https://emedicine.medscape.com/article/240056-medication>, updated Jun. 23, 2016, retrieved May 3, 2019 (1 page).
Kinman, "COPD Drugs: A List of Medications to Help Relieve Your Symptoms," Healthline, <https://www.healthline.com/health/copd/drugs>, retrieved on May 3, 2019 (12 pages).
Kocinsky et al., "Abstract SaO018: Factor D inhibition with ACH-4471 to reduce complement alternative pathway hyperactivity and proteinuria in C3 glomerulopathy: preliminary proof of concept data," Nephrology Dialysis Transplantation. 33(Supplement 1):i322-3 (2018) (1 page).
Komiya et al., CAplus Database Summary Sheet for Document No. 162:229476, Accession No. 2015:126147, CAplus on STN. (2015) (2 pages).
Konar et al., "Eculizumab treatment and impaired opsonophagocytic killing of meningococci by whole blood from immunized adults," Blood. 130(7):891-9 (2017).
Krauss, "Laboratory Diagnosis of Paroxysmal Nocturnal Hemoglobinuria," Annals of Clinical & Laboratory Science. 33(4):401-406 (2003).
Kuang et al., "Synthesis of (Z)-1-bromo-1-alkenes and terminal alkynes from anti-2,3-dibromoalkanoic acids by microwave-induced reaction," Tetrahedron. 61(16):4043-4052 (2005).
Lala et al., "Role of nitric oxide in tumor progression: lessons from experimental tumors," Cancer Metastasis Rev. 17(1):91-106 (1998).
Lassmann, "What drives disease in multiple sclerosis: Inflammation or neurodegeneration?" Clinical and Experimental Neuroimmunology. 1:2-11 (2010).
Layzer, "Degenerative Diseases of the Nervous System," *Cecil Textbook of Medicine, 20th Edition, vol. 2*. J. Claude Bennett and Fred Plum, p. 2050-2057 (1996) (9 pages).
Le et al., "A mechanistic pharmacokinetic/pharmacodynamic model of factor D inhibition in cynomolgus monkeys by lampalizumab for the treatment of geographic atrophy," J Pharmacol Exp Ther. 355(2):288-96 (2015).
MacKay et al., "Rapid Synthesis of the N-Methylwelwitindolinone Skeleton," Org Lett. 7(16):3421-4 (2005).
Mantegazza et al., "Complement Inhibition for the Treatment of Myasthenia Gravis," Immunotargets Ther. 9:317-31 (2020), <https://www.ncbi.nlm.nih.gov/pmc/articles/PMC7751298/>, retrieved on May 26, 2022 (24 pages).
Mastellos et al., "Complement in paroxysmal nocturnal hemoglobinuria: exploiting our current knowledge to improve the treatment landscape," available in PMC Apr. 2, 2015, published in final edited form as: Expert Rev Hematol. 7(5):583-98 (2014) (26 pages).
Noris et al., "Overview of Complement Activation and Regulation," Semin Nephrol. 33(6):479-92 (2013).
Office Action issued for Eurasian Patent Application No. 201992005, dated Oct. 23, 2020 (6 pages).

(56) References Cited

OTHER PUBLICATIONS

Okutani et al., "Conversion of Bromoalkenes into Alkynes by Wet Tetra-n-butylammonium Fluoride," J Org Chem. 74(1):442-444 (2009).
Oseini et al., "Therapies in Non-Alcoholic Steatohepatitis (NASH)," available in PMC Jan. 1, 2018, published in final edited form as: Liver Int. 37(Suppl 1):97-103 (2017) (15 pages).
Oshima et al., "Correlation between improvement in visual acuity and QOL after Ranibizumab treatment for age-related macular degeneration patients: QUATRO study," BMC Ophthalmol. 21(1):58 (2021) (11 pages).
Pandya et al., "Complement System in Lung Disease," Am J Respir Cell Mol Biol. 51(4):467-473 (2014).
Parker, "Update on the diagnosis and management of paroxysmal nocturnal hemoglobinuria," Hematology Am Soc Hemtol Educ Program. 2016(1):208-16 (2016).
Partial Supplementary European Search Report for European Application No. 18761960.6, dated Nov. 27, 2020 (12 pages).
Partial Supplementary European Search Report for European Application No. 19857913.8, dated Apr. 13, 2022 (17 pages).
Patel et al., "In Vitro Combination Studies of ACH-4471 with Eculizumab to Assess a Potential 'Switch' Treatment Approach for Paroxysmal Nocturnal Hemoglobinuria," 59th American Society of Hematology Annual Meeting and Exposition, Dec. 9-12, Atlanta, Georgia. Poster Abstract 2198 (2017) (1 page).
Pearce et al., Chapter 18: Failure modes in anticancer drug discovery and development. *Cancer Drug Design and Discovery*. Stephen Neidle, 424-435 (2008).
Peifer et al., "Design, Synthesis, and Biological Evaluation of Novel 3-Aryl-4-(1H-indole-3yl)-1,5-dihydro-2H-pyrrole-2-ones as Vascular Endothelial Growth Factor Receptor (VEGF-R) Inhibitors," J Med Chem. 51(13):3814-3824 (2008).
Pugsley et al., "Inhibitors of the complement system currently in development for cardiovascular disease," Cardiovasc Toxicol. 3(1):43-69 (2003).
Qu et al., "Recent Developments in Low Molecular Weight Complement Inhibitors," available in PMC, Dec. 1, 2010, published in final edited form as: Mol Immunol. 47(2-3):185-195 (2009) (25 pages).
Quesada et al., "One-pot conversion of activated alcohols into terminal alkynes using manganese dioxide in combination with the Bestmann-Ohira reagent," Tetrahedron Letters. 46:6473-6476 (2005).
Ricklin et al., "Complement in immune and inflammatory disorders: pathophysiological mechanisms," J Immunol. 190(8):3831-3838 (2013).
Risitano et al., "Complement fraction 3 binding on erythrocytes as additional mechanism of disease in paroxysmal nocturnal hemoglobinuria patients treated by eculizumab," Blood. 113(17):4094-4100 (2009) (25 pages).
Risitano et al., "Danicopan: an oral complement factor D inhibitor for paroxysmal nocturnal hemoglobinuria," Haematologica. 106(12):3188-97 (2021).
Risitano et al., "Peptide inhibitors of C3 activation as a novel strategy of complement inhibition for the treatment of paroxysmal nocturnal hemoglobinuria," Blood. 123(13):2094-101 (2014).
Risitano et al., "Safety and Pharmacokinetics of the Complement Inhibitor TT30 in a Phase I Trial for Untreated PNH Patients" Blood. 126(23): 2137 (2015) (Abstract Only) (7 pages).
Risitano et al., "Toward complement inhibition 2.0: Next generation anticomplement agents for paroxysmal nocturnal hemoglobinuria," Am J Hematol. 93(4):564-77 (2018).
Risitano, "Anti-Complement Treatment in Paroxysmal Nocturnal Hemoglobinuria: Where we Stand and Where we are Going," Transl Med UniSa. 8:43-52 (2014).
Risitano, "Paroxysmal nocturnal hemoglobinuria in the era of complement inhibition," Am J Hematol. 91(4):359-60 (2016).
Rohrer et al., "Eliminating complement factor D reduces photoreceptor susceptibility to light-induced damage," Invest Ophthalmol Vis Sci. 48(11):5282-9 (2007).
Roth et al., "Further Improvements of the Synthesis of Alkynes from Aldehydes," Synthesis. 1:59-62 (2004).
Ruiz-Gómez et al., "Structure-Activity Relationships for Substrate-Based Inhibitors of Human Complement Factor B," J Med Chem. 52(19):6042-6052 (2009).
Salifu, "Chronic Glomerulonephritis Medication," Medscape, <https://emedicine.medscape.com/article/239392-medication>, updated Feb. 1, 2017, retrieved on May 2, 2019 (1 page).
Segers et al., "Complement Alternative Pathway Activation in Human Nonalcoholic Steatohepatitis," PLOS One. 9(10):e110053 (2014) (9 pages).
Sica et al., "Eculizumab treatment: stochastic occurrence of C3 binding to individual PNH erythrocytes," J Hematol Oncol. 10(1):126 (2017) (10 pages).
Simone, "Oncology: Introduction," Cecil Textbook of Medicine, 20th Edition, vol. 1, pp. 1004-1010, (1996) (8 pages).
Stanton et al., "Complement Factor D in Age-Related Macular Degeneration," Invest Ophthalmol Vis Sci. 52(12):8828-8834 (2011) (15 pages).
Steinle et al., "Impact of Baseline Characteristics on Geographic Atrophy Progression in the FILLY Trial Evaluating the Complement C3 Inhibitor Pegcetacoplan," Am J Ophthalmol. DOI: https://doi.org/10.1016/j.ajo.2021.02.031 (Journal Pre-proof version) (2021) (19 pages).
Strobel et al., "Anti-factor B autoantibody in dense deposit disease," Mol Immunol. 47:1476-1483 (2010).
Tandon et al., "Substrate specificity of human prolyl-4-hydroxylase," Bioorg Med Chem Lett. 8(10):1139-1144 (1998).
Tang et al.,"Palladium-Catalyzed Carbonylative Sonogashira Coupling of Aryl Bromides via tert-Butyl Isocyanide Insertion," J Org Chem. 78(7):3170-3175 (2013).
Varelas et al., "Complement in Sickle Cell Disease: Are We Ready for Prime Time?," J Blood Med. 12:177-87 (2021), <https://www.ncbi.nlm.nih.gov/pmc/articles/PMC8001680/>, dated Mar. 23, 2021, retrieved on May 26, 2022 (19 pages).
Wehling et al., "Monitoring of complement activation biomarkers and eculizumab in complement-mediated renal disorders," Clin Exp Immunol. 187(2):304-15 (2017).
Willows et al., "The role of complement in kidney disease," Clin Med (Lond). 20(2):156-60 (2020) (9 pages).
Written Opinion for International Application No. PCT/US18/20528, dated Apr. 24, 2018 (6 pages).
Written Opinion for International Application No. PCT/US18/20530, dated Jun. 25, 2018 (6 pages).
Written Opinion for International Application No. PCT/US18/20531, dated May 15, 2018 (7 pages).
Written Opinion for International Application No. PCT/US19/47252, dated Dec. 17, 2019 (6 pages).
Written Opinion for International Application No. PCT/US19/50065, dated Feb. 25, 2020 (7 pages).
Written Opinion for International Application No. PCT/US19/53012, dated Jan. 28, 2020 (5 pages).
Written Opinion for International Application No. PCT/US19/66999, dated Feb. 12, 2020 (7 pages).
Written Opinion for International Application No. PCT/US20/24017, dated Jun. 26, 2020 (6 pages).
Written Opinion for International Application No. PCT/US2018/045057, dated Nov. 15, 2018 (7 pages).
Written Opinion for International Application No. PCT/US2019/034210, dated Sep. 13, 2019 (17 pages).
Written Opinion for International Application No. PCT/US2019/050073, dated Nov. 21, 2019 (4 pages).
Yonemoto-Kobayashi et al., "Carboxylation of alkynylsilanes with carbon dioxide mediated by cesium fluoride in DMSO," Org Biomol Chem. 11(23):3773-5 (2013).
Yuan et al., "Small-molecule Factor D Inhibitors Selectively Block the Alternative Pathway of Complement in Paroxysmal Nocturnal Hemoglobinuria and Atypical Hemolytic Uremic Syndrome," Haematologica. 102(3):466-75 (2017).
Iatropoulos et al., "Cluster Analysis Identifies Distinct Pathogenetic Patterns in C3 Glomerulopathies/Immune Complex-Mediated Membranoproliferative GN," J Am Soc Nephrol. 29(1):283-94 (with supplemental material) (Jan. 2018) (36 pages).
International Preliminary Report on Patentability for International Application No. PCT/US2021/018871, dated Sep. 1, 2022 (6 pages).

(56) References Cited

OTHER PUBLICATIONS

Marinozzi et al., "C5 nephritic factors drive the biological phenotype of C3 glomerulopathies," Kidney Int. 92(5):1232-41 (Nov. 2017).

Michels et al., "Long-term follow-up including extensive complement analysis of a pediatric C3 glomerulopathy cohort," Pediatr Nephrol. 37(3):601-12 (Mar. 2022).

Zhang et al., "Defining the complement biomarker profile of C3 glomerulopathy," Clin J Am Soc Nephrol. 9(11):1876-82 (supplemental materials) (Nov. 7, 2014) (10 pages).

* cited by examiner

Compound 1  Compound 2

MORPHIC FORMS OF DANICOPAN

CROSS-REFERENCE TO RELATED APPLICATIONS

This application claims the benefit of priority to U.S. Application No. 62/727,954, filed Sep. 6, 2018. The entirety of the application is incorporated herein.

FIELD OF THE INVENTION

This invention provides advantageous isolated morphic forms of the Complement factor D inhibitors Compound 1 and Compound 2.

BACKGROUND

The complement system is a part of the innate immune system which does not adapt to changes over the course of the host's life, but is recruited and used by the adaptive immune system. For example, it assists, or complements, the ability of antibodies and phagocytic cells to clear pathogens. This sophisticated regulatory pathway allows rapid reaction to pathogenic organisms while protecting host cells from destruction. Over thirty proteins and protein fragments make up the complement system. These proteins act through opsonization (enhancing phagocytosis of antigens), chemotaxis (attracting macrophages and neutrophils), cell lysis (rupturing membranes of foreign cells), and agglutination (clustering and binding of pathogens together).

The complement system has three pathways: classical, alternative, and lectin. Complement Factor D plays an early and central role in activation of the alternative pathway of the complement cascade. Activation of the alternative complement pathway is initiated by spontaneous hydrolysis of a thioester bond within the C3 protein to produce $C3(H_2O)$, which associates with Factor B to form the $C3(H_2O)B$ complex. Complement Factor D acts to cleave Factor B within the $C3(H_2O)B$ complex to form Ba and Bb. The Bb fragment remains associated with $C3(H_2O)$ to form the alternative pathway C3 convertase $C3(H_2O)Bb$. Additionally, C3b generated by any of the C3 convertases also associates with Factor B to form C3bB, which Factor D cleaves to generate the later stage alternative pathway C3 convertase C3bBb. This latter form of the alternative pathway C3 convertase may provide important downstream amplification within all three of the defined complement pathways, leading ultimately to the recruitment and assembly of additional factors in the complement cascade pathway, including the cleavage of C5 to C5a and C5b. C5b acts in the assembly of factors C6, C7, C8, and C9 into the membrane attack complex, which can destroy pathogenic cells by lysing the cell.

The dysfunction of or excessive activation of complement has been linked to certain autoimmune, inflammatory, and neurodegenerative diseases, as well as ischemia-reperfusion injury and cancer. For example, activation of the alternative pathway of the complement cascade contributes to the production of C3a and C5a, both potent anaphylatoxins, which also have roles in a number of inflammatory disorders. Therefore, in some instances, it is desirable to decrease the response of the complement pathway, including the alternative complement pathway. Some examples of disorders mediated by the complement pathway include age-related macular degeneration (AMD), paroxysmal nocturnal hemoglobinuria (PNH), multiple sclerosis, and rheumatoid arthritis.

Age-related macular degeneration (AMD) is a leading cause of vision loss in industrialized countries. Based on a number of genetic studies, there is evidence of the link between the complement cascade and macular degeneration. Individuals with mutations in the gene encoding complement Factor H have a fivefold increased risk of macular degeneration and individuals with mutations in other complement factor genes also have an increased risk of AMD. Individuals with mutant Factor H also have increased levels of C-reactive protein, a marker of inflammation. Without adequate functioning of Factor H, the alternative pathway of the complement cascade is overly activated leading to cellular damage.

Paroxysmal nocturnal hemoglobinuria (PNH) is a non-malignant, hematological disorder characterized by the expansion of hematopoietic stem cells and progeny mature blood cells that are deficient in some surface proteins. PNH erythrocytes are not capable of modulating their surface complement activation, which leads to the typical hallmark of PNH—the chronic activation of complement mediated intravascular anemia. Currently, only one product, the anti-C5 monoclonal antibody eculizumab, has been approved in the U.S. for treatment of PNH. However, many of the patients treated with eculizumab remain anemic, and many patients continue to require blood transfusions. In addition, treatment with eculizumab requires life-long intravenous injections.

Additional complement-mediated disorders include those classified under component 3 glomerulopathy (C3G). C3G is a recently defined entity comprised of dense deposit disease (DDD) and C3 glomerulonephritis (C3GN) which encompasses a population of chronic kidney diseases wherein elevated activity of the alternative complement pathway and terminal complement pathway results in glomerular deposits made solely of complement C3 and no immunoglobulin (Ig).

Immune-complex membranoproliferative glomerulonephritis (IC-MPGN) is a renal disease which shares many clinical, pathologic, genetic and laboratory features with C3G, and therefore can be considered a sister disease of C3G. In the majority of patients with IC-MPGN, an underlying disease or disorder—most commonly infections, autoimmune diseases, or monoclonal gammopathies—are identified to which the renal disease is secondary. Patients with idiopathic IC-MPGN can have low C3 and normal C4 levels, similar to those observed in C3G, as well as many of the same genetic or acquired factors that are associated with abnormal alternative pathway activity. Although there are current hypotheses suggesting that the majority of IC-MPGN is attributable to over activity of the classical pathway, those patients with a low C3 and a normal C4 are likely to have significant overactivity of the alternative pathway. IC-MPGN patients with a low C3 and a normal C4 may benefit from alternative pathway inhibition.

Other disorders that have been linked to the complement cascade include atypical hemolytic uremic syndrome (aHUS), hemolytic uremic syndrome (HUS), abdominal aortic aneurysm, hemodialysis complications, hemolytic anemia, or hemodialysis, neuromyelitis optica (NMO), myasthenia gravis (MG), fatty liver, nonalcoholic steatohepatitis (NASH), liver inflammation, cirrhosis, liver failure, dermatomyositis, and amyotrophic lateral sclerosis.

Factor D is an attractive target for inhibition or regulation of the complement cascade due to its early and essential role in the alternative complement pathway, and for its potential role in signal amplification within the classical and lectin complement pathways. Inhibition of Factor D effectively interrupts the pathway and attenuates the formation of the membrane attack complex.

Novartis PCT patent publication WO2012/093101 titled "Indole compounds or analogues thereof useful for the treatment of age-related macular degeneration" describes certain Factor D inhibitors. Additional Factor D inhibitors are described in Novartis PCT patent publications WO2012093101, WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, and WO2016088082.

Additional complement factor D inhibitors are described in U.S. Pat. Nos. 9,598,446; 9,643,986; 9,663,543; 9,695,205; 9,732,103; 9,732,104; 9,758,537; 9,796,741; 9,828,396; 10,000,516; 10,005,802; 10,011,612; 10,081,645; 10,087,203; 10,092,584; 10,100,072; 10,138,225; 10,189,869; 10,106,563; 10,301,336; and 10,287,301; International Publication Nos. WO2019/028284; WO2018/160889; WO2018/160891; WO2018/160892; WO2017/035348; WO2017/035349; WO 2017/035351; WO 2017/035352; WO 2017/035353; WO 2017/035355; WO2017/035357; WO2017/035360; WO2017/035361; WO2017/035362; WO2017/035415; WO2017/035401; WO2017/035405; WO2017/035413; WO2017/035409; WO2017/035411; WO2017/035417; WO2017/035408 WO2015/130784; WO2015/130795; WO2015/130806; WO2015/130830; WO2015/130838; WO2015/130842; WO2015/130845; and WO2015/130854; and U.S. Patent Publication Nos. US 2016-0361329; US 2016-0362432; US 2016-0362433; US 2016-0362399; US 2017-0056428; US 2017-0057950; US 2017-0057993; US 2017-0189410; US 2017-0226142; US 2017-0260219; US 2017-0298084; US 2017-0298085; US 2018-0022766; US 2018-0022767; US 2018-0072762; US 2018-0030075; US 2018-0169109; US 2018-0177761; US 2018-0179185; US 2018-0179186; US 2018-0179236; US 2018-0186782; US 2018-0201580; US 2019-0031692; US 2019-0048033; US 2019-0144473; and US 2019-0211033 all owned by Achillion Pharmaceuticals, Inc.

Given the wide variety of medical disorders that are caused by detrimental immune or inflammatory responses, it would be beneficial to provide additional advantageous compounds and forms thereof for advantageous delivery that may increase therapeutic activity and/or stability.

SUMMARY

It has been discovered that Compound 1 and Compound 2 can be prepared in highly purified morphic forms that exhibit unexpected advantageous therapeutic properties. Compound 1 is disclosed in PCT Application WO2015130795 assigned to Achillion Pharmaceuticals and Compound 2 is disclosed in PCT Application WO2017035353 assigned to Achillion Pharmaceuticals. The morphic form of Compound 1 is referred to as Form II and the morphic form of Compound 2 is referred to as Form I. These morphic forms are beneficial for therapeutic efficacy and for the manufacture of pharmaceutical formulations.

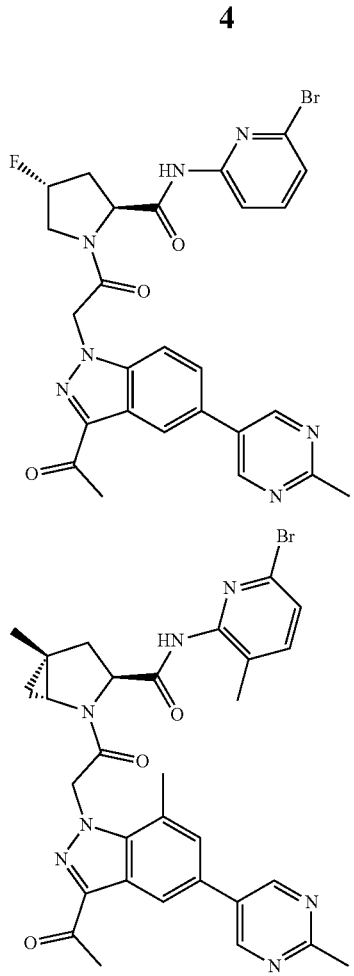

Form II of Compound 1 is an unexpected, highly stable, highly crystalline form of solid Compound 1. As discussed in Example 2 and Example 3, a crystallization study involving 38 unique solvent systems, suspension- and solution-based crystallization modes, and temperatures ranging between 5 and 40° C. was conducted. The study produced a superior crystalline form, Form II, which was identified in five experiments. Form II is crystalline by PLM (FIG. 4D) and PXRD (FIG. 4C) and contains 2.7% bound water (~0.9 eq.) that is released with a broad endotherm in the DSC from 40-125° C. A final melting endotherm was observed at 155.3° C. (FIG. 4B). Heating Form II past the dehydration endotherm and returning to room temperature does not change the crystal-form by PXRD or water content by TGA, indicating that it is a reversible hydrate.

As discussed in Example 4, experimentation on Form II led to the discovery of five other crystal forms: Form III (hydrate), Form IV (hydrate), Form V (hydrate), Form VI (mixed solvate/hydrate), and Form VII (mixed solvate/hydrate). The forms were characterized and select forms were assessed for relative stability at 25° C. (Example 5). Form II was shown to be the stable hydrate at or below a water activity value ($a_w$) of 0.55 (at 25° C.). Form V was determined to be a stable hydrate at aw=0.75 and Form III was a stable hydrate at $a_w$=0.90.

Form I of Compound 2 is also an unexpected, highly stable, highly crystalline form. As discussed in Example 8 and shown in FIG. 13, the XRPD of Compound 2 Form I exhibits a highly crystalline form. As discussed in Example 7, a study was designed to probe the solid behavior of Compound 2. A wide variety of solvents and solvent systems were used resulting in the discovery of Form I.

Form II of Compound 1 and Form I of Compound 2 have advantageous properties for use as active pharmaceutical ingredients in a solid dosage form and may have increased efficacy in such a formulation.

In one embodiment, Form II of Compound 1 is produced by recrystallization from heptane and isopropyl alcohol, as described in more detail below. In one embodiment, Form II of Compound 1 is characterized by a PXRD pattern substantially similar to that set forth in FIG. 4C. In one embodiment, isolated Compound 1 Form II is characterized as having about a 2-3%, for example, a 2.7% weight loss between 40 and 125° C. in a differential scanning calorimetry analysis.

In one embodiment, Form I of Compound 2 is produced by recrystallization from heptane and isopropanol, as described in more detail below. In one embodiment, Form I of Compound 2 is characterized by a XRPD pattern substantially similar to that set forth in FIG. 13. In one embodiment, isolated Compound 1 Form II is characterized as having an exothermic feature at approximately 118° C. and an endotherm onset at approximately 242° C.

Thus, the present invention generally provides an isolated morphic Form II of Compound 1, pharmaceutical compositions containing such morphic form, methods of inhibiting or reducing the activity of factor D in a host using said isolated morphic form, treating a host having a paroxysmal nocturnal hemoglobinuria or C3 glomerulopathy using the morphic form described herein, and methods of preparing such morphic form.

The present invention also generally provides an isolated morphic Form I of Compound 2, pharmaceutical compositions containing such morphic form, methods of inhibiting or reducing the activity of factor D in a host using said isolated morphic form, treating a host having a paroxysmal nocturnal hemoglobinuria (PNH) or C3 glomerulopathy (C3G) using the morphic form described herein, and methods of preparing such morphic form.

In one embodiment a pharmaceutical composition is provided comprising isolated Compound 1 morphic Form II and a pharmaceutically acceptable excipient. In one embodiment a pharmaceutical composition is provided comprising isolated Compound 2 morphic Form I and a pharmaceutically acceptable excipient.

In one aspect of the present invention, a method for treating a disorder mediated by Complement factor D is provided, for example, paroxysmal nocturnal hemoglobinuria (PNH) or C3 glomerulopathy (C3G) is provided comprising administering to a host in need thereof a therapeutically effective amount of isolated Form II of Compound 1.

In one aspect of the present invention, a method for treating a disorder selected from membranoproliferative glomerulonephritis type II (MPGNII), nonalcoholic steatohepatitis (NASH), fatty liver, liver inflammation, cirrhosis, or liver failure, dermatomyositis, and amyotrophic lateral sclerosis is provided comprising administering to a host in need thereof a therapeutically effective amount of isolated Form II of Compound 1.

In one aspect of the present invention, a method for treating a disorder selected from multiple sclerosis, arthritis, respiratory disease, cardiovascular disease, COPD, rheumatoid arthritis, atypical hemolytic uremic syndrome, and typical hemolytic uremic syndrome is provided comprising administering to a host in need thereof a therapeutically effective amount of isolated Form II of Compound 1.

In one aspect of the present invention, a method for treating a disorder selected from membrane glomerulonephritis, age-related macular degeneration (AMD), retinal degeneration, and type I diabetes or complications thereof is provided comprising administering to a host in need thereof a therapeutically effective amount of isolated Form II of Compound 1.

In one aspect of the present invention, a method for treating a disorder mediated by Complement factor D is provided, for example, paroxysmal nocturnal hemoglobinuria (PNH) or C3 glomerulopathy (C3G) is provided comprising administering to a host in need thereof a therapeutically effective amount of isolated Form I of Compound 2.

In one aspect of the present invention, a method for treating a disorder selected from membranoproliferative glomerulonephritis type II (MPGNII), nonalcoholic steatohepatitis (NASH), fatty liver, liver inflammation, cirrhosis, or liver failure, dermatomyositis, and amyotrophic lateral sclerosis is provided comprising administering to a host in need thereof a therapeutically effective amount of isolated Form I of Compound 2.

In one aspect of the present invention, a method for treating a disorder selected from multiple sclerosis, arthritis, respiratory disease, cardiovascular disease, COPD, rheumatoid arthritis, atypical hemolytic uremic syndrome, and typical hemolytic uremic syndrome is provided comprising administering to a host in need thereof a therapeutically effective amount of isolated Form I of Compound 2.

In one aspect of the present invention, a method for treating a disorder selected from membrane glomerulonephritis, age-related macular degeneration (AMD), retinal degeneration, and type I diabetes or complications thereof is provided comprising administering to a host in need thereof a therapeutically effective amount of isolated Form I of Compound 2.

In one embodiment a therapeutic method is provided to treat a patient with a complement factor D mediated disorder comprising administering an effective amount of Compound 1 Form II and a C5 inhibitor to the patient in need thereof. In one embodiment Compound 1 Form II and the C5 inhibitor have an overlapping therapeutic effect. In one embodiment a therapeutic method is provided to treat a patient with a complement factor D mediated disorder comprising administering an effective amount of Compound 1 Form II and eculizumab to the patient in need thereof. In one embodiment, Compound 1 Form II and eculizumab have an overlapping therapeutic effect. In one embodiment a therapeutic method is provided to treat a patient with a complement factor D mediated disorder comprising administering Compound 1 Form II and ravulizumab to the patient in need thereof. In one embodiment Compound 1 Form II and ravulizumab have an overlapping therapeutic effect. For example, the therapeutic effect can be combinatorial or synergistic inhibition.

In one embodiment, the AUC for Compound 1 Form II and the C5 inhibitor overlap.

In one embodiment, the C5 inhibitor is eculizumab. In one embodiment, the C5 inhibitor is ravulizumab. In one embodiment the C5 inhibitor is a small molecule. In another embodiment the C5 inhibitor is a polyclonal antibody targeting C5. In yet another embodiment the C5 inhibitor is an aptamer.

In one embodiment a therapeutic method is provided to treat a patient with a complement factor D mediated disorder comprising administering an effective amount of Compound 2 Form I and a C5 inhibitor to the patient in need thereof. In one embodiment Compound 2 Form I and the C5 inhibitor have an overlapping therapeutic effect. In one embodiment a therapeutic method is provided to treat a patient with a complement factor D mediated disorder comprising administering an effective amount of Compound 2 Form I and eculizumab to the patient in need thereof. In one embodiment, Compound 2 Form I and eculizumab have an overlapping therapeutic effect. In one embodiment a therapeutic method is provided to treat a patient with a complement factor D mediated disorder comprising administering Compound 2 Form I and ravulizumab to the patient in need thereof. In one embodiment Compound 2 Form I and ravulizumab have an overlapping therapeutic effect. For example, the therapeutic effect can be combinatorial or synergistic inhibition.

In one embodiment, the AUC for Compound 2 Form I and the C5 inhibitor overlap.

In one embodiment, the C5 inhibitor is eculizumab. In one embodiment, the C5 inhibitor is ravulizumab. In one embodiment the C5 inhibitor is a small molecule. In another embodiment the C5 inhibitor is a polyclonal antibody targeting C5. In yet another embodiment the C5 inhibitor is an aptamer.

DETAILED DESCRIPTION OF THE INVENTION

It cannot be predicted in advance whether a compound exists in more than one solid form or what the various properties of any solid form might be if one or more does exist, or whether the properties are advantageous for a therapeutic dosage form or for ease of manufacturing and or/formulation. As one example, the drug ritonavir is active in one polymorphic form and inactive in another form, and the inactive form is the more stable.

Solid forms of compounds can be characterized by analytical methods such as X-ray powder diffraction pattern (XRDP or PXRD), thermogravimetric analysis (TGA), TGA with IR off-gas analysis, differential Scanning calorimetry (DSC), melting point, FT-Raman spectroscopy, dynamic Vapor Sorption (DVS), polarized light microscopy (PLM) or other techniques known in the art.

Compound 1

Solubility and crystallization experiments produced an advantageous crystalline form, Form II. Experiments also led to the discovery of five other forms: Form III, Form IV, Form V, Form VI, and Form VII. Form II was shown to be a stable hydrate at or below a water activity ($a_w$) of 0.55.

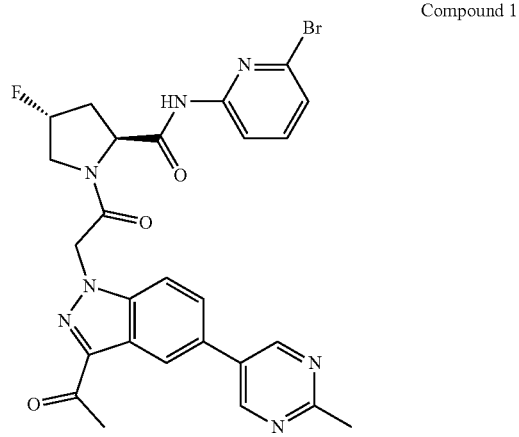 [SMILES: CC(=O)c1nn(CC(=O)N2C[C@H](F)C[C@H]2C(=O)Nc2cccc(Br)n2)c2ccc(-c3cnc(C)nc3)cc12]

Compound 1

Form II

Isolated morphic Form II of Compound 1 is provided in this invention.

Figure 4A:
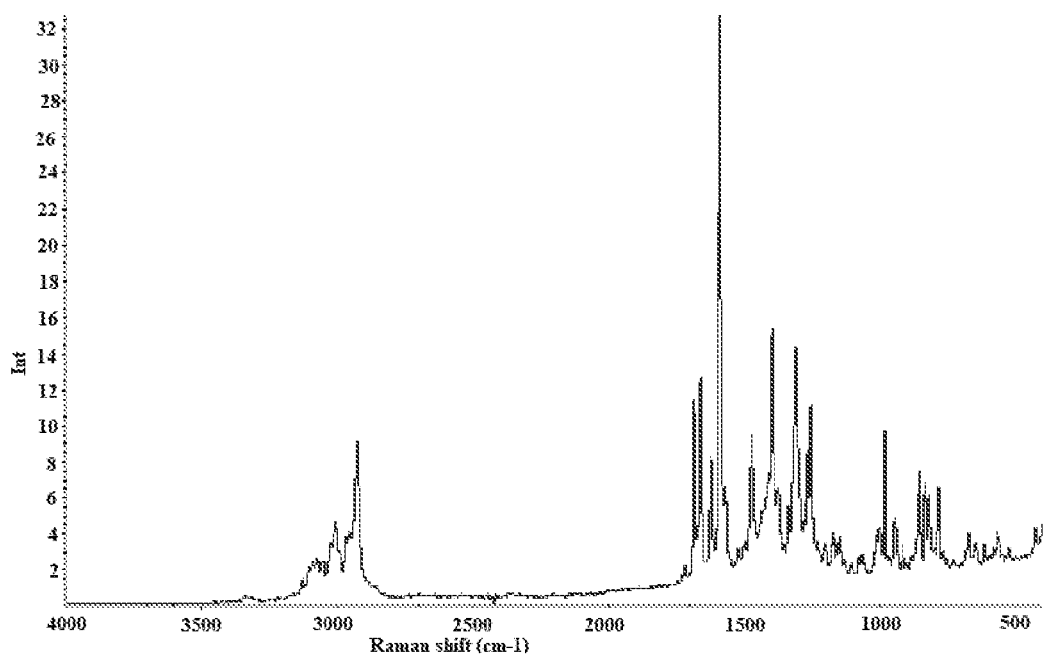
FIG. 4A is a $^1$HNMR of Compound 1 Form II as discussed in Example 4. The x-axis is the Raman shift measured in $cm^{-1}$ and the y-axis is intensity measured in counts.
Figure 4B:
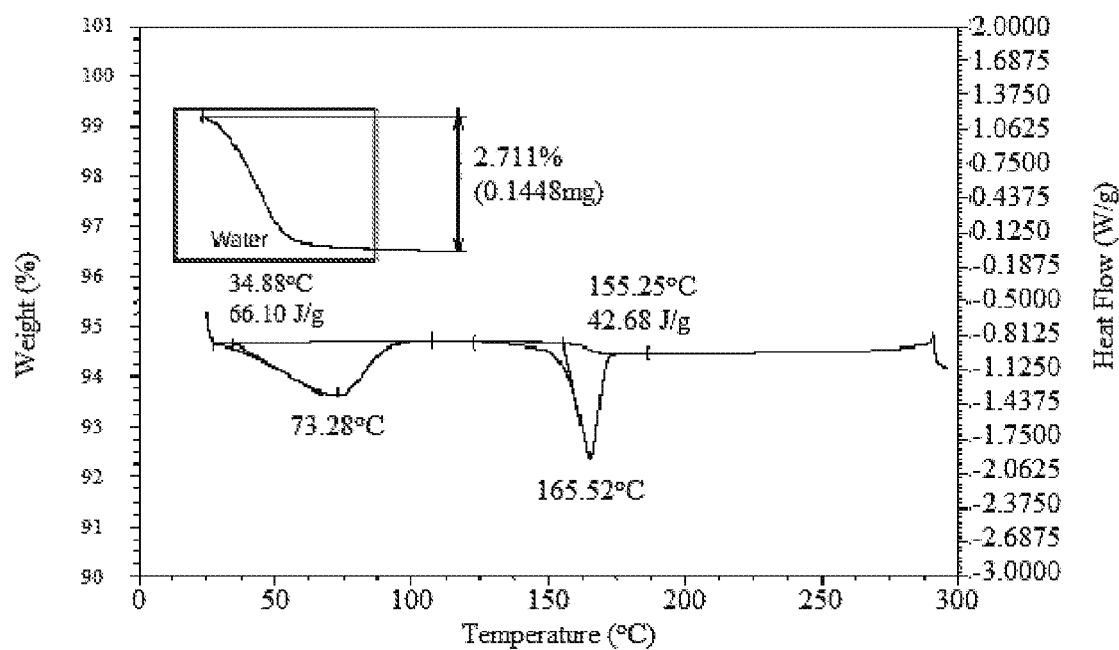
FIG. 4B is a DSC and a TGA graph of Compound 1 Form II as discussed in Example 4. The x-axis is temperature measured in ° C., the left y-axis is heat flow measured in (W/g), and the right y-axis is weight measured in percent.
Figure 4C:
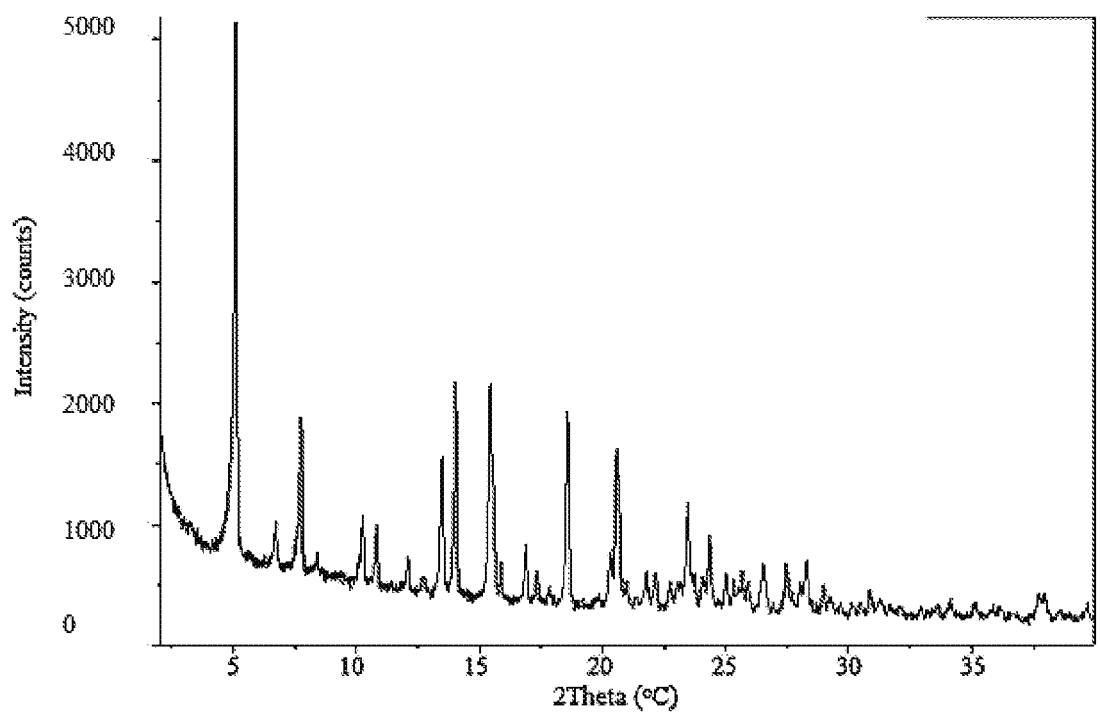
FIG. 4C is a PXRD (powder X-ray diffraction) of Compound 1 Form II as discussed in Example 4. The x-axis is 2Theta measured in degrees and the y-axis is intensity measured in counts.
Figure 4D:
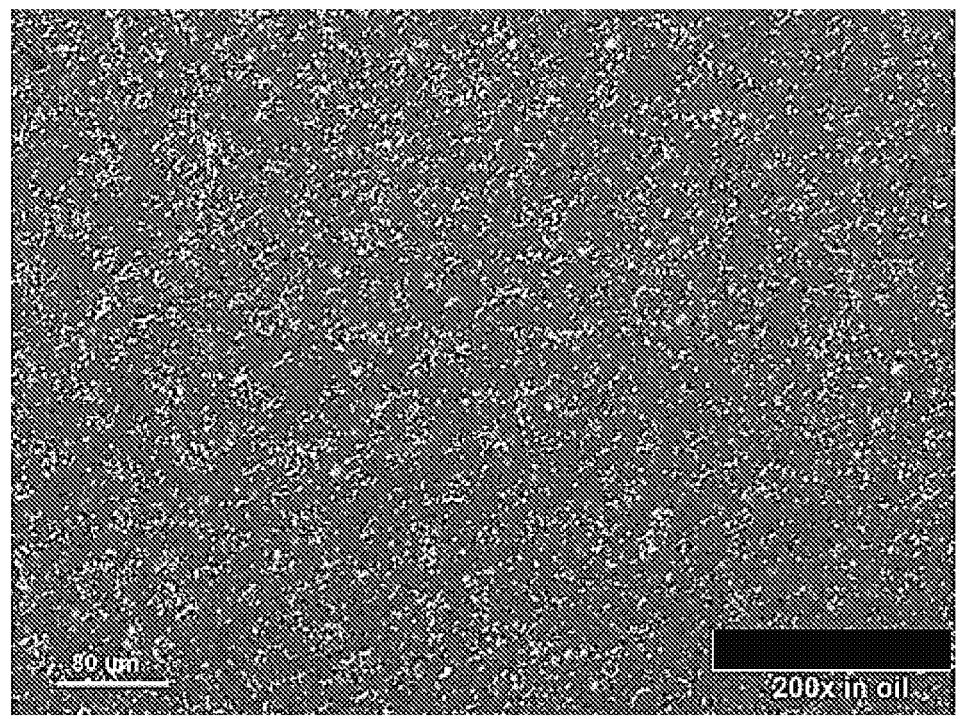
FIG. 4D is a PLM image of Compound 1 Form II as discussed in Example 4.
Figure 4E:
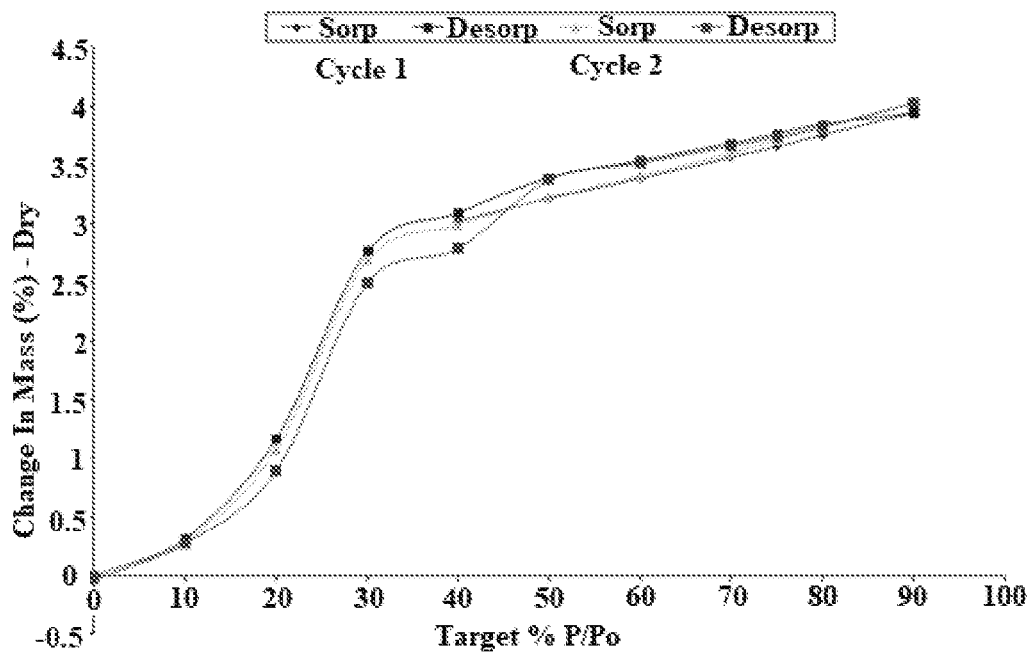
FIG. 4E is a DVS isotherm plot of Compound 1 Form II as discussed in Example 4. The x-axis is target $P/P_o$ measured in percent and the y-axis is change in mass measured in percent.

In one embodiment, Compound 1 Form II is characterized by a PXRD pattern in or substantially similar to that set forth in FIG. 4C. In one embodiment, Compound 1 Form II is characterized by a PXRD pattern comprising a) 2θ values including at least or selected from 5.1, 7.8, 13.5, 14.0, 15.4, 15.6, 18.6, 20.5, 20.7, and 23.4° 2θ;
b) at least two, three, or four 2θ values selected from 5.1, 7.8, 13.5, 14.0, 15.4, 15.6, 18.6, 20.5, 20.7, and 23.4° 2θ;
c) at least five, six, or seven 2θ values selected from 5.1, 7.8, 13.5, 14.0, 15.4, 15.6, 18.6, 20.5, 20.7, and 23.4° 2θ;
d) at least eight or nine 2θ values selected from 5.1, 7.8, 13.5, 14.0, 15.4, 15.6, 18.6, 20.5, 20.7, and 23.4° 2θ;
e) 2θ values including at least or selected from 5.1, 14.0, 15.4, 18.6, and 20.5° 2θ; or
f) at least one 2θ value selected from 5.1, 14.0, 15.4, 18.6, and 20.5° 2θ.

In one embodiment an isolated crystalline Form II of Compound 1 is provided:

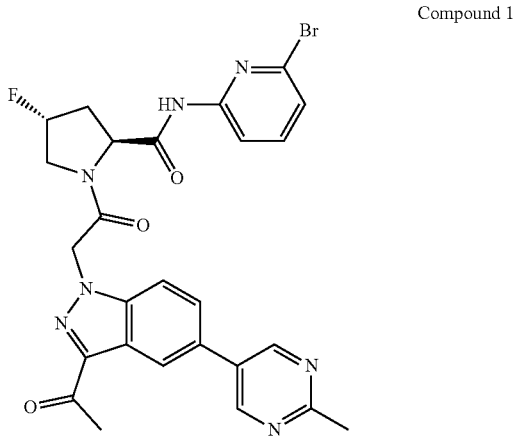 [SMILES: CC(=O)c1nn(CC(=O)N2C[C@H](F)C[C@H]2C(=O)Nc2cccc(Br)n2)c2ccc(-c3cnc(C)nc3)cc12]

Compound 1 characterized by a powder X-ray diffraction (PXRD) pattern comprising at least three 2theta values selected from 5.1±0.2°, 7.8±0.2°, 13.5±0.2°, 14.0±0.2°, 15.4±0.2°, 15.6±0.2°, 18.6±0.2°, 20.5±0.2°, 20.7±0.2°, and 23.4±0.2°.

In another embodiment, the isolated crystalline Form II of claim 1, wherein the PXRD pattern comprises at least four 2theta values selected from 5.1±0.2°, 7.8±0.2°, 13.5±0.2°, 14.0±0.2°, 15.4±0.2°, 15.6±0.2°, 18.6±0.2°, 20.5±0.2°, 20.7±0.2°, and 23.4±0.2° is provided.

In one embodiment, Compound 1 Form II is characterized by a PXRD pattern comprising
a) 2θ values including at least or selected from 5.1, 7.8, 13.5, 14.0, 15.4, 15.6, 18.6, 20.5, 20.7, and 23.4+/−0.2° 2θ;
b) at least two, three, or four 2θ values selected from 5.1, 7.8, 13.5, 14.0, 15.4, 15.6, 18.6, 20.5, 20.7, and 23.4+/−0.2° 2θ;
c) at least five, six, or seven 2θ values selected from 5.1, 7.8, 13.5, 14.0, 15.4, 15.6, 18.6, 20.5, 20.7, and 23.4+/−0.2° 2θ;
d) at least eight or nine 2θ values selected from 5.1, 7.8, 13.5, 14.0, 15.4, 15.6, 18.6, 20.5, 20.7, and 23.4+/−0.2° 2θ;
e) 2θ values including at least or selected from 5.1, 14.0, 15.4, 18.6, and 20.5° 2θ; or
f) at least one 2θ value selected from 5.1, 14.0, 15.4, 18.6, and 20.5° 2θ.

The plus-minus notation "+/−0.2° 2θ" as used to describe morphic forms applies to all 2θ values in the list characterized by +/−0.2° 2θ. For example, in (a) above, 2θ values including at least or selected from 5.1, 7.8, 13.5, 14.0, 15.4, 15.6, 18.6, 20.5, 20.7, and 23.4+/−0.2° 2θ includes the following 2θ values 5.1+/−0.2, 7.8+/−0.2, 13.5+/−0.2, 14.0+/−0.2, 15.4+/−0.2, 15.6+/−0.2, 18.6+/−0.2, 20.5+/−0.2, 20.7+/−0.2, and 23.4+/−0.2.

In one embodiment, isolated Compound 1 Form II is characterized as having approximately a 2-3%, for example, a 2.7% weight loss between 40 and 125° C. in a differential scanning calorimetry analysis.

Compound 1 Form II can be prepared using selective crystallization. The method can be carried out by treating a solution comprising a suitable solvent(s) and Compound 1 optionally in the presence of one or more seeds comprising Compound 1 Form II with conditions that provide for the crystallization of Compound 1 Form II. The selective crystallization can be carried out in any suitable organic solvent. For example, it can be carried out in an aprotic solvent or a mixture thereof. The selective crystallization can be carried out at, for example, by cycling the temperature between 40° C. and 5° C. In one embodiment, the crystallization is conducted while cycling the temperature in a solvent system of heptane:THF. In one embodiment, the crystallization is conducted while cycling the temperature in a solvent system of heptane:methanol:ethanol. In one embodiment, the crystallization is conducted while cycling the temperature in a solvent system of t-BuOH:1,4 dioxane:ethanol:heptane. In one embodiment, the crystallization is conducted while cycling the temperature in a solvent system of cyclohexane:toluene:acetonitrile.

In one embodiment, Compound 1 Form II is produced by recrystallization in a solution of isopropyl alcohol and heptane.

Form III

Isolated morphic Form III of Compound 1 is provided in this invention.

Figure 6A:
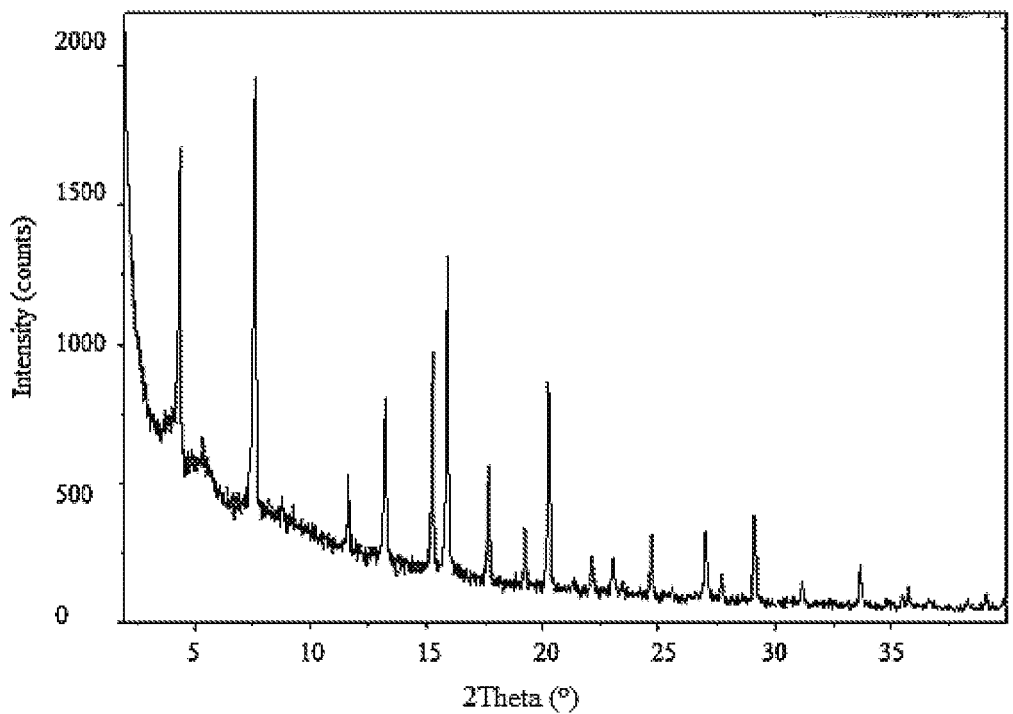
FIG. 6A is a PXRD (powder X-ray diffraction) of Compound 1 Form III as discussed in Example 4. The x-axis is 2Theta measured in degrees and the y-axis is intensity measured in counts.

In one embodiment, Compound 1 Form III is characterized by a PXRD pattern in or substantially similar to that set forth in FIG. 6A. In one embodiment, Compound 1 Form III is characterized by a PXRD pattern comprising
a) 2θ values including at least or selected from 4.4, 7.6, 11.6, 13.2, 15.3, 15.9, 17.7, 20.2, 27.0, and 29.1° 2θ;
b) at least two, three, or four 2θ values selected from 4.4, 7.6, 11.6, 13.2, 15.3, 15.9, 17.7, 20.2, 27.0, and 29.1° 2θ;
c) at least five, six, or seven 2θ values selected from 4.4, 7.6, 11.6, 13.2, 15.3, 15.9, 17.7, 20.2, 27.0, and 29.1° 2θ;
d) at least eight or nine 2θ values selected from 4.4, 7.6, 11.6, 13.2, 15.3, 15.9, 17.7, 20.2, 27.0, and 29.1° 2θ;
e) 2θ values including at least or selected from 4.4, 7.6, 15.3, 15.9, and 20.2° 2θ; or
f) at least one 2θ value selected from 4.4, 7.6, 15.3, 15.9, and 20.2° 2θ.

In one embodiment, Compound 1 Form III is characterized by a PXRD pattern comprising
a) 2θ values including at least or selected from 4.4, 7.6, 11.6, 13.2, 15.3, 15.9, 17.7, 20.2, 27.0, and 29.1+/−0.2° 2θ;
b) at least two, three, or four 2θ values selected from 4.4, 7.6, 11.6, 13.2, 15.3, 15.9, 17.7, 20.2, 27.0, and 29.1+/−0.2° 2θ;
c) at least five, six, or seven 2θ values selected from 4.4, 7.6, 11.6, 13.2, 15.3, 15.9, 17.7, 20.2, 27.0, and 29.1+/−0.2° 2θ;
d) at least eight or nine 2θ values selected from 4.4, 7.6, 11.6, 13.2, 15.3, 15.9, 17.7, 20.2, 27.0, and 29.1+/−0.2° 2θ;

e) 2θ values including at least or selected from 4.4, 7.6, 15.3, 15.9, and 20.2° 2θ; or f) at least one 2θ value selected from 4.4, 7.6, 15.3, 15.9, and 20.2+/−0.2° 2θ.

In one embodiment, isolated Compound 1 Form III is characterized as having a 4.0% weight loss between 40 and 125° C. in a differential scanning calorimetry analysis.

Compound 1 Form III can be prepared using selective crystallization. The method can be carried out by treating a solution comprising a suitable solvent(s) and Compound 1 optionally in the presence of one or more seeds comprising Compound 1 Form III with conditions that provide for the crystallization of Compound 1 Form III. The selective crystallization can be carried out in any suitable organic solvent. For example, it can be carried out in an aprotic solvent or a mixture thereof. The selective crystallization can be carried out at, for example, by cycling the temperature between 40° C. and 5° C. In one embodiment, the crystallization is conducted in a solvent system of heptane and ethanol while cycling the temperature between 40° C. and 5° C.

Form V

Isolated morphic Form V of Compound 1 is provided in this invention.

Figure 8A:
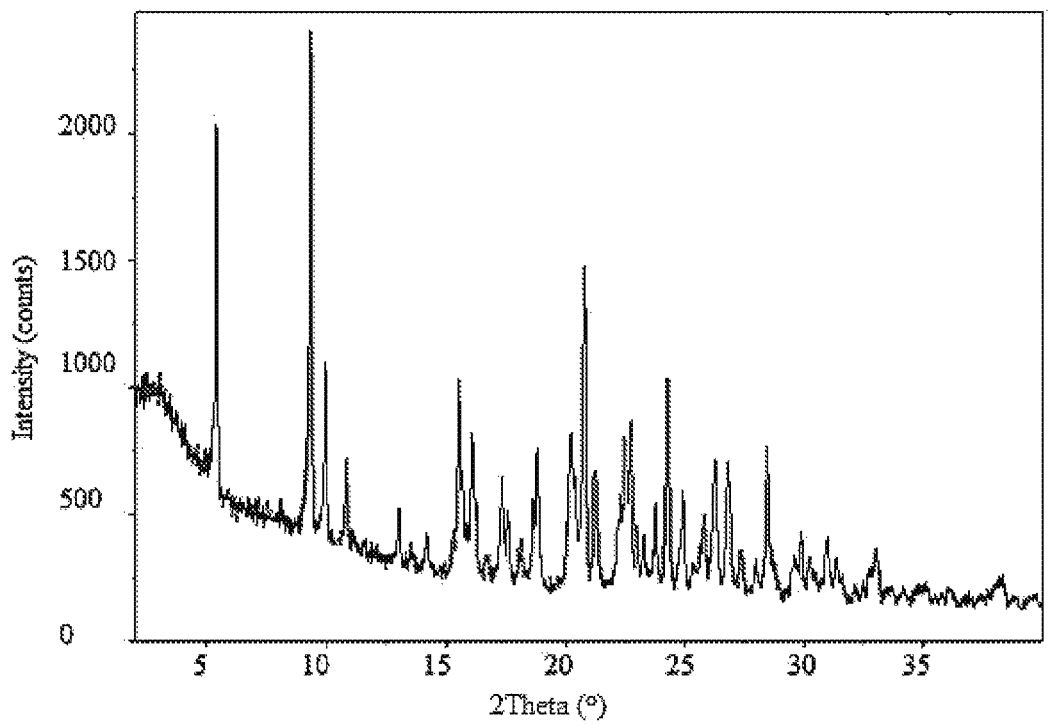
FIG. 8A is a PXRD (powder X-ray diffraction) of Compound 1 Form V as discussed in Example 4. The x-axis is 2Theta measured in degrees and the y-axis is intensity measured in counts.

In one embodiment, Compound 1 Form V is characterized by a PXRD pattern in or substantially similar to that set forth in FIG. 8A. In one embodiment, Compound 1 Form V is characterized by a PXRD pattern comprising a) 2θ values including or selected from 5.4, 9.4, 10.0, 15.6, 18.8, 20.3, 20.8, 22.7, 24.3, and 28.4° 2θ;

b) at least two, three, or four 2θ values selected from 5.4, 9.4, 10.0, 15.6, 18.8, 20.3, 20.8, 22.7, 24.3, and 28.4° 2θ;

c) at least five, six, or seven 2θ values selected from 5.4, 9.4, 10.0, 15.6, 18.8, 20.3, 20.8, 22.7, 24.3, and 28.4° 2θ;

d) at least eight or nine 2θ values selected from 5.4, 9.4, 10.0, 15.6, 18.8, 20.3, 20.8, 22.7, 24.3, and 28.4° 2θ;

e) 2θ values including or selected from 5.4, 9.4, 15.6, 20.8, and 24.3° 2θ; or f) at least one 2θ value selected from 5.4, 9.4, 15.6, 20.8, and 24.3° 2θ.

In one embodiment, Compound 1 Form V is characterized by a PXRD pattern comprising a) 2θ values including or selected from 5.4, 9.4, 10.0, 15.6, 18.8, 20.3, 20.8, 22.7, 24.3, and 28.4+/−0.2° 2θ;

b) at least two, three, or four 2θ values selected from 5.4, 9.4, 10.0, 15.6, 18.8, 20.3, 20.8, 22.7, 24.3, and 28.4+/−0.2° 2θ;

c) at least five, six, or seven 2θ values selected from 5.4, 9.4, 10.0, 15.6, 18.8, 20.3, 20.8, 22.7, 24.3, and 28.4+/−0.2° 2θ;

d) at least eight or nine 2θ values selected from 5.4, 9.4, 10.0, 15.6, 18.8, 20.3, 20.8, 22.7, 24.3, and 28.4+/−0.2° 2θ;

e) 2θ values including or selected from 5.4, 9.4, 15.6, 20.8, and 24.3+/−0.2° 2θ; or f) at least one 2θ value selected from 5.4, 9.4, 15.6, 20.8, and 24.3+/−0.2° 2θ.

In one embodiment, isolated Compound 1 Form V is characterized as having a broad endotherm at 62.3° C. in a differential scanning calorimetry analysis.

Compound 1 Form V can be prepared using selective crystallization. The method can be carried out by treating a solution comprising a suitable solvent(s) and Compound 1 optionally in the presence of one or more seeds comprising Compound 1 Form V with conditions that provide for the crystallization of Compound 1 Form V. The selective crystallization can be carried out in any suitable organic solvent. For example, it can be carried out in an aprotic solvent or a mixture thereof. The selective crystallization can be carried out at, for example, by cycling the temperature between 40° C. and 5° C. In one embodiment, the crystallization is conducted in a solvent system of methanol and 10% (vol) water at approximately 25° C.

Compound 2

Polymorph studies of Compound 2 resulted in the discovery of Form 1. Compound 2 Form I is characterized by the XRPD pattern shown in FIG. 13.

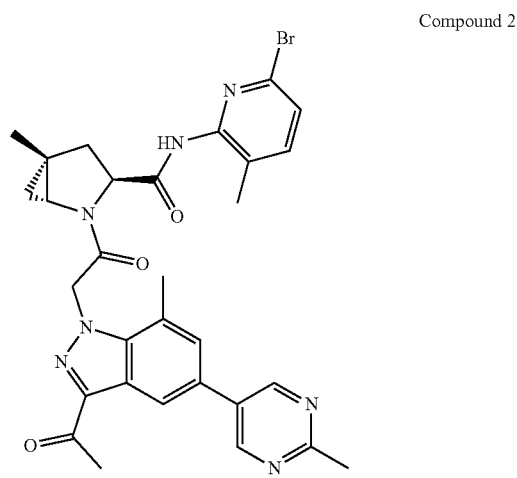

Compound 2

Form I

Isolated morphic Form I of Compound 2 is provided in this invention.

Figure 13:
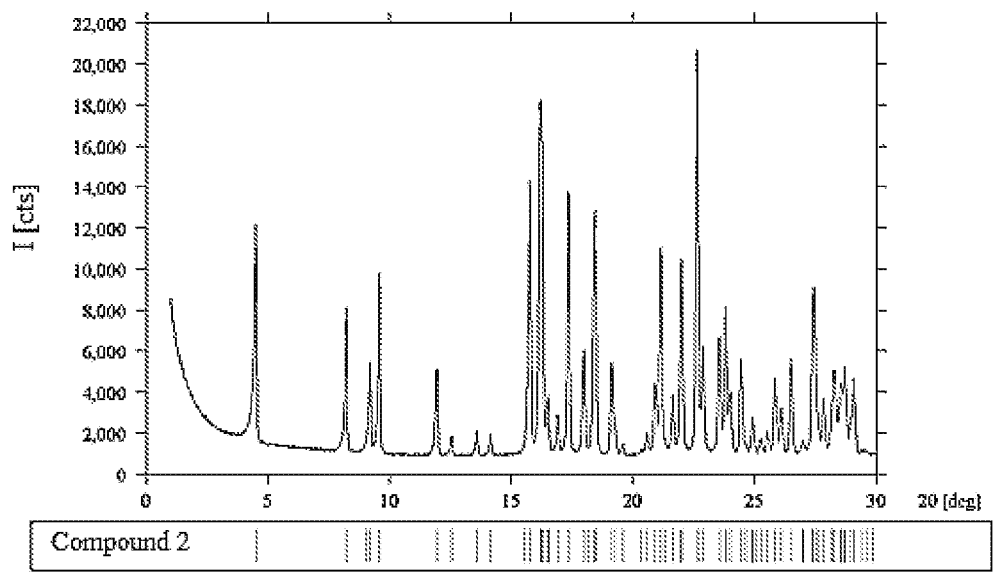
FIG. 13 is XRPD (X-ray powder diffraction) of Compound 2 Form I as discussed in Example 8. The x-axis is 2Theta measured in degrees and the y-axis is intensity measured in counts.

In one embodiment, Form I is characterized by a XRPD pattern in or substantially similar to that set forth in FIG. 13. In one embodiment, Compound 2 Form I is characterized by a XRPD pattern comprising a) 2θ values including at least or selected from 4.5, 8.2, 9.2, 9.6, 11.9, 15.8, 16.2, 17.4, 18.0, 18.4, 21.1, 22.0, 22.6, 23.8 and 27.4+/−0.2° 2θ;

b) at least two, three, or four 2θ values selected from 4.5, 8.2, 9.2, 9.6, 11.9, 15.8, 16.2, 17.4, 18.0, 18.4, 21.1, 22.0, 22.6, 23.8 and 27.4+/−0.2° 2θ;

c) at least five, six, or seven 2θ values selected from 4.5, 8.2, 9.2, 9.6, 11.9, 15.8, 16.2, 17.4, 18.0, 18.4, 21.1, 22.0, 22.6, 23.8 and 27.4+/−0.2° 2θ;

d) at least eight or nine 2θ values selected from 4.5, 8.2, 9.2, 9.6, 11.9, 15.8, 16.2, 17.4, 18.0, 18.4, 21.1, 22.0, 22.6, 23.8 and 27.4+/−0.2° 2θ;

e) 2θ values including at least or selected from 15.8, 16.2, 17.4, 18.4, and 22.6+/−0.2° 2θ; or f) at least one 2θ value selected from 15.8, 16.2, 17.4, 18.4, and 22.6+/−0.2° 2θ.

In one embodiment, isolated Compound 2 Form I is characterized as having a weak exothermic feature at approximately 118° C. and a sharp endotherm with an onset of approximately 242° C. in a differential scanning calorimetry analysis. In one embodiment, isolated Compound 2 Form I is characterized as melting between 251° C. and 263° C. during hot stage microscopy.

Form I can be prepared using selective crystallization. The method can be carried out by treating a solution comprising a suitable solvent(s) and Compound 2 optionally in the presence of one or more seeds comprising Form I to conditions that provide for the crystallization of Form I. The selective crystallization can be carried out in any organic suitable solvent. For example, it can be carried out in an aprotic solvent or a mixture thereof. The selective crystallization can be carried out at, for example, by cycling the temperature between 40° C. and 5° C.

The present invention includes at least the following embodiments of Compound 2 Form I:

a) an isolated crystalline Form I of Compound 2 characterized by an XRPD pattern comprising at least three 2theta values selected from 4.5±0.2°, 8.2±0.2°, 9.2±0.2°, 9.6±0.2°, 11.9±0.2°, 15.8±0.2°, 16.2±0.2°, 17.4±0.2°, 18.0±0.2°, 18.4±0.2°, 21.1±0.2°, 22.0±0.2°, 22.6±0.2°, 23.8±0.2° and 27.4±0.2°;

b) the isolated crystalline Form I of Compound 2 of embodiment (a) characterized by an XRPD pattern comprising at least four 2theta values selected from 4.5±0.2°, 8.2±0.2°, 9.2±0.2°, 9.6±0.2°, 11.9±0.2°, 15.8±0.2°, 16.2±0.2°, 17.4±0.2°, 18.0±0.2°, 18.4±0.2°, 21.1±0.2°, 22.0±0.2°, 22.6±0.2°, 23.8±0.2° and 27.4±0.2°;

c) the isolated crystalline Form I of Compound 2 of embodiment (a) characterized by an XRPD pattern comprising at least five 2theta values selected from 4.5±0.2°, 8.2±0.2°, 9.2±0.2°, 9.6±0.2°, 11.9±0.2°, 15.8±0.2°, 16.2±0.2°, 17.4±0.2°, 18.0±0.2°, 18.4±0.2°, 21.1±0.2°, 22.0±0.2°, 22.6±0.2°, 23.8±0.2° and 27.4±0.2°;

d) the isolated crystalline Form I of Compound 2 of embodiment (a) characterized by an XRPD pattern comprising at least six 2theta values selected from 4.5±0.2°, 8.2±0.2°, 9.2±0.2°, 9.6±0.2°, 11.9±0.2°, 15.8±0.2°, 16.2±0.2°, 17.4±0.2°, 18.0±0.2°, 18.4±0.2°, 21.1±0.2°, 22.0±0.2°, 22.6±0.2°, 23.8±0.2° and 27.4±0.2°;

e) the isolated crystalline Form I of Compound 2 of embodiment (a) characterized by an XRPD pattern comprising at least seven 2theta values selected from 4.5±0.2°, 8.2±0.2°, 9.2±0.2°, 9.6±0.2°, 11.9±0.2°, 15.8±0.2°, 16.2±0.2°, 17.4±0.2°, 18.0±0.2°, 18.4±0.2°, 21.1±0.2°, 22.0±0.2°, 22.6±0.2°, 23.8±0.2° and 27.4±0.2°;

f) the isolated crystalline Form I of Compound 2 of embodiment (a) characterized by an XRPD pattern comprising at least eight 2theta values selected from 4.5±0.2°, 8.2±0.2°, 9.2±0.2°, 9.6±0.2°, 11.9±0.2°, 15.8±0.2°, 16.2±0.2°, 17.4±0.2°, 18.0±0.2°, 18.4±0.2°, 21.1±0.2°, 22.0±0.2°, 22.6±0.2°, 23.8±0.2° and 27.4±0.2°;

g) the isolated crystalline Form I of Compound 2 of embodiment (a) characterized by an XRPD pattern comprising at least nine 2theta values selected from 4.5±0.2°, 8.2±0.2°, 9.2±0.2°, 9.6±0.2°, 11.9±0.2°, 15.8±0.2°, 16.2±0.2°, 17.4±0.2°, 18.0±0.2°, 18.4±0.2°, 21.1±0.2°, 22.0±0.2°, 22.6±0.2°, 23.8±0.2° and 27.4±0.2°;

h) the isolated crystalline Form I of Compound 2 of embodiment (a) characterized by an XRPD pattern comprising the 2theta values selected from 4.5±0.2°, 8.2±0.2°, 9.2±0.2°, 9.6±0.2°, 11.9±0.2°, 15.8±0.2°, 16.2±0.2°, 17.4±0.2°, 18.0±0.2°, 18.4±0.2°, 21.1±0.2°, 22.0±0.2°, 22.6±0.2°, 23.8±0.2° and 27.4±0.2°;

i) the isolated crystalline Form I of Compound 2 of any one of embodiments (a)-(g) characterized by an XRPD pattern comprising at least the 2theta value of 22.6±0.2°;

j) the isolated crystalline Form I of Compound 2 of any one of embodiments (a)-(g) characterized by an XRPD pattern comprising at least the 2theta value of 16.2±0.2°;

k) the isolated crystalline Form I of Compound 2 of any one of embodiments (a)-(g) characterized by an XRPD pattern comprising at least the 2theta value of 15.8±0.2°;

l) the isolated crystalline Form I of Compound 2 of any one of embodiments (a)-(k) wherein the XRPD pattern has the characteristic 2θ values of FIG. 13;

m) the isolated crystalline Form I of Compound 2 of any one of embodiments (a)-(l) that has a differential scanning calorimetry (DSC) onset endotherm of about 242° C.;

n) the isolated crystalline Form I of Compound 2 of any one of embodiments (a)-(l) that has a differential scanning calorimetry (D S C) exotherm of about 118° C.;

o) a pharmaceutical composition comprising the isolated crystalline Form I of Compound 2 of any one of embodiments (a)-(n) in a pharmaceutically acceptable excipient for solid dosage delivery;

p) a method of the treatment of a Complement Factor D mediated disorder comprising administering to a subject in need thereof a therapeutically effective amount of the isolated crystalline Form I of Compound 2 or a pharmaceutical composition thereof according to any one of embodiments (a)-(n), optionally in a pharmaceutically acceptable excipient for solid dosage delivery;

q) the method of embodiment of (p) wherein the subject is a human;

r) the isolated crystalline Form I of Compound 2 of any one of embodiments (a)-(n), optionally in a pharmaceutically acceptable excipient for solid dosage delivery, for use to treat a Complement Factor D mediated disorder in a subject in need thereof;

s) the isolated crystalline Form I Compound 2 of embodiment (r), wherein the subject is a human;

t) the use of the isolated crystalline Form I of Compound 2 or a pharmaceutical composition thereof of any of embodiments (a)-(n), optionally in a pharmaceutically acceptable excipient for solid dosage delivery, in the manufacture of a medicament for the treatment of a Complement Factor D mediated disorder in a subject in need thereof;

u) the use of embodiment (t) wherein the subject is a human.

Chemical Description and Terminology

Compounds are described using standard nomenclature. Unless defined otherwise, all technical and scientific terms used herein have the same meaning as is commonly understood by one of skill in the art to which this invention belongs.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in any suitable order unless otherwise indicated herein or otherwise clearly contradicted by context. The use of any and all examples, or exemplary language (e.g., "such as"), is intended merely for illustration and does not pose a limitation on the scope of the invention unless otherwise claimed.

"Deuteration" and "deuterated" means that a hydrogen is replaced by a deuterium such that the deuterium exists over natural abundance and is thus "enriched". An enrichment of 50% means that rather than hydrogen at the specified position the deuterium content is 50%. For clarity, it is confirmed that the term "enriched" as used herein does not mean percentage enriched over natural abundance. In other embodiments, there will be at least 80%, at least 90%, or at least 95% deuterium enrichment at the specified deuterated position or positions. In other embodiments there will be at least 96%, at least 97%, at least 98%, or at least 99% deuterium enrichment at the specified deuterated position or positions indicated. In the absence of indication to the contrary, the enrichment of deuterium in the specified position of the compound described herein is at least 90%.

A "dosage form" means a unit of administration of an active agent. Non-limiting examples of dosage forms include tablets, capsules, gel caps, injections, suspensions, liquids, intravenous fluids, emulsions, creams, ointments, suppositories, inhalable forms, transdermal forms, and the like.

"Pharmaceutical compositions" are compositions comprising at least one active agent, such as a compound or salt of one of the active compounds disclosed herein, and at least one other substance, such as a carrier. Pharmaceutical compositions optionally contain more than one active agent. "Pharmaceutical combinations" or "combination therapy" refers to the administration of at least two active agents, and in one embodiment, three or four or more active agents which may be combined in a single dosage form or provided together in separate dosage forms optionally with instructions that the active agents are to be used together to treat a disorder.

The term "carrier" means a diluent, excipient, or vehicle with which a morphic form is provided.

A "pharmaceutically acceptable excipient" means an excipient that is useful in preparing a pharmaceutical composition/combination that is generally safe, is sufficiently non-toxic, and neither biologically nor otherwise undesirable. A "pharmaceutically acceptable excipient" as used in the present application includes both one and more than one such excipient.

A "patient" or "host" is a human or non-human animal, including, but not limited to, simian, avian, feline, canine, bovine, equine or porcine in need of medical treatment. Medical treatment can include treatment of an existing condition, such as a disease or disorder, or a prophylactic or diagnostic treatment. In a particular embodiment, the patient or host is a human patient. In an alternative embodiment, the patient such as a host is treated to prevent a disorder or disease described herein.

The term "isolated" as used herein refers to the material in substantially pure form. An isolated compound does not have another component that materially affects the properties of the compound. In particular embodiments, an isolated form is at least 60, 70, 80, 90, 95, 98 or 99% pure.

Pharmaceutical Preparations

The isolated morphic forms described herein can be administered in an effective amount to a host to treat any of the disorders described herein using any suitable approach which achieves the desired therapeutic result. The amount and timing of the isolated morphic forms administered will, of course, be dependent on the host being treated, the instructions of the supervising medical specialist, on the time course of the exposure, on the manner of administration, on the pharmacokinetic properties of the particular active compound, and on the judgment of the prescribing physician. Thus, because of host to host variability, the dosages given below are a guideline and the physician can titrate doses of the compound to achieve the treatment that the physician considers appropriate for the host. In considering the degree of treatment desired, the physician can balance a variety of factors such as age and weight of the host, presence of preexisting disease, as well as presence of other diseases.

An effective amount of a morphic form as described herein, or the morphic form described herein in combination or alternation with, or preceded by, concomitant with or followed by another active agent, can be used in an amount sufficient to (a) inhibit the progression of a disorder mediated by the complement pathway, including an inflammatory, immune, including an autoimmune, disorder or complement Factor D related disorder; (b) cause a regression of an inflammatory, immune, including an autoimmune, disorder or complement Factor D related disorder; (c) cause a cure of an inflammatory, immune, including an autoimmune, disorder or complement Factor D related disorder; or inhibit or prevent the development of an inflammatory, immune, including an autoimmune, disorder or complement Factor D related disorder. Accordingly, an effective amount of the morphic form or composition described herein will provide a sufficient amount of the active agent when administered to a patient to provide a clinical benefit.

The pharmaceutical composition may be formulated as any pharmaceutically useful form, e.g., a pill, a capsule, a tablet, a transdermal patch, a subcutaneous patch, a dry powder, an inhalation formulation, in a medical device, suppository, buccal, or sublingual formulation. Some dosage forms, such as tablets and capsules, are subdivided into suitably sized unit doses containing appropriate quantities of the active components, e.g., an effective amount to achieve the desired purpose.

The therapeutically effective dosage of the morphic forms described herein will be determined by the health care practitioner depending on the condition, size and age of the patient as well as the route of delivery. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of the active compound and optionally from about 0.1 mg to about 2000 mg, from about 10 mg to about 1000 mg, from about 100 mg to about 800 mg, or from about 200 mg to about 600 mg of an additional active agent in a unit dosage form. Examples are dosage forms with at least about 0.5, 1, 1.5, 2, 2.5, 3, 3.5, 4, 4.5, 5, 10, 15, 20, 25, 50, 75, 100, 150, 200, 250, 300, 350, 400, 450, 500, 550, 600, 650, 700, 750, 800, 900, 1000, 1100, 1200, 1250, 1300, 1400, 1500, or 1600 mg of active compound. In one embodiment, the dosage form has at least about 1 mg, 5 mg, 10 mg, 25 mg, 50 mg, 75 mg, 100 mg, 200 mg, 400 mg, 500 mg, 600 mg, 1000 mg, 1200 mg, or 1600 mg of active compound. The dosage form can be administered, for example, once a day (q.d.), twice a day (b.i.d.), three times a day (t.i.d.), four times a day (q.i.d.), once every other day (Q2d), once every third day (Q3d), as needed, or any dosage schedule that provides treatment of a disorder described herein.

The isolated morphic forms disclosed herein or used as described herein may be administered orally, topically, parenterally, by inhalation or spray, sublingually, via implant, including ocular implant, transdermally, via buccal administration, rectally, intramuscular, inhalation, intra-aortal, intracranial, subdermal, intraperitioneal, subcutaneous, transnasal, sublingual, or rectal or by other means, in dosage unit formulations containing conventional pharmaceutically acceptable carriers.

In accordance with the presently disclosed methods, an oral dosage form for administration can be in any desired form in which the morphic form is stable as a solid. In certain embodiments, the isolated morphic form is delivered in a solid microparticle or nanoparticle. When administered through inhalation the isolated morphic form may be in the form of a plurality of solid particles or droplets having any desired particle size, and for example, from about 0.01, 0.1 or 0.5 to about 5, 10, 20 or more microns, and optionally from about 1 to about 2 microns. The isolated morphic forms as disclosed in the present invention have good pharmacokinetic and pharmacodynamics properties, for instance when administered by the oral routes.

The pharmaceutical formulations can comprise the isolated morphic forms described herein, in any pharmaceutically acceptable carrier.

In one embodiment a morphic form as described herein is used to create a spray dried dispersion (SDD) that is administered to a patient in need thereof. In this method, a morphic form is dissolved in an organic solvent such as acetone, methylene chloride, or other organic solvent. The solution is pumped through a micronizing nozzle driven by a flow of compressed gas, and the resulting aerosol is suspended in a heated cyclone of air, allowing the solvent to evaporate from the micro droplets, forming particles. Microparticles and nanoparticles can be obtained using this method.

In one embodiment a morphic form as described herein is administered to a patient in need thereof as a spray dried dispersion (SDD). In another embodiment the present invention provides a spray dried dispersion (SDD) comprising a morphic form of the present invention and one or more pharmaceutically acceptable excipients as defined herein. In another embodiment the SDD comprises a morphic form of the present invention and an additional therapeutic agent. In a further embodiment the SDI comprises a morphic form of the present invention, an additional therapeutic agent, and one or more pharmaceutically acceptable excipients. In another embodiment any of the described spray dried dispersions can be coated to form a coated tablet. In an alternative embodiment the spray dried dispersion is formulated into a tablet but is uncoated.

Particles can be formed from the morphic form as described herein using a phase inversion method. In this method, the morphic form is dissolved in a suitable solvent, and the solution is poured into a strong non-solvent for the compound to spontaneously produce, under favorable conditions, microparticles or nanoparticles. The method can be used to produce nanoparticles in a wide range of sizes, including, for example, from nanoparticles to microparticles, typically possessing a narrow particle size distribution.

In an alternative embodiment, the morphic form is subjected to a milling process, included but not limited to, hand-milling, rotor-milling, ball-milling, and jet-milling to obtain microparticles and nanoparticles.

In one embodiment, the particle is between about 0.1 nm to about 10000 nm, between about 1 nm to about 1000 nm, between about 10 nm and 1000 nm, between about 1 and 100 nm, between about 1 and 10 nm, between about 1 and 50 nm, between about 100 nm and 800 nm, between about 400 nm and 600 nm, or about 500 nm. In one embodiment, the micro-particles are no more than about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidents, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

Depending on the intended mode of administration, the pharmaceutical compositions can be in the form of solid form or a semi-solid dosage form that the isolated morphic form is stable in, such as, for example, tablets, suppositories, pills, capsules, powders, or the like, preferably in unit dosage form suitable for single administration of a precise dosage. The compositions will include an effective amount of the selected drug in combination with a pharmaceutically acceptable carrier and, in addition, can include other pharmaceutical agents, adjuvants, diluents, buffers, and the like.

Thus, the compositions of the disclosure can be administered as pharmaceutical formulations including those suitable for oral (including buccal and sub-lingual), rectal, nasal, topical, pulmonary, vaginal administration or in a form suitable for administration by inhalation or insufflation. The preferred manner of administration is oral using a convenient daily dosage regimen which can be adjusted according to the degree of affliction. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like.

In yet another embodiment is the use of permeation enhancer excipients including polymers such as: polycations (chitosan and its quaternary ammonium derivatives, poly-L-arginine, aminated gelatin); polyanions (N-carboxymethyl chitosan, poly-acrylic acid); and, thiolated polymers (carboxymethyl cellulose-cysteine, polycarbophil-cysteine, chitosan-thiobutylamidine, chitosan-thioglycolic acid, chitosan-glutathione conjugates).

For oral administration, the composition will generally take the form of a tablet or capsule. Tablets and capsules are preferred oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

In addition to the active compounds or their salts, the pharmaceutical formulations can contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the formulations can contain antimicrobial preservatives. Useful antimicrobial preservatives include methylparaben, propylparaben, and benzyl alcohol. An antimicrobial preservative is typically employed when the formulations is placed in a vial designed for multi-dose use. The pharmaceutical formulations described herein can be lyophilized using techniques well known in the art.

For oral administration a pharmaceutical composition can take the form of a tablet, pill, capsule, powder, and the like. Tablets containing various excipients such as sodium citrate, calcium carbonate and calcium phosphate may be employed along with various disintegrants such as starch (e.g., potato or tapioca starch) and certain complex silicates, together with binding agents such as polyvinylpyrrolidone, sucrose, gelatin and acacia. Additionally, lubricating agents such as magnesium stearate, sodium lauryl sulfate, and talc are often very useful for tableting purposes. Solid compositions of a similar type may be employed as fillers in soft and hard-filled gelatin capsules.

Pharmaceutical formulations also are provided which provide a controlled release of a compound described herein, including through the use of a degradable polymer, as known in the art.

In one embodiment the additional therapeutic agent described in the Combination Section below is administered as a pharmaceutically acceptable salt, for example, a salt described below.

Thus, the term "salts" refers to the relatively non-toxic, inorganic and organic acid addition salts of the presently disclosed compounds. These salts can be prepared during the final isolation and purification of the compounds or by separately reacting the purified compound in its free base form with a suitable organic or inorganic acid and isolating the salt thus formed. Basic compounds are capable of forming a wide variety of different salts with various inorganic and organic acids. Acid addition salts of the basic compounds are prepared by contacting the free base form with a sufficient amount of the desired acid to produce the salt in the conventional manner. The free base form can be regenerated by contacting the salt form with a base and isolating the free base in the conventional manner. The free base forms may differ from their respective salt forms in certain physical properties such as solubility in polar solvents. Pharmaceutically acceptable base addition salts may be formed with metals or amines, such as alkali and alkaline earth metal hydroxides, or of organic amines. Examples of metals used as cations, include, but are not limited to, sodium, potassium, magnesium, calcium, and the like. Examples of suitable amines include, but are not limited to, N,N'-dibenzylethylenediamine, chloroprocaine, choline, diethanolamine, ethylenediamine, N-methylglucamine, and procaine. The base addition salts of acidic compounds are prepared by contacting the free acid form with a sufficient amount of the desired base to produce the salt in the conventional manner. The free acid form can be regenerated by contacting the salt form with an acid and isolating the free acid in a conventional manner. The free acid forms may differ from their respective salt forms somewhat in certain physical properties such as solubility in polar solvents.

Salts can be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts can also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts can include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See, for example, Berge et al., J. Pharm. Sci., 1977, 66, 1-19, which is incorporated herein by reference.

Formulations suitable for rectal administration are typically presented as unit dose suppositories. These may be prepared by admixing the active disclosed compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil, which maintain the stability of the isolated morphic form. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. In one embodiment, microneedle patches or devices are provided for delivery of drugs across or into biological tissue, particularly the skin. The microneedle patches or devices permit drug delivery at clinically relevant rates across or into skin or other tissue barriers, with minimal or no damage, pain, or irritation to the tissue.

Formulations suitable for administration to the lungs can be delivered by a wide range of passive breath driven and active power driven single/-multiple dose dry powder inhalers (DPI). The devices most commonly used for respiratory delivery include nebulizers, metered-dose inhalers, and dry powder inhalers. Several types of nebulizers are available, including jet nebulizers, ultrasonic nebulizers, and vibrating mesh nebulizers. Selection of a suitable lung delivery device depends on parameters, such as nature of the drug and its formulation, the site of action, and pathophysiology of the lung.

Uses of Active Compounds for Treatment of Selected Disorders

In one aspect, an effective amount of morphic form or composition as described herein is used to treat a medical disorder which is an inflammatory or immune condition, a disorder mediated by the complement cascade (including a dysfunctional cascade) including a complement factor D-related disorder or alternative complement pathway-related disorder, a disorder or abnormality of a cell that adversely affects the ability of the cell to engage in or respond to normal complement activity, or an undesired complement-mediated response to a medical treatment, such as surgery or other medical procedure or a pharmaceutical or biopharmaceutical drug administration, a blood transfusion, or other allogenic tissue or fluid administration.

In one embodiment, a method for the treatment of C3 glomerulonephritis (C3G) is provided that includes the administration of an effective amount of a morphic form described herein, optionally in a pharmaceutically acceptable composition.

In one embodiment, a method for the treatment of paroxysmal nocturnal hemoglobinuria (PNH) is provided that includes the administration of an effective amount of a morphic form described herein, optionally in a pharmaceutically acceptable composition.

In another embodiment, a method for the treatment of wet or dry age-related macular degeneration (AMD) in a host is provided that includes the administration of an effective amount of a morphic form described herein, optionally in a pharmaceutically acceptable composition.

In another embodiment, a method for the treatment of rheumatoid arthritis in a host is provided that includes the administration of an effective amount of a morphic form described herein, optionally in a pharmaceutically acceptable composition.

In another embodiment, a method for the treatment of multiple sclerosis or amyotrophic lateral sclerosis in a host is provided that includes the administration of an effective amount of a morphic form described herein, optionally in a pharmaceutically acceptable composition.

In another embodiment, a method for the treatment of membranoproliferative glomerulonephritis type II (MPGN II) in a host is provided that includes the administration of an effective amount of a morphic form described herein, optionally in a pharmaceutically acceptable composition.

In another embodiment, a method for the treatment of nonalcoholic steatohepatitis (NASH) in a host is provided that includes the administration of an effective amount of a morphic form described herein, optionally in a pharmaceutically acceptable composition.

In another embodiment, a method for the treatment of fatty liver, liver inflammation, cirrhosis, or liver failure in a host is provided that includes the administration of an effective amount of a morphic form described herein, optionally in a pharmaceutically acceptable composition.

In another embodiment, a method for the treatment of dermatomyositis in a host is provided that includes the administration of an effective amount of a morphic form described herein, optionally in a pharmaceutically acceptable composition.

In another embodiment, a method for the treatment of arthritis or COPD in a host is provided that includes the administration of an effective amount of a morphic form described herein, optionally in a pharmaceutically acceptable composition.

In another embodiment, a method for the treatment of a respiratory disease or a cardiovascular disease in a host is provided that includes the administration of an effective amount of a morphic form described herein, optionally in a pharmaceutically acceptable composition.

In another embodiment, a method for the treatment of atypical or typical hemolytic uremic syndrome in a host is provided that includes the administration of an effective amount of a morphic form described herein, optionally in a pharmaceutically acceptable composition.

In another embodiment, a method for the treatment of membrane proliferative glomerulonephritis or age-related macular degeneration (AMD) in a host is provided that includes the administration of an effective amount of a morphic form described herein, optionally in a pharmaceutically acceptable composition.

In another embodiment, a method for the treatment of type I diabetes or complications thereof in a host is provided that includes the administration of an effective amount of a morphic form described herein, optionally in a pharmaceutically acceptable composition.

The morphic form, optionally in a pharmaceutically acceptable composition, as disclosed herein is also useful for administration in combination (in the same or a different dosage form) or alternation with a second pharmaceutical agent for use in ameliorating or reducing a side effect of the second pharmaceutical agent.

Another embodiment is provided that includes the administration of an effective amount of a morphic form, optionally in a pharmaceutically acceptable composition to a host to treat an ocular, pulmonary, gastrointestinal, or other disorder that can benefit from topical or local delivery.

In other embodiments of the invention, a morphic form provided herein can be used to treat or prevent a disorder in a host mediated by complement factor D, or by an excessive or detrimental amount of the complement-C3 amplification loop of the complement pathway. As examples, the invention includes methods to treat or prevent complement associated disorders that are induced by antibody-antigen interactions, a component of an immune or autoimmune disorder or by ischemic injury. The invention also provides methods to decrease inflammation or an immune response, including an autoimmune response, where mediated or affected by factor D.

In one embodiment, the disorder is selected from fatty liver and conditions stemming from fatty liver, such as nonalcoholic steatohepatitis (NASH), liver inflammation, cirrhosis and liver failure. In one embodiment of the present invention, a method is provided for treating fatty liver disease in a host by administering an effective amount of a morphic form or composition as described herein.

In another embodiment, a morphic form or composition as described herein is used to modulate an immune response prior to or during surgery or other medical procedure. One non-limiting example is use in connection with acute or chronic graft versus host disease, which is a common complication as a result of allogeneic tissue transplant, and can also occur as a result of a blood transfusion.

In one embodiment, the present invention provides a method of treating or preventing dermatomyositis by administering to a subject in need thereof an effective amount of a morphic form or composition as described herein.

In one embodiment, the present invention provides a method of treating or preventing amyotrophic lateral sclerosis by administering to a subject in need thereof an effective amount of a morphic form or composition as described herein.

In one embodiment, the present invention provides a method of treating or preventing abdominal aortic aneurysm, hemodialysis complications, hemolytic anemia, or hemodialysis by administering to a subject in need thereof an effective amount of a morphic form or composition as described herein.

In one embodiment, the present invention provides a method of treating or preventing a C3 glomurenopathy by administering to a subject in need thereof an effective amount of a morphic form or composition as described herein. In one embodiment, the disorder is selected from dense deposit disease (DDD) and C3 glomerulonephritis (C3GN).

In one embodiment, the present invention provides a method of treating or preventing a IC-MPGN by administering to a subject in need thereof an effective amount of a morphic form or composition as described herein.

In one embodiment, the present invention provides a method of treating or preventing a paroxysmal nocturnal hemoglobinuria (PNH) by administering to a subject in need thereof an effective amount of a morphic form or composition as described herein.

In one embodiment, the present invention provides a method of treating or preventing age-related macular degeneration (AMD) by administering to a subject in need thereof an effective amount of a morphic form or composition as described herein.

In one embodiment, the present invention provides a method of treating or preventing rheumatoid arthritis by administering to a subject in need thereof an effective amount of a morphic form or composition as described herein.

In one embodiment, the present invention provides a method of treating or preventing multiple sclerosis by administering to a subject in need thereof an effective amount of a morphic form or composition as described herein.

In one embodiment, the present invention provides a method of treating or preventing myasthenia gravis by administering to a subject in need thereof an effective amount of a morphic form or composition as described herein.

In one embodiment, the present invention provides a method of treating or preventing atypical hemolytic uremic syndrome (aHUS) by administering to a subject in need thereof an effective amount of a morphic form or composition as described herein.

In one embodiment, the present invention provides a method of treating or preventing neuromyelitis optica (NMO) by administering to a subject in need thereof an effective amount of a morphic form or composition as described herein.

In yet another embodiment, the present invention provides a method of treating or preventing a disorder as described below by administering to a subject in need thereof an effective amount of a morphic form or composition as described herein, including: vitritis, sarcoidosis, syphilis, tuberculosis, or Lyme disease; retinal vasculitis, Eales disease, tuberculosis, syphilis, or toxoplasmosis; neuroretinitis, viral retinitis, or acute retinal necrosis; varicella zoster virus, herpes simplex virus, cytomegalovirus, Epstein-Barr virus, lichen planus, or Dengue-associated disease (e.g., hemorraghic Dengue Fever); Masquerade syndrome, contact dermatitis, trauma induced inflammation, UVB induced inflammation, eczema, granuloma annulare, or acne.

In an additional embodiment, the disorder is selected from: acute myocardial infarction, aneurysm, cardiopulmonary bypass, dilated cardiomyopathy, complement activation during cardiopulmonary bypass operations, coronary artery disease, restenosis following stent placement, or percutaneous transluminal coronary angioplasty (PTCA); antibody-mediated transplant rejection, anaphylactic shock, anaphylaxis, allogenic transplant, humoral and vascular transplant rejection, graft dysfunction, graft-versus-host disease, Graves' disease, adverse drug reactions, or chronic graft vasculopathy; allergic bronchopulmonary aspergillosis, allergic neuritis, drug allergy, radiation-induced lung injury, eosinophilic pneumonia, radiographic contrast media allergy, bronchiolitis obliterans, or interstitial pneumonia; parkinsonism-dementia complex, sporadic frontotemporal dementia, frontotemporal dementia with Parkinsonism linked to chromosome 17, frontotemporal lobar degeneration, tangle only dementia, cerebral amyloid angiopathy, cerebrovascular disorder, certain forms of frontotemporal dementia, chronic traumatic encephalopathy (CTE), PD with dementia (PDD), argyrophilic grain dementia, dementia pugilistica, dementia with Lewy Bodies (DLB), or multi-infarct dementia; Creutzfeldt-Jakob disease, Huntington's disease, multifocal motor neuropathy (MMN), prion protein cerebral amyloid angiopathy, polymyositis, postencephalitic parkinsonism, subacute sclerosing panencephalitis, non-Guamanian motor neuron disease with neurofibrillary tangles, neural regeneration, or diffuse neurofibrillary tangles with calcification.

In one embodiment, the disorder is selected from: atopic dermatitis, dermatitis, dermatomyositis bullous pemphigoid, scleroderma, sclerodermatomyositis, psoriatic arthritis, pemphigus vulgaris, Discoid lupus erythematosus, cutaneous lupus, chilblain lupus erythematosus, or lupus erythematosus-lichen planus overlap syndrome; cryoglobulinemic vasculitis, mesenteric/enteric vascular disorder, peripheral vascular disorder, antineutrophil cytoplasm antibody (ANCA)-associated vasculitis (AAV), IL-2 induced vascular leakage syndrome, or immune complex vasculitis; angioedema, low platelets (HELLP) syndrome, sickle cell disease, platelet refractoriness, red cell casts, or typical or infectious hemolytic uremic syndrome (tHUS); hematuria, hemorrhagic shock, drug-induced thrombocytopenia, autoimmune hemolytic anemia (AIHA), azotemia, blood vessel and/or lymph vessel inflammation, rotational atherectomy, or delayed hemolytic transfusion reaction; British type amyloid angiopathy, Buerger's disease, bullous pemphigoid, C1q nephropathy, cancer, or catastrophic antiphospholipid syndrome.

In another embodiment, the disorder is selected from: wet (exudative) AMD, dry (non-exudative) AMD, chorioretinal degeneration, choroidal neovascularization (CNV), choroiditis, loss of RPE function, loss of vision (including loss of visual acuity or visual field), loss of vision from AMD, retinal damage in response to light exposure, retinal degeneration, retinal detachment, retinal dysfunction, retinal neovascularization (RNV), retinopathy of prematurity, pathological myopia, or RPE degeneration; pseudophakic bullous keratopathy, symptomatic macular degeneration related disorder, optic nerve degeneration, photoreceptor degeneration, cone degeneration, loss of photoreceptor cells, pars planitis, scleritis, proliferative vitreoretinopathy, or formation of ocular drusen; chronic urticaria, Churg-Strauss syndrome, cold agglutinin disease (CAD), corticobasal degeneration (CBD), cryoglobulinemia, cyclitis, damage of the Bruch's membrane, Degos disease, diabetic angiopathy, elevated liver enzymes, endotoxemia, epidermolysis bullosa, or epidermolysis bullosa acquisita; essential mixed cryoglobulinemia, excessive blood urea nitrogen-BUN, focal segmental glomerulosclerosis, Gerstmann-Straussler-Scheinker disease, giant cell arteritis, gout, Hallervorden-Spatz disease, Hashimoto's thyroiditis, Henoch-Schonlein purpura nephritis, or abnormal urinary sediments; hepatitis, hepatitis A, hepatitis B, hepatitis C or human immunodeficiency virus (HIV), a viral infection more generally, for example selected from Flaviviridae, Retroviruses, Coronaviridae, Poxviridae, Adenoviridae, Herpesviridae, Caliciviridae, Reoviridae, Picornaviridae, Togaviridae, Orthomyxoviridae, Rhabdoviridae, or Hepadnaviridae; *Neisseria meningitidis*, shiga toxin *E. coli*-related hemolytic uremic syndrome (STEC-HUS), hemolytic uremic syndrome (HUS); *Streptococcus*, or poststreptococcal glomerulonephritis.

In a further embodiment, the disorder is selected from: hyperlipidemia, hypertension, hypoalbuminemia, hypobolemic shock, hypocomplementemic urticarial vasculitis syndrome, hypophosphastasis, hypovolemic shock, idiopathic pneumonia syndrome, or idiopathic pulmonary fibrosis; inclusion body myositis, intestinal ischemia, iridocyclitis, iritis, juvenile chronic arthritis, Kawasaki's disease (arteritis), or lipiduria; membranoproliferative glomerulonephritis (MPGN) I, microscopic polyangiitis, mixed cryoglobulinemia, molybdenum cofactor deficiency (MoCD) type A, pancreatitis, panniculitis, Pick's disease, polyarteritis nodosa (PAN), progressive subcortical gliosis, proteinuria, reduced glomerular filtration rate (GFR), or renovascular disorder; multiple organ failure, multiple system atrophy (MSA), myotonic dystrophy, Niemann-Pick disease type C, chronic demyelinating diseases, or progressive supranuclear palsy; spinal cord injury, spinal muscular atrophy, spondyloarthropathies, Reiter's syndrome, spontaneous fetal loss, recurrent fetal loss, pre-eclampsia, synucleinopathy, Takayasu's arteritis, post-partum thyroiditis, thyroiditis, Type I cryoglobulinemia, Type II mixed cryoglobulinemia, Type III mixed cryoglobulinemia, ulcerative colitis, uremia, urticaria, venous gas embolus (VGE), or Wegener's granulomatosis; von Hippel-Lindau disease, histoplasmosis of the eye, hard drusen, soft drusen, pigment clumping, or photoreceptor and/or retinal pigmented epithelia (RPE) loss.

In one embodiment, a morphic form or composition as described herein is useful for treating or preventing a disorder selected from autoimmune oophoritis, endometriosis, autoimmune orchitis, Ord's thyroiditis, autoimmune enteropathy, coeliac disease, Hashimoto's encephalopathy, antiphospholipid syndrome (APLS) (Hughes syndrome), aplastic anemia, autoimmune lymphoproliferative syndrome (Canale-Smith syndrome), autoimmune neutropenia, Evans syndrome, pernicious anemia, pure red cell aplasia, thrombocytopenia, adipose dolorosa (Dercum's disease), adult onset Still's disease, ankylosing spondylitis, CREST syndrome, drug-induced lupus, eosinophilic fasciitis (Shulman's syndrome), Felty syndrome, IgG4-related disease, mixed connective tissue disease (MCTD), palindromic rheumatism (Hench-Rosenberg syndrome), Parry-Romberg syndrome, Parsonage-Turner syndrome, relapsing polychondritis (Meyenburg-Altherr-Uehlinger syndrome), retroperitoneal fibrosis, rheumatic fever, Schnitzler syndrome, fibromyalgia, neuromyotonia (Isaac's disease), paraneoplastic degeneration, autoimmune inner ear disease, Meniere's disease, interstitial cystitis, autoimmune pancreatitis, zika virus-related disorders, chikungunya virus-related disorders, subacute bacterial endocarditis (SBE), IgA nephropathy, IgA vasculitis, polymyalgia rheumatic, rheumatoid vasculitis, alopecia areata, autoimmune progesterone dermatitis, dermatitis herpetiformis, erythema nodosum, gestational pemphigoid, hidradenitis suppurativa, lichen sclerosus, linear IgA disease (LAD), morphea, myositis, pityriasis lichenoides et varioliformis acuta, vitiligo post-myocardial infarction syndrome (Dressler's syndrome), post-pericardiotomy syndrome, autoimmune retinopathy, Cogan syndrome, Graves opthalmopathy, ligneous conjunctivitis, Mooren's ulcer, opsoclonus myoclonus syndrome, optic neuritis, retinocochleocerebral vasculopathy (Susac's syndrome), sympathetic opthalmia, Tolosa-Hunt syndrome, interstitial lung disease, antisynthetase syndrome, Addison's disease, autoimmune polyendocrine syndrome (APS) type I, autoimmune polyendocrine syndrome (APS) type II, autoimmune polyendocrine syndrome (APS) type III, disseminated sclerosis (multiple sclerosis, pattern II), rapidly progressing glomerulonephritis (RPGN), juvenile rheumatoid arthritis, enthesitis-related arthritis, reactive arthritis (Reiter's syndrome), autoimmune hepatitis or lupoid hepatitis, primary biliary cirrhosis (PBS), primary sclerosing cholangitis, microscopic colitis, latent lupus (undifferentiated connective tissue disease (UCTD)), acute disseminated encephalomyelitis (ADEM), acute motor axonal neuropathy, anti-n-methyl-D-aspartate receptor encephalitis, Balo concentric sclerosis (Schilders disease), Bickerstaff's encephalitis, chronic inflammatory demyelinating polyneuropathy, idiopathic inflammatory demyelinating disease, Lambert-Eaton mysathenic syndrome, Oshtoran syndrome, pediatric autoimmune neuropsychiatric disorder associated with *Streptococcus* (PANDAS), progressive inflammatory neuropathy, restless leg syndrome, stiff person syndrome, Sydenhem syndrome, transverse myelitis, lupus vasculitis, leukocytoclastic vasculitis, Microscopic Polyangiitis, polymyositis or ischemic-reperfusion injury of the eye.

Examples of eye disorders that may be treated according to the compositions and methods disclosed herein include amoebic keratitis, fungal keratitis, bacterial keratitis, viral keratitis, onchorcercal keratitis, bacterial keratoconjunctivitis, viral keratoconjunctivitis, corneal dystrophic diseases, Fuchs' endothelial dystrophy, Sjogren's syndrome, Stevens-Johnson syndrome, autoimmune dry eye diseases, environmental dry eye diseases, corneal neovascularization diseases, post-corneal transplant rejection prophylaxis and treatment, autoimmune uveitis, infectious uveitis, posterior uveitis (including toxoplasmosis), pan-uveitis, an inflammatory disease of the vitreous or retina, endophthalmitis prophylaxis and treatment, macular edema, macular degeneration, age related macular degeneration, proliferative and non-proliferative diabetic retinopathy, hypertensive retinopathy, an autoimmune disease of the retina, primary and metastatic intraocular melanoma, other intraocular metastatic tumors, open angle glaucoma, closed angle glaucoma, pigmentary glaucoma and combinations thereof.

In a further embodiment, the disorder is selected from glaucoma, diabetic retinopathy, blistering cutaneous diseases (including bullous pemphigoid, pemphigus, and epidermolysis bullosa), ocular cicatrical pemphigoid, uveitis, adult macular degeneration, diabetic retinopa retinitis pigmentosa, macular edema, diabetic macular edema, Behcet's uveitis, multifocal choroiditis, Vogt-Koyangi-Harada syndrome, imtermediate uveitis, birdshot retino-chorioditis, sympathetic ophthalmia, ocular dicatricial pemphigoid, ocular pemphigus, nonartertic ischemic optic neuropathy, postoperative inflammation, and retinal vein occlusion, or central retinal vein occulusion (CVRO).

In some embodiments, complement mediated diseases include ophthalmic diseases (including early or neovascular age-related macular degeneration and geographic atrophy), autoimmune diseases (including arthritis, rheumatoid arthritis), respiratory diseases, cardiovascular diseases. In other embodiments, the compounds of the invention are suitable for use in the treatment of diseases and disorders associated with fatty acid metabolism, including obesity and other metabolic disorders.

Disorders that may be treated or prevented by a morphic form or composition as described herein also include, but are not limited to: hereditary angioedema, capillary leak syndrome, hemolytic uremic syndrome (HUS), neurological disorders, Guillain Barre Syndrome, diseases of the central nervous system and other neurodegenerative conditions, glomerulonephritis (including membrane proliferative glomerulonephritis), SLE nephritis, proliferative nephritis, liver fibrosis, tissue regeneration and neural regeneration, or Barraquer-Simons Syndrome; inflammatory effects of sepsis, systemic inflammatory response syndrome (SIRS), disorders of inappropriate or undesirable complement activation, interleukin-2 induced toxicity during IL-2 therapy, inflammatory disorders, inflammation of autoimmune diseases, system lupus erythematosus (SLE), lupus nephritides, arthritis, immune complex disorders and autoimmune diseases, systemic lupus, or lupus erythematosus; ischemia/reperfusion injury (FR injury), myocardial infarction, myocarditis, post-ischemic reperfusion conditions, balloon angioplasty, atherosclerosis, post-pump syndrome in cardiopulmonary bypass or renal bypass, renal ischemia, mesenteric artery reperfusion after aortic reconstruction, antiphospholipid syndrome, autoimmune heart disease, ischemia-reperfusion injuries, obesity, or diabetes; Alzheimer's dementia, stroke, schizophrenia, traumatic brain injury, trauma, Parkinson's disease, epilepsy, transplant rejection, prevention of fetal loss, biomaterial reactions (e.g. in hemodialysis, inplants), hyperacute allograft rejection, xenograft rejection, transplantation, psoriasis, burn injury, thermal injury including burns or frostbite, or crush injury; asthma, allergy, acute respiratory distress syndrome (ARDS), cystic fibrosis, adult respiratory distress syndrome, dyspnea, hemoptysis, chronic obstructive pulmonary disease (COPD), emphysema, pulmonary embolisms and infarcts, pneumonia, fibrogenic dust diseases, inert dusts and minerals (e.g., silicon, coal dust, beryllium, and asbestos), pulmonary fibrosis, organic dust diseases, chemical injury (due to irritant gases and chemicals, e.g., chlorine, phosgene, sulfur dioxide, hydrogen sulfide, nitrogen dioxide, ammonia, and hydrochloric acid), smoke injury, thermal injury (e.g., burn, freeze), bronchoconstriction, hypersensitivity pneumonitis, parasitic diseases, Goodpasture's Syndrome (anti-glomerular basement membrane nephritis), pulmonary vasculitis, Pauci-immune vasculitis, or immune complex-associated inflammation.

In one embodiment, a method for the treatment of sickle cell in a host is provided that includes the administration of an effective amount of a morphic form or composition as described herein. In one embodiment, a method for the treatment of immunothrombocytopenic purpura (ITP), thrombotic thrombocytopenic purpura (TTP), or idiopathic thrombocytopenic purpura (ITP) in a host is provided that includes the administration of an effective amount of a morphic form or composition as described herein. In one embodiment, a method for the treatment of ANCA-vasculitis in a host is provided that includes the administration of an effective amount of a morphic form or composition as described herein. In one embodiment, a method for the treatment of IgA nephropathy in a host is provided that includes the administration of an effective amount of a morphic form or composition as described herein. In one embodiment, a method for the treatment of rapidly progressing glomerulonephritis (RPGN), in a host is provided that includes the administration of an effective amount of a morphic form or composition as described herein. In one embodiment, a method for the treatment of lupus nephritis, in a host is provided that includes the administration of an effective amount of a morphic form or composition as described herein. In one embodiment, a method for the treatment of hemorraghic dengue fever, in a host is provided that includes the administration of an effective amount of a morphic form or composition as described herein.

In an additional alternative embodiment, a morphic form or composition as described herein is used in the treatment of an autoimmune disorder.

The complement pathway enhances the ability of antibodies and phagocytic cells to clear microbes and damaged cells from the body. It is part of the innate immune system and in healthy individuals is an essential process. Inhibiting the complement pathway will decrease the body's immune system response. Therefore, it is an object of the present invention to treat autoimmune disorders by administering an effective does of a morphic form or composition as described herein to a subject in need thereof.

In one embodiment the autoimmune disorder is caused by activity of the complement system. In one embodiment the autoimmune disorder is caused by activity of the alternative complement pathway. In one embodiment the autoimmune disorder is caused by activity of the classical complement pathway. In another embodiment the autoimmune disorder is caused by a mechanism of action that is not directly related to the complement system, such as the over-proliferation of T-lymphocytes or the over-production of cytokines.

Non-limiting examples of autoimmune disorders include: lupus, allograft rejection, autoimmune thyroid diseases (such as Graves' disease and Hashimoto's thyroiditis), autoimmune uveoretinitis, giant cell arteritis, inflammatory bowel diseases (including Crohn's disease, ulcerative colitis, regional enteritis, granulomatous enteritis, distal ileitis, regional ileitis, and terminal ileitis), diabetes, multiple sclerosis, pernicious anemia, psoriasis, rheumatoid arthritis, sarcoidosis, and scleroderma.

In one embodiment, a morphic form or composition as described herein is used in the treatment of lupus. Non-limiting examples of lupus include lupus erythematosus, cutaneous lupus, discoid lupus erythematosus, chilblain lupus erythematosus, or lupus erythematosus-lichen planus overlap syndrome.

Lupus erythematosus is a general category of disease that includes both systemic and cutaneous disorders. The systemic form of the disease can have cutaneous as well as systemic manifestations. However, there are also forms of the disease that are only cutaneous without systemic involvement. For example, SLE is an inflammatory disorder of unknown etiology that occurs predominantly in women, and is characterized by articular symptoms, butterfly erythema, recurrent pleurisy, pericarditis, generalized adenopathy, splenomegaly, as well as CNS involvement and progressive renal failure. The sera of most patients (over 98%) contain antinuclear antibodies, including anti-DNA antibodies. High titers of anti-DNA antibodies are essentially specific for SLE. Conventional treatment for this disease has been the administration of corticosteroids or immunosuppressants.

There are three forms of cutaneous lupus: chronic cutaneous lupus (also known as discoid lupus erythematosus or DLE), subacute cutaneous lupus, and acute cutaneous lupus. DLE is a disfiguring chronic disorder primarily affecting the skin with sharply circumscribed macules and plaques that display erythema, follicular plugging, scales, telangiectasia and atrophy. The condition is often precipitated by sun exposure, and the early lesions are erythematous, round scaling papules that are 5 to 10 mm in diameter and display follicular plugging. DLE lesions appear most commonly on the cheeks, nose, scalp, and ears, but they may also be generalized over the upper portion of the trunk, extensor surfaces of the extremities, and on the mucous membranes of the mouth. If left untreated, the central lesion atrophies and leaves a scar. Unlike SLE, antibodies against double-stranded DNA (e.g., DNA-binding test) are almost invariably absent in DLE.

Multiple Sclerosis is an autoimmune demyelinating disorder that is believed to be T lymphocyte dependent. MS generally exhibits a relapsing-remitting course or a chronic progressive course. The etiology of MS is unknown, however, viral infections, genetic predisposition, environment, and autoimmunity all appear to contribute to the disorder. Lesions in MS patients contain infiltrates of predominantly T lymphocyte mediated microglial cells and infiltrating macrophages. CD4+ T lymphocytes are the predominant cell type present at these lesions. The hallmark of the MS lesion is plaque, an area of demyelination sharply demarcated from the usual white matter seen in Mill scans. Histological appearance of MS plaques varies with different stages of the disease. In active lesions, the blood-brain barrier is damaged, thereby permitting extravasation of serum proteins into extracellular spaces. Inflammatory cells can be seen in perivascular cuffs and throughout white matter. CD4+ T-cells, especially Th1, accumulate around postcapillary venules at the edge of the plaque and are also scattered in the white matter. In active lesions, up-regulation of adhesion molecules and markers of lymphocyte and monocyte activation, such as IL2-R and CD26 have also been observed. Demyelination in active lesions is not accompanied by destruction of oligodendrocytes. In contrast, during chronic phases of the disease, lesions are characterized by a loss of oligodendrocytes and hence, the presence of myelin oligodendrocyte glycoprotein (MOG) antibodies in the blood.

Diabetes can refer to either type 1 or type 2 diabetes. In one embodiment a morphic form or composition as described herein is provided at an effective dose to treat a patient with type 1 diabetes. In one embodiment a morphic form or composition as described herein is provided at an effective dose to treat a patient with type 2 diabetes. Type 1 diabetes is an autoimmune disease. An autoimmune disease results when the body's system for fighting infection (the immune system) attacks a part of the body. In the case of diabetes type 1, the pancreas then produces little or no insulin.

In some embodiments, the present invention provides a method of treating or preventing a IC-MPGN by administering to a subject in need thereof an effective amount of a morphic form or composition as described herein.

In some embodiments, the present invention provides a method of treating or preventing a delayed graft function (DGF) by administering to a subject in need thereof an effective amount of a morphic form or composition as described herein.

In some embodiments, the present invention provides a method of treating or promoting wound healing by administering to a subject in need thereof an effective amount of a morphic form or composition as described herein.

In some embodiments, the present invention provides a method of treating or preventing a HSCT-TMA by administering to a subject in need thereof an effective amount of a morphic form or composition as described herein.

In some embodiments, the present invention provides a method of treating or preventing a paroxysmal nocturnal hemoglobinuria (PNH) by administering to a subject in need thereof an effective amount a morphic form or composition as described herein.

In some embodiments, the present invention provides a method of treating or preventing age-related macular degeneration (AMD) by administering to a subject in need thereof an effective amount of a morphic form or composition as described herein.

In some embodiments, the present invention provides a method of treating or preventing macular dystrophy by administering to a subject in need thereof an effective amount of a morphic form or composition as described herein.

In some embodiments, the present invention provides a method of treating or preventing a Crohn's disease by administering to a subject in need thereof an effective amount of a morphic form or composition as described herein.

In some embodiments, the present invention provides a method of treating or preventing Stargardt's disease (Stargardt macular dystrophy) by administering to a subject in need thereof an effective amount of a morphic form or composition as described herein.

In some embodiments, the present invention provides a method of treating or preventing acute pancreatitis by administering to a subject in need thereof an effective amount of a morphic form or composition as described herein.

In some embodiments, the present invention provides a method of treating or preventing asthma (TH2) or asthma (non-TH2) by administering to a subject in need thereof an effective amount of a morphic form or composition as described herein.

In some embodiments, the present invention provides a method of treating or preventing periodontitis by administering to a subject in need thereof an effective amount of a morphic form or composition as described herein.

In some embodiments, the present invention provides a method of treating or preventing a diabetic retinopathy by administering to a subject in need thereof an effective amount of a morphic form or composition as described herein.

In some embodiments, the present invention provides a method of treating or preventing a hidradenitis suppurativa by administering to a subject in need thereof an effective amount of a morphic form or composition as described herein.

In some embodiments, the present invention provides a method of treating or preventing acute respiratory distress syndrome (ARDS) by administering to a subject in need thereof an effective amount of a morphic form or composition as described herein.

In some embodiments, the present invention provides methods of treating or preventing a nephrology disorder selected from acute kidney injury (AKI), idiopathic membranous nephropathy, IgA nephropathy (IgAN) lupus nephritis (LN), and primary focal segmental glomerulosclerosis by administering to a subject in need thereof an effective amount of a morphic form or composition as described herein.

In some embodiments, the present invention provides methods of treating or preventing preeclampsia by administering to a subject in need thereof an effective amount of a morphic form or composition as described herein.

Combination Therapy

In one embodiment a morphic form or composition as described herein may be provided in combination or alternation with or preceded by, concomitant with or followed by, an effective amount of at least one additional therapeutic agent, for example, for treatment of a disorder listed herein. Non-limiting examples of second active agents for such combination therapy are provided below.

In one embodiment, a morphic form or composition as described herein may be provided in combination or alternation with at least one additional inhibitor of the complement system or a second active compound with a different biological mechanism of action.

In non-limiting embodiments, a morphic form or composition as described herein may be provided together with a protease inhibitor, a soluble complement regulator, a therapeutic antibody (monoclonal or polyclonal), complement component inhibitor, receptor agonist, or siRNA.

In other embodiments, a morphic form described herein is administered in combination or alternation with an antibody against tumor necrosis factor (TNF), including but not limited to infliximab (Remicade), adalimumab, certolizumab, golimumab, or a receptor fusion protein such as etanercept (Embrel).

In another embodiment, a morphic form as described herein can be administered in combination or alternation with an anti-CD20 antibody, including but not limited to rituximab (Rituxan), adalimumab (Humira), ofatumumab (Arzerra), tositumomab (Bexxar), obinutuzumab (Gazyva), or ibritumomab (Zevalin).

In an alternative embodiment, a morphic form as described herein can be administered in combination or alternation with an anti-IL6 antibody, including but not limited to tocilizumab (Actemra) and siltuximab (Sylvant).

In an alternative embodiment, a morphic form as described herein can be administered in combination or alternation with an IL17 inhibitor, including but not limited to secukinumab (Cosentyx).

In an alternative embodiment, a morphic form as described herein can be administered in combination or alternation with a p40 (IL12/IL23) inhibitor, including but not limited to ustekinumab (Stelara).

In an alternative embodiment, a morphic form as described herein can be administered in combination or alteration with an IL23 inhibitor, including but not limited to risankizumab.

In an alternative embodiment, a morphic form as described herein can be administered in combination or alteration with an anti-interferon α antibody, for example but not limited to sifalimumab.

In an alternative embodiment, a morphic form as described herein can be administered in combination or alteration with a kinase inhibitor, for example but not limited to a JAK1/JAK3 inhibitor, for example but not limited to tofacitinib (Xelianz). In an alternative embodiment, a morphic form as described herein can be administered in combination or alteration with a JAK1/JAK2 inhibitor, for example but not limited to baricitinib.

In an alternative embodiment, a morphic form or composition as described herein can be administered in combination or alteration with an anti-VEGF agent, for example but not limited to: aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib (Nexavar); ponatinib (Inclusig); regorafenib (Stivarga); cabozantinib (Abometyx; Cometriq); vandetanib (Caprelsa); ramucirumab (Cyramza); lenvatinib (Lenvima); ziv-aflibercept (Zaltrap); cediranib (Recentin); anecortane acetate, squalamine lactate, and corticosteroids.

In another embodiment, a morphic form as described herein can be administered in combination or alternation with an immune checkpoint inhibitor. Non-limiting examples of checkpoint inhibitors include anti-PD-1 or anti-PDL1 antibodies, for example, nivolumab (Opdivo), pembrolizumab (Keytruda), pidilizumab, AMP-224 (AstraZeneca and MedImmune), PF-06801591 (Pfizer), MEDI0680 (AstraZeneca), PDR001 (Novartis), REGN2810 (Regeneron), SHR-12-1 (Jiangsu Hengrui Medicine Company and Incyte Corporation), TSR-042 (Tesaro), and the PD-L1/VISTA inhibitor CA-170 (Curis Inc.), atezolizumab, durvalumab, and KN035, or anti-CTLA4 antibodies, for example Ipilimumab, Tremelimumab, AGEN1884 and AGEN2041 (Agenus).

Non-limiting examples of active agents that can be used in combination with active compounds described herein are:
- Protease inhibitors: plasma-derived C1-INH concentrates, for example Cetor® (Sanquin), Berinert-P® (CSL Behring, Lev Pharma), and Cinryze®; recombinant human C1-inhibitors, for example Rhucin®; ritonavir (Norvir®, Abbvie, Inc.);
- Soluble complement regulators: Soluble complement receptor 1 (TP10) (Avant Immunotherapeutics); sCR1-sLe$^x$/TP-20 (Avant Immunotherapeutics); MLN-2222/CAB-2 (Millenium Pharmaceuticals); Mirococept (Inflazyme Pharmaceuticals);
- Therapeutic antibodies: Eculizumab/Soliris (Alexion Pharmaceuticals); Pexelizumab (Alexion Pharmaceuticals); Ofatumumab (Genmab A/S); TNX-234 (Tanox); TNX-558 (Tanox); TA106 (Taligen Therapeutics); Neutrazumab (G2 Therapies); Anti-properdin (Novelmed Therapeutics); HuMax-CD38 (Genmab A/S);
- Complement component inhibitors: Compstatin/POT-4 (Potentia Pharmaceuticals); ARC1905 (Archemix); 4(1MEW)APL-1,APL-2 (Appelis); CP40/AMY-101, PEG-Cp40 (Amyndas);
- PDGF inhibitors: Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil;
- Anti-factor H or anti-factor B agents: Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas);
- Complement C3 or CAP C3 Convertase targeting molecules: TT30 (CR2/CFH) (Alexion); TT32 (CR2/CR1)

(Alexion Pharmaceuticals); Nafamostat (FUT-175, Futhan) (Toni Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH; Anti-CR3, anti-MASP2, anti C1s, and anti-C1n molecules: Cynryze (ViroPharma/Baxter); TNT003 (True North); OMS721 (Omeros); OMS906 (Omeros); and Imprime PGG (Biothera);

Receptor agonists: PMX-53 (Peptech Ltd.); JPE-137 (Jerini); JSM-7717 (Jerini);

Others: Recombinant human MBL (rhMBL; Enzon Pharmaceuticals); Imides and glutarimide derivatives such as thalidomide, lenalidomide, pomalidomide; Additional non-limiting examples that can be used in combination or alternation with a morphic form or composition as described herein include the following.

Non-limiting examples of potential therapeutics for combination therapy

| Name | Target | Company | Class of Molecule |
|---|---|---|---|
| LFG316 | C5 | Novartis/Morphosys | Monoclonal antibody |
| 4(1MEW)APL-1, APL-2 | C3/C3b | Apellis | Compstatin Family |
| 4(1MeW)POT-4 | C3/C3b | Potentia | Compstatin Family |
| Anti-C5 siRNA | C5 | Alnylam | Si-RNA |
| Anti-FB siRNA | CFB | Alnylam | SiRNA |
| ARC1005 | C5 | Novo Nordisk | Aptamers |
| ATA | C5 | N.A. | Chemical |
| Coversin | C5 | Volution Immuno-Pharmaceuticals | Small animal protein |
| CP40/AMY-101, PEG-Cp40 | C3/C3b | Amyndas | Compstatin Family |
| CRIg/CFH | CAP C3 convertase | NA | CFH-based protein |
| Cynryze | C1n/C1s | ViroPharma/Baxter | Human purified protein |
| FCFD4514S | CFD | Genentech/Roche | Monoclonal antibody |
| H17 | C3 (C3b/iC3b) | EluSys Therapeutics | Monoclonal antibody |
| Mini-CFH | CAP C3 convertase | Amyndas | CFH-based protein |
| Mirococept (APT070) | CAP and CCP C3 | NA | CR1-based protein |
| Mubodine | C5 | Adienne | Monoclonal antibody |
| RA101348 | C5 | Rapharma | Small molecule |
| sCR1 (CDX-1135) | CAP and CP C3 | Celldex | CR1-based protein |
| SOBI002 | C5 | Swedish Orphan Biovitrum | Affibody |
| SOMAmers | C5 | SomaLogic | Aptamers |
| SOMAmers | CFB and CFD | SomaLogic | Aptamers (SELEX) |
| TA106 | CFB | Alexion Pharmaceuticals | Monoclonal antibody |
| TNT003 | C1s | True North | Monoclonal antibody |
| TT30 (CR2/CFH) | CAP C3 convertase | Alexion | CFH-based protein |
| TT32 (CR2/CR1) | CAP and CCP C3 | Alexion Pharmaceuticals | CR1-based protein |
| Nafamostat (FUT-175, Futhan) | C1s, CFD, other proteases | Torri Pharmaceuticals | Small molecule |
| OMS721 | MASP-2 | Omeros | Monoclonal antibody |
| OMS906 | MASP-2 | Omeros | Monoclonal antibody |
| Bikaciomab, NM9308 | CFB | Novelmed | Monoclonal antibody |
| NM9401 | Properdin | Novelmed | Monoclonal antibody |
| CVF, HC-1496 | C3 | InCode | Recombinant peptide |
| ALXN1102/ALXN1103 (TT30) | C3-conv, C3b | Alexion Pharmaceuticals | Regulator |
| rFH | C3-conv, C3b | Optherion | Regulator |
| 5C6, AMY-301 | CFH | Amyndas | Regulator |
| Erdigna | C5 | Adienne Pharma | Antibody |
| ARC 1905 | C5 | Opthotech | Monoclonal Antibody |
| MEDI7814 | C5/C5a | MedImmune | Monoclonal Antibody |
| NOX-D19 | C5a | Noxxon | Aptamer (Spiegelmer) |
| IFX-1, CaCP29 | C5a | InflaRx | Monoclonal Antibody |
| PMX53, PMX205 | C5aR | Cephalon, Teva | Peptidomimetic |
| CCX168 | C5aR | ChemoCentryx | Small molecule |
| ADC-1004 | C5aR | Alligator Bioscience | Small molecule |
| Anti-C5aR-151, NN8209; Anti-C5aR-215, NN8210 | C5aR | Novo Nordisk | Monoclonal Antibody |
| Imprime PGG | CR3 | Biothera | Soluble beta-glucan |
| ANX005; ANX007 | C1q | Annexon | Monoclonal Antibody |
| Lampalizumab | fD | Roche | Monoclonal Antibody |
| avacincaptad pegol | C5 | Opthotech | Aptamer |
| regenemab | C6 | Regenesance | Monoclonal Antibody |
| BIVV020 | C1s | Bioverativ | Monoclonal Antibody |

-continued

Non-limiting examples of potential therapeutics for combination therapy

| Name | Target | Company | Class of Molecule |
|---|---|---|---|
| PRO-02 | C2 | Broteio/Argen-x | Monoclonal Antibody |
| 5C6, compsorbin | fH | Amyndas | Peptide |
| SOBI005 | C5 | Sobi | Protein |
| ISU305 | C5 | ISU ABXIS | Monoclonal Antibody |
| Mubodina | C5 | Adienne | Monoclonal Antibody |
| IFX-2, IFX-3 | C5a | InflaRx | Monoclonal Antibody |
| ALS-205 | C5aR1 | Alsonex | Peptide |
| DF2593A | C5aR1 | Dompé | Small Molecule |
| IPH5401 | C5aR1 | Innate Pharma | Monoclonal Antibody |
| C6-LNA | C6 | Regenesance | Oligonucleotide |
| SKY59 | C5 | Roche | Monoclonal Antibody |
| REGN3918 | C5 | Regeneron | Monoclonal Antibody |
| Aptamers to Factor D | fD | Vitrisa Therapeutics | Aptamer |
| CLG561 | Properdin | Novartis | Monoclonal Antibody |
| Tesidolumab; LFG316 | C5 | Novartis and MorphoSys | Monoclonal Antibody |

In one embodiment, a morphic form or composition as described herein may be provided together with a compound that inhibits an enzyme that metabolizes an administered protease inhibitor. In one embodiment, a morphic form may be provided together with ritonavir.

In one embodiment, a morphic form or composition as described herein may be provided in combination with a complement C5 inhibitor or C5 convertase inhibitor. In another embodiment, a morphic form or composition as described herein may be provided in combination with eculizumab, a monoclonal antibody directed to the complement factor C5 and manufactured and marketed by Alexion Pharmaceuticals under the tradename Soliris. Eculizumab has been approved by the U.S. FDA for the treatment of PNH and aHUS.

In one embodiment, a morphic form or composition as described herein may be provided together with a compound that inhibits Complement Factor D. In one embodiment of the invention, a morphic form or composition as described herein as described herein can be used in combination or alternation with a compound described in Biocryst Pharmaceuticals U.S. Pat. No. 6,653,340 titled "Compounds useful in the complement, coagulate and kallikrein pathways and method for their preparation" describes fused bicyclic ring compounds that are potent inhibitors of Factor D; Novartis PCT patent publication WO2012/093101 titled "Indole compounds or analogues thereof useful for the treatment of age-related macular degeneration" describes certain Factor D inhibitors; Novartis PCT patent publications WO2013/164802, WO2013/192345, WO2014/002051, WO2014/002052, WO2014/002053, WO2014/002054, WO2014/002057, WO2014/002058, WO2014/002059, WO2014/005150, WO2014/009833, WO2014/143638, WO2015/009616, WO2015/009977, WO2015/066241, Bristol-Myers Squibb PCT patent publication WO2004/045518 titled "Open chain prolyl urea-related modulators of androgen receptor function"; Japan Tobacco Inc. PCT patent publication WO1999/048492 titled "Amide derivatives and nociceptin antagonists"; Ferring B.V. and Yamanouchi Pharmaceutical Co. LTD. PCT patent publication WO1993/020099 titled "CCK and/or gastrin receptor ligands"; Alexion Pharmaceuticals PCT patent publication WO1995/029697 titled "Methods and compositions for the treatment of glomerulonephritis and other inflammatory diseases"; or Achillion Pharmaceuticals filed PCT Patent Application No. PCT/US2015/017523 and U.S. patent application Ser. No. 14/631,090 titled "Alkyne Compounds for Treatment of Complement Mediated Disorders"; PCT Patent Application No. PCT/US2015/017538 and U.S. patent application Ser. No. 14/631,233 titled "Amide Compounds for Treatment of Complement Mediated Disorders"; PCT Patent Application No. PCT/US2015/017554 and U.S. patent application Ser. No. 14/631,312 titled "Amino Compounds for Treatment of Complement Mediated Disorders"; PCT Patent Application No. PCT/US2015/017583 and U.S. patent application Ser. No. 14/631,440 titled "Carbamate, Ester, and Ketone Compounds for Treatment of Complement Mediated Disorders"; PCT Patent Application No. PCT/US2015/017593 and U.S. patent application Ser. No. 14/631,625 titled "Aryl, Heteroaryl, and Heterocyclic Compounds for Treatment of Complement Mediated Disorders"; PCT Patent Application No. PCT/US2015/017597 and U.S. patent application Ser. No. 14/631,683 titled "Ether Compounds for Treatment of Complement Mediated Disorders"; PCT Patent Application No. PCT/US2015/017600 and U.S. patent application Ser. No. 14/631,785 titled "Phosphonate Compounds for Treatment of Complement Mediated Disorders"; and PCT Patent Application No. PCT/US2015/017609 and U.S. patent application Ser. No. 14/631,828 titled "Compounds for Treatment of Complement Mediated Disorders."

In one embodiment, a morphic form or composition as described herein is administered in combination with an anti-inflammatory drug, antimicrobial agent, anti-angiogenesis agent, immunosuppressant, antibody, steroid, ocular antihypertensive drug or combinations thereof. Examples of such agents include amikacin, anecortane acetate, anthracenedione, anthracycline, an azole, amphotericin B, bevacizumab, camptothecin, cefuroxime, chloramphenicol, chlorhexidine, chlorhexidine digluconate, clortrimazole, a clotrimazole cephalosporin, corticosteroids, dexamethasone, desamethazone, econazole, eftazidime, epipodophyllotoxin, fluconazole, flucytosine, fluoropyrimidines, fluoroquinolines, gatifloxacin, glycopeptides, imidazoles, itraconazole, ivermectin, ketoconazole, levofloxacin, macrolides, miconazole, miconazole nitrate, moxifloxacin, natamycin, neomycin, nystatin, ofloxacin, polyhexamethylene biguanide, prednisolone, prednisolone acetate, pegaptanib, platinum analogues, polymicin B, propamidine isethionate, pyrimidine nucleoside, ranibizumab, squalamine lactate, sulfonamides, triamcinolone, triamcinolone acetonide, triazoles, vancomycin, anti-vascular endothelial growth factor (VEGF) agents, VEGF antibodies, VEGF antibody fragments, vinca alkaloid, timolol, betaxolol, travoprost, latanoprost, bimatoprost, brimonidine, dorzolamide, acetazolamide, pilocarpine, ciprofloxacin, azithromycin, gentamycin, tobramycin, cefazolin, voriconazole, gancyclovir, cidofovir, foscarnet, diclofenac, nepafenac, ketorolac, ibuprofen, indomethacin, fluoromethalone, rimexolone, anecortave, cyclosporine, methotrexate, tacrolimus, anti-PDGFR molecule, and combinations thereof.

In one embodiment of the present invention, a morphic form or composition as described herein can be administered in combination or alternation with at least one immunosuppressive agent. The immunosuppressive agent as non-limiting examples, may be a calcineurin inhibitor, e.g. a cyclosporin or an ascomycin, e.g. Cyclosporin A (NEORAL®), FK506 (tacrolimus), pimecrolimus, a mTOR inhibitor, e.g. rapamycin or a derivative thereof, e.g. Sirolimus (RAPAMUNE®), Everolimus (Certican®), temsirolimus, zotarolimus, biolimus-7, biolimus-9, a rapalog, e.g. ridaforolimus, azathioprine, campath 1H, a S1P receptor modulator, e.g. fingolimod or an analogue thereof, an anti IL-8 antibody, mycophenolic acid or a salt thereof, e.g. sodium salt, or a prodrug thereof, e.g. Mycophenolate Mofetil (CELLCEPT®), OKT3 (ORTHOCLONE OKT3®), Prednisone, ATGAM®, THYMOGLOBULIN®, Brequinar Sodium, OKT4, T10B9.A-3A, 33B3.1, 15-deoxyspergualin, tresperimus, Leflunomide ARAVA®, CTLAI-Ig, anti-CD25, anti-IL2R, Basiliximab (SIMULECT®), Daclizumab (ZENAPAX®), mizorbine, methotrexate, dexamethasone, ISAtx-247, SDZ ASM 981 (pimecrolimus, Elidel®), CTLA4lg (Abatacept), belatacept, LFA3lg, etanercept (sold as Enbrel® by Immunex), adalimumab (Humira®), infliximab (Remicade®), an anti-LFA-1 antibody, natalizumab (Antegren®), Enlimomab, gavilimomab, antithymocyte immunoglobulin, siplizumab, Alefacept efalizumab, pentasa, mesalazine, asacol, codeine phosphate, benorylate, fenbufen, naprosyn, diclofenac, etodolac and indomethacin, tocilizumab (Actemra), siltuximab (Sylvant), secukibumab (Cosentyx), ustekinumab (Stelara), risankizumab, sifalimumab, aspirin and ibuprofen.

Examples of anti-inflammatory agents include methotrexate, dexamethasone, dexamethasone alcohol, dexamethasone sodium phosphate, fluromet26halone acetate, fluromethalone alcohol, lotoprendol etabonate, medrysone, prednisolone acetate, prednisolone sodium phosphate, difluprednate, rimexolone, hydrocortisone, hydrocortisone acetate, lodoxamide tromethamine, aspirin, ibuprofen, suprofen, piroxicam, meloxicam, flubiprofen, naproxan, ketoprofen, tenoxicam, diclofenac sodium, ketotifen fumarate, diclofenac sodium, nepafenac, bromfenac, flurbiprofen sodium, suprofen, celecoxib, naproxen, rofecoxib, glucocorticoids, diclofenac, and any combination thereof. In one embodiment, a morphic form or composition as described herein is combined with one or more non-steroidal anti-inflammatory drugs (NSAIDs) selected from naproxen sodium (Anaprox), celecoxib (Celebrex), sulindac (Clinoril), oxaprozin (Daypro), salsalate (Disalcid), diflunisal (Dolobid), piroxicam (Feldene), indomethacin (Indocin), etodolac (Lodine), meloxicam (Mobic), naproxen (Naprosyn), nabumetone (Relafen), ketorolac tromethamine (Toradol), naproxen/esomeprazole (Vimovo), and diclofenac (Voltaren), and combinations thereof.

In one embodiment, a morphic form or composition as described herein is administered in combination or alteration with an omega-3 fatty acid or a peroxisome proliferator-activated receptor (PPARs) agonist. Omega-3 fatty acids are known to reduce serum triglycerides by inhibiting DGAT and by stimulating peroxisomal and mitochondrial beta oxidation. Two omega-3 fatty acids, eicosapentaenoic acid (EPA) and docosahexaenoic acid (DHA), have been found to have high affinity for both PPAR-alpha and PPAR-gamma. Marine oils, e.g., fish oils, are a good source of EPA and DHA, which have been found to regulate lipid metabolism. Omega-3 fatty acids have been found to have beneficial effects on the risk factors for cardiovascular diseases, especially mild hypertension, hypertriglyceridemia and on the coagulation factor VII phospholipid complex activity. Omega-3 fatty acids lower serum triglycerides, increase serum HDL-cholesterol, lower systolic and diastolic blood pressure and the pulse rate, and lower the activity of the blood coagulation factor VII-phospholipid complex. Further, omega-3 fatty acids seem to be well tolerated, without giving rise to any severe side effects. One such form of omega-3 fatty acid is a concentrate of omega-3, long chain, polyunsaturated fatty acids from fish oil containing DHA and EPA and is sold under the trademark Omacor®. Such a form of omega-3 fatty acid is described, for example, in U.S. Pat. Nos. 5,502,077, 5,656,667 and 5,698,594, the disclosures of which are incorporated herein by reference.

Peroxisome proliferator-activated receptors (PPARs) are members of the nuclear hormone receptor superfamily ligand-activated transcription factors that are related to retinoid, steroid and thyroid hormone receptors. There are three distinct PPAR subtypes that are the products of different genes and are commonly designated PPAR-alpha, PPAR-beta/delta (or merely, delta) and PPAR-gamma. General classes of pharmacological agents that stimulate peroxisomal activity are known as PPAR agonists, e.g., PPAR-alpha agonists, PPAR-gamma agonists and PPAR-delta agonists. Some pharmacological agents are combinations of PPAR agonists, such as alpha/gamma agonists, etc., and some other pharmacological agents have dual agonist/antagonist activity. Fibrates such as fenofibrate, bezafibrate, clofibrate and gemfibrozil, are PPAR-alpha agonists and are used in patients to decrease lipoproteins rich in triglycerides, to increase HDL and to decrease atherogenic-dense LDL. Fibrates are typically orally administered to such patients. Fenofibrate or 2-[4-(4-chlorobenzoyl)phenoxy]-2-methylpropanoic acid, 1-methylethyl ester, has been known for many years as a medicinally active principle because of its efficacy in lowering blood triglyceride and cholesterol levels.

In one embodiment, the present invention provides a method of treating or preventing age-related macular degeneration (AMD) by administering to a subject in need thereof an effective amount of a morphic form or composition as described herein in combination with an anti-VEGF agent. Non-limiting examples of anti-VEGF agents include, but are not limited to, aflibercept (Eylea®; Regeneron Pharmaceuticals); ranibizumab (Lucentis®: Genentech and Novartis); pegaptanib (Macugen®; OSI Pharmaceuticals and Pfizer); bevacizumab (Avastin; Genentech/Roche); lapatinib (Tykerb); sunitinib (Sutent); axitinib (Inlyta); pazopanib; sorafenib (Nexavar); ponatinib (Inclusig); regorafenib (Stivarga); Cabozantinib (Abometyx; Cometriq); vendetanib (Caprelsa); ramucirumab (Cyramza); lenvatinib (Lenvima); ziv-aflibercept (Zaltrap); cediranib (Recentin); anecortane acetate, squalamine lactate, and corticosteroids, including, but not limited to, triamcinolone acetonide.

In one embodiment, the present invention provides a method of treating or preventing age-related macular degeneration (AMD) by administering to a subject in need thereof an effective amount of a morphic form or composition as described herein in combination with a complement C5 inhibitor, for example, a complement C5 inhibitor described herein and in the table above titled Non-limiting examples of potential therapeutics for combination therapy, including, but not limited to, eculizumab; LFG316 (Novartis/Morphosys); Anti-C5 siRNA (Alnyl am); ARC1005 (Novo Nordisk); Coversin (Volution Immuno-Pharmaceuticals); Mubodine (Adienne Pharma); RA101348 (Ra Pharma); SOBI002 (Swedish Orphan Biovitrum); SOMAmers (SomaLogic); Erdigna (Adienne Pharma); ARC1905 (Opthotech); MEDI7814 (MedImmune); NOX-D19 (Noxxon); IFX-1, CaCP29 (InflaRx); PMX53, PMX205 (Cephalon, Teva); CCX168 (ChemoCentryx); ADC-1004 (Alligator Bioscience); and Anti-C5aR-151, NN8209; Anti-C5aR-215, NN8210 (Novo Nordisk).

In one embodiment, the present invention provides a method of treating or preventing age-related macular degeneration (AMD) by administering to a subject in need thereof an effective amount of a morphic form or composition as described herein in combination with anti-properidin agent, for example, an anti-properidin agent as described above, including but not limited to NM9401 (Novelmed).

In one embodiment, the present invention provides a method of treating or preventing age-related macular degeneration (AMD) by administering to a subject in need thereof an effective amount of a morphic form or composition as described herein in combination with a complement C3 inhibitor for example, a complement C3 inhibitor described above, including, but not limited to, a compstatin or compstatin analogue, for example Compstatin/POT-4 (Potentia Pharmaceuticals); ARC1905 (Archemix); 4(1MEW)APL-1, APL-2 (Appelis); CP40/AMY-101,PEG-Cp40 (Amyndas) Complement C3 or CAP C3 Convertase targeting molecules: TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); and CRIg/CFH.

In one embodiment, the present invention provides a method of treating or preventing age-related macular degeneration (AMD) by administering to a subject in need thereof an effective amount of a morphic form or composition as described herein in combination with an anti-factor H or anti-factor B agent selected from Anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas).

In one embodiment, the present invention provides a method of treating or preventing age-related macular degeneration (AMD) by administering to a subject in need thereof an effective amount of a morphic form or composition as described herein in combination with an anti-MASP2, anti-C1s or anti-CR3 molecules, for example, but not limited to: Cynryze (ViroPharma/Baxter); TNT003 (True North); OMS721 (Omeros); OMS906 (Omeros); and Imprime PGG (Biothera).

In one embodiment, the present invention provides a method of treating or preventing age-related macular degeneration (AMD) by administering to a subject in need thereof an effective amount of a morphic form or composition as described herein in combination with an PDGF inhibitor, for example as described herein including but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil.

In one embodiment, the present invention provides a method of treating or preventing paroxysmal nocturnal hemoglobinuria (PNH) by administering to a subject in need thereof an effective amount of a morphic form or composition as described herein with an additional inhibitor of the complement system or another active compound with a different biological mechanism of action. In another embodiment, the present invention provides a method of treating or preventing paroxysmal nocturnal hemoglobinuria (PNH) by administering to a subject in need thereof an effective amount of a morphic form or composition as described herein in combination or alternation with eculizumab. In another embodiment, the present invention provides a method of treating or preventing paroxysmal nocturnal hemoglobinuria (PNH) by administering to a subject in need thereof an effective amount of a morphic form or composition as described herein in combination or alternation with CP40. In one embodiment, the additional agent is PEGylated-CP40. CP40 is a peptide inhibitor that shows a strong binding affinity for C3b and inhibits hemolysis of paroxysmal nocturnal hemoglobinuria (PNH) erythrocytes. In one embodiment, the additional agent is a complement component inhibitor, for example but not limited to Compstatin/POT-4 (Potentia Pharmaceuticals); ARC1905 (Archemix); 4(1MEW)APL-1,APL-2 (Appelis); CP40/AMY-101, PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera)

In one embodiment, the present invention provides a method of treating or preventing rheumatoid arthritis by administering to a subject in need thereof an effective amount of a composition comprising a morphic form or composition as described herein in combination or alternation with an additional inhibitor of the complement system, or an active agent that functions through a different mechanism of action. In another embodiment, the present invention provides a method of treating or preventing rheumatoid arthritis by administering to a subject in need thereof an effective amount of a morphic form or composition as described herein in combination or alternation with methotrexate. In certain embodiments, a morphic form or composition as described herein is administered in combination or alternation with at least one additional therapeutic agent selected from: salicylates including aspirin (Anacin, Ascriptin, Bayer Aspirin, Ecotrin) and salsalate (Mono-Gesic, Salgesic); nonsteroidal anti-inflammatory drugs (NSAIDs); nonselective inhibitors of the cyclo-oxygenase (COX-1 and COX-2) enzymes, including diclofenac (Cataflam, Voltaren), ibuprofen (Advil, Motrin), ketoprofen (Orudis), naproxen (Aleve, Naprosyn), piroxicam (Feldene), etodolac (Lodine), indomethacin, oxaprozin (Daypro), nabumetone (Relafen), and meloxicam (Mobic); selective cyclo-oxygenase-2 (COX-2) inhibitors including Celecoxib (Celebrex); disease-modifying antirheumatic drugs (DMARDs), including azathioprine (Imuran), cyclosporine (Sandimmune, Neoral), gold salts (Ridaura, Solganal, Aurolate, Myochrysine), hydroxychloroquine (Plaquenil), leflunomide (Arava), methotrexate (Rheumatrex), penicillamine (Cuprimine), and sulfasalazine (Azulfidine); biologic drugs including abatacept (Orencia), etanercept (Enbrel), infliximab (Remicade), adalimumab (Humira), and anakinra (Kineret); corticosteroids including betamethasone (Celestone Soluspan), cortisone (Cortone), dexamethasone (Decadron), methylprednisolone (SoluMedrol, DepoMedrol), prednisolone (Delta-Cortef), prednisone (Deltasone, Orasone), and triamcinolone (Aristocort); gold salts, including Auranofin (Ridaura); Aurothioglucose (Solganal); Aurolate; Myochrysine; or any combination thereof.

In one embodiment, the present invention provides a method of treating or preventing multiple sclerosis by administering to a subject in need thereof an effective amount of a morphic form or composition as described herein in combination or alternation with an additional inhibitor of the complement system, or an active agent that functions through a different mechanism of action. In another embodiment, the present invention provides a method of treating or preventing multiple sclerosis by administering to a subject in need thereof an effective amount of a morphic form or composition as described herein in combination or alternation with a corticosteroid. Examples of corticosteroids include, but are not limited to, prednisone, dexamethasone, solumedrol, and methylprednisolone. In one embodiment, a morphic form or composition as described herein is combined with at least one anti-multiple sclerosis drug, for example, selected from: Aubagio (teriflunomide), Avonex (interferon beta-1a), Betaseron (interferon beta-1b), Copaxone (glatiramer acetate), Extavia (interferon beta-1b), Gilenya (fingolimod), Lemtrada (alemtuzumab), Novantrone (mitoxantrone), Plegridy (peginterferon beta-1a), Rebif (interferon beta-1a), Tecfidera (dimethyl fumarate), Tysabri (natalizumab), Solu-Medrol (methylprednisolone), High-dose oral Deltasone (prednisone), H.P. Acthar Gel (ACTH), or a combination thereof.

In an additional alternative embodiment, a morphic form or composition as described herein may be provided in combination with eculizumab for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, a morphic form or composition as described herein may be provided in combination with compstatin or a compstatin derivative for the treatment of PNH, aHUSs, STEC-HUS, ANCA-vasculitis, AMD, CAD, C3 glomerulopathy, for example DDD or C3GN, chronic hemolysis, neuromyelitis optica, or transplantation rejection. In one embodiment, the additional agent is a complement component inhibitor, for example but not limited to Compstatin/POT-4 (Potentia Pharmaceuticals); ARC1905 (Archemix); 4(1MEW)APL-1,APL-2 (Appelis); CP40/AMY-101,PEG-Cp40 (Amyndas); a PDGF inhibitor, for example, but not limited to Sorafenib Tosylate; Imatinib Mesylate (STI571); Sunitinib Malate; Ponatinib (AP24534); Axitinib; Imatinib (STI571); Nintedanib (BIBF 1120); Pazopanib HCl (GW786034 HCl); Dovitinib (TKI-258, CHIR-258); Linifanib (ABT-869); Crenolanib (CP-868596); Masitinib (AB1010); Tivozanib (AV-951); Motesanib Diphosphate (AMG-706); Amuvatinib (MP-470); TSU-68 (SU6668, Orantinib); CP-673451; Ki8751; Telatinib; PP121; Pazopanib; KRN 633; Dovitinib (TKI-258) Dilactic Acid; MK-2461; Tyrphostin (AG 1296); Dovitinib (TKI258) Lactate; Sennoside B; Sunitinib; AZD2932; and Trapidil; an anti-factor H or anti-factor B agent, for example anti-FB siRNA (Alnylam); FCFD4514S (Genentech/Roche) SOMAmers for CFB and CFD (SomaLogic); TA106 (Alexion Pharmaceuticals); 5C6, and AMY-301 (Amyndas); a complement C3 or CAP C3 convertase targeting molecule, for example but not limited to TT30 (CR2/CFH) (Alexion); TT32 (CR2/CR1) (Alexion Pharmaceuticals); Nafamostat (FUT-175, Futhan) (Torri Pharmaceuticals); Bikaciomab, NM9308 (Novelmed); CVF, HC-1496 (InCode) ALXN1102/ALXN1103 (TT30) (Alexion Pharmaceuticals); rFH (Optherion); H17 C3 (C3b/iC3b) (EluSys Therapeutics); Mini-CFH (Amyndas) Mirococept (APT070); sCR1 (CDX-1135) (Celldex); CRIg/CFH, an anti-CR3, anti-MASP2, anti C1s, or anti-C1n molecule, for example but not limited to Cynryze (ViroPharma/Baxter); TNT003 (True North); OMS721 (Omeros); OMS906 (Omeros); and Imprime PGG (Biothera).

In one embodiment, a morphic form or composition as described herein may be provided in combination with rituxan for the treatment of a complement mediated disorder. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, a morphic form or composition as described herein may be provided in combination with cyclophosphamide for the treatment of a complement mediated disorder. In one embodiment, the disorder is an autoimmune disease. In one embodiment, the complement mediated disorder is, for example, rheumatoid arthritis, Granulomatosis with Polyangiitis (GPA) (Wegener's Granulomatosis), and Microscopic Polyangiitis (MPA). In one embodiment, the disorder is Lupus.

In one embodiment, a morphic form or composition as described herein is dosed in combination with a conventional DLE treatment for the treatment of lupus to a subject in need thereof.

Examples of conventional DLE treatments include topical corticosteroid ointments or creams, such as triamcinolone acetonide, fluocinolone, flurandrenolide, betamethasone valerate, or betamethasone dipropionate. Resistant plaques can be injected with an intradermal corticosteroid. Other potential DLE treatments include calcineurin inhibitors such as pimecrolimus cream or tacrolimus ointment. Particularly resistant cases can be treated with systemic antimalarial drugs, such as hydroxychloroquine (PLAQUENIL).

In one embodiment, a morphic form or composition as described herein may be provided in combination with methotrexate for the treatment of Lupus.

In one embodiment, a morphic form or composition as described herein may be provided in combination with azathioprine for the treatment of Lupus.

In one embodiment, a morphic form or composition as described herein may be provided in combination with a non-steroidal anti-inflammatory drug for the treatment of Lupus.

In one embodiment, a morphic form or composition as described herein may be provided in combination with a corticosteroid for the treatment of Lupus.

In one embodiment, a morphic form or composition as described herein may be provided in combination with a belimumab (Benlysta) for the treatment of Lupus.

In one embodiment, a morphic form or composition as described herein may be provided in combination with hydroxychloroquine (Plaquenil) for the treatment of Lupus.

In one embodiment, a morphic form or composition as described herein may be provided in combination with sifalimumab for the treatment of Lupus.

In one embodiment, a morphic form or composition as described herein may be provided in combination with OMS721 (Omeros) for the treatment of a complement mediated disorder. In one embodiment, a morphic form or composition as described herein may be provided in combination with OMS906 (Omeros) for the treatment of a complement mediated disorder. In one embodiment, the complement mediated disorder is, for example, thrombotic thrombocytopenic purpura (TTP) or aHUS.

In one embodiment, a morphic form or composition as described herein may be provided in combination with an anti-inflammatory agent, immunosuppressive agent, or anti-cytokine agent for the treatment or prevention of cytokine or inflammatory reactions in response to the administration of pharmaceuticals or biotherapeutics (e.g. adoptive T-cell therapy (ACT) such as CAR T-cell therapy, or monoclonal antibody therapy). In one embodiment, a morphic form or composition as described herein may be provided in combination with a corticosteroid, for example prednisone, dexamethasone, solumedrol, and methylprednisolone, and/or anti-cytokine compounds targeting, e.g., IL-4, IL-10, IL-11, IL-13 and TGFβ. In one embodiment, a morphic form or composition as described herein may be provided in combination with an anti-cytokine inhibitor including, but are not limited to, adalimumab, infliximab, etanercept, protopic, efalizumab, alefacept, anakinra, siltuximab, secukibumab, ustekinumab, golimumab, and tocilizumab, or a combination thereof. Additional anti-inflammatory agents that can be used in combination with a morphic form or composition as described herein include, but are not limited to, non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex); 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline); DAB 486-IL-2 and/or DAB 389-IL-2 (IL-2 fusion proteins; Seragen); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein); R973401 (phosphodiesterase Type IV inhibitor); MK-966 (COX-2 Inhibitor); Iloprost, leflunomide (anti-inflammatory and cytokine inhibition); tranexamic acid (inhibitor of plasminogen activation); T-614 (cytokine inhibitor); prostaglandin E1; Tenidap (non-steroidal anti-inflammatory drug); Naproxen (non-steroidal anti-inflammatory drug); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine; Azathioprine; ICE inhibitor (inhibitor of the enzyme interleukin-1β converting enzyme); zap-70 and/or lck inhibitor (inhibitor of the tyrosine kinase zap-70 or lck); TNF-convertase inhibitors; anti-IL-12 antibodies; anti-IL-18 antibodies; interleukin-11; interleukin-13; interleukin-17 inhibitors; gold; penicillamine; chloroquine; chlorambucil; hydroxychloroquine; cyclosporine; cyclophosphamide; anti-thymocyte globulin; anti-CD4 antibodies; CD5-toxins; orally-administered peptides and collagen; lobenzarit disodium; Cytokine Regulating Agents (CRAB) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine).

In a specific embodiment, a morphic form or composition as described herein may be provided in combination with a corticosteroid for the treatment or prevention of cytokine or inflammatory reactions in response to the administration of pharmaceuticals or biotherapeutics. In another embodiment, a morphic form or composition as described herein may be provided in combination with etanercept for the treatment or prevention of cytokine or inflammatory reactions in response to the administration of pharmaceuticals or biotherapeutics. In another embodiment, a morphic form or composition as described herein may be provided in combination with tocilizumab for the treatment or prevention of cytokine or inflammatory reactions in response to the administration of pharmaceuticals or biotherapeutics. In another embodiment, a morphic form or composition as described herein may be provided in combination with etanercept and tocilizumab for the treatment or prevention of cytokine or inflammatory reactions in response to the administration of pharmaceuticals or biotherapeutics. In another embodiment, a morphic form or composition as described herein may be provided in combination with infliximab for the treatment or prevention of cytokine or inflammatory reactions in response to the administration of pharmaceuticals or biotherapeutics. In another embodiment, a morphic form or composition as described herein may be provided in combination with golimumab for the treatment or prevention of cytokine or inflammatory reactions in response to the administration of pharmaceuticals or biotherapeutics.

C5 Inhibitors

Provided herein are methods for treating factor D mediated disorders in a subject comprising administering to the subject an effective amount of a C5 inhibitor in combination or alternation with an effective amount of a CFD inhibitor selected from Formula I or Formula II. In certain embodiments the factor D mediated disorder is PNH.

C5 inhibitors are known in the art. In one embodiment, the C5 inhibitor is a monoclonal antibody targeting C5. In one embodiment, the C5 inhibitor is eculizumab (Soliris™ Alexion Pharmaceuticals, New Haven, Conn., see, e.g., U.S. Pat. No. 9,352,035). In one embodiment, the C5 inhibitor is ravulizumab. In one embodiment the C5 inhibitor is a small molecule pharmaceutical. In another embodiment the C5 inhibitor is an antibody. In another embodiment the C5 inhibitor is a polyclonal antibody targeting C5. In yet another embodiment the C5 inhibitor is an aptamer.

In some embodiments, the C5 inhibitor may be, but is not limited to: a recombinant human minibody, for example Mubodina® (monoclonal antibody, Adienne Pharma and Biotech, Bergamo, Italy; see U.S. Pat. No. 7,999,081); coversin (small animal protein, Volution Immuno-pharmaceuticals, Geneva, Switzerland; see e.g. Penabad et al. Lupus, 2012, 23(12):1324-6); LFG316 (monoclonal antibody, Novartis, Basel, Switzerland, and Morphosys, Planegg, Germany; see U.S. Pat. Nos. 8,241,628 and 8,883,158); ARC-1905 (pegylated RNA aptamer, Ophthotech, Princeton, N.J. and New York, N.Y.; see Keefe et al., Nature Reviews Drug Discovery, 9, 537-550); RA101348 and RA101495 (macrocyclic peptides, Ra Pharmaceuticals, Cambridge, Mass.); SOBI002 (affibody, Swedish Orphan Biovitrum, Stockholm, Sweden); ALN-CC5 (Si-RNA, Alnylam Pharmaceuticals, Cambridge, Mass.); ARC1005 (aptamers, Novo Nordisk, Bagsvaerd, Denmark); SOMAmers (aptamers, SomaLogic, Boulder, Colo.); SSL7 (bacterial protein toxin, see, e.g. Laursen et al. Proc. Natl. Acad. Sci. U.S.A., 107(8):3681-6); MEDI7814 (monoclonal antibody, MedImmune, Gaithersburg, Md.); aurin tricarboxylic acid; aurin tricarboxylic acid derivatives (Aurin Biotech, Vancouver, BC, see U.S. Patent Appl. Pub. 2013/003592); RG6107 (anti-C5 recycling antibody, Roche Pharmaceuticals, Basel, Switzerland); Ravulizumab (ALXN1210) and ALXN5500 (monoclonal antibodies, Alexion Pharmaceuticals, New Haven, Conn.); TT30 (fusion protein, Alexion Pharmaceuticals, New Haven, Conn.); REGN3918 (monoclonal antibody, Regeneron, Tarrytown, N.Y.); ABP959 (eculizumab biosimilar, Amgen, Thousand Oaks, Calif.); or combinations thereof.

In one embodiment, the C5 inhibitor is a recombinant human minibody, for example Mubodina®. Mubodina® is a fully human recombinant antibody C5 developed by Adienne Pharma and Biotech. Mubodina® is described in U.S. Pat. No. 7,999,081.

In one embodiment, the C5 inhibitor is coversin. Coversin is a recombinant protein derived from a protein discovered in the saliva of the *Ornithodoros moubata* tick currently developed as a recombinant protein by Akari Therapeutics. Coversin is described in Penabad et al. Lupus 2012, 23(12): 1324-6.

In one embodiment, the C5 inhibitor is Tesidolumab/LFG316. Tesidolumab is a monoclonal antibody developed by Novartis and Morphosys. Tesidolumab is described in U.S. Pat. Nos. 8,241,628 and 8,883,158.

In one embodiment, the C5 inhibitor is ARC-1905. ARC-1905 is a pegylated RNA aptamer developed by Ophthotech. ARC-1905 is described in Keefe et al. Nature Reviews Drug Discovery, 9:537-550.

In one embodiment, the C5 inhibitor is RA101348. RA101348 is a macrocyclic peptide developed by Ra Pharmaceuticals.

In one embodiment, the C5 inhibitor is RA101495. RA101495 is a macrocyclic peptide developed by Ra Pharmaceuticals.

In one embodiment, the C5 inhibitor is SOBI002. SOBI002 is an affibody developed by the Swedish Orphan Biovitrum.

In one embodiment, the C5 inhibitor is ARC1005. ARC1005 is an aptamer developed by Novo Nordisk.

In one embodiment, the C5 inhibitor is SOMAmers for C5. SOMAmers are aptamers developed by SomaLogic.

In one embodiment, the C5 inhibitor is SSL7. SSL7 is a bacterial protein toxin described in Laursen et al. Proc. Natl. Acad. Sci. U.S.A., 107(8):3681-6.

In one embodiment, the C5 inhibitor is MEDI7814. MEDI7814 is a monoclonal antibody developed by MedImmune.

In one embodiment, the C5 inhibitor is aurin tricarboxylic acid. In another embodiment, the C5 inhibitor is an aurin tricarboxylic acid derivative. These aurin derivatives were developed by Aurin Biotech and are further described in U.S. Patent Appl. Pub. No. 2013/003592).

In one embodiment, the C5 inhibitor is RG6107/SKY59. RG6107/SKY59 is an anti-C5 recycling antibody developed by Roche Pharmaceuticals.

In one embodiment, the C5 inhibitor is Ravulizumab (ALXN1210). In another embodiment, the C5 inhibitor is ALXN5500. ALXN1210 and ALXN5500 are monoclonal antibodies developed by Alexion Pharmaceuticals.

In one embodiment, the C5 inhibitor is TT30. TT30 is a fusion protein developed by Alexion Pharmaceuticals.

In one embodiment, the C5 inhibitor is ABP959. ABP959 is an eculizumab biosimilar monoclonal antibody developed by Amgen.

In one embodiment, the C5 inhibitor is Anti-C5 siRNA. Anti-C5 siRNA was developed by Alnylam Pharmaceuticals.

In one embodiment, the C5 inhibitor is Erdigna®. Erdigna® is an antibody developed by Adienne Pharma.

In one embodiment, the C5 inhibitor is avacincaptad pegol/Zimura®. Avacincaptad pegol is in aptamer developed by Opthotech.

In one embodiment, the C5 inhibitor is SOBI005. SOBI005 is a protein in developed by the Swedish Orphan Biovitrum.

In one embodiment, the C5 inhibitor is ISU305. ISU305 is a monoclonal antibody developed by ISU ABXIS.

In one embodiment, the C5 inhibitor is REGN3918. REGN3918 is a monoclonal antibody developed by Regeneron.

In another embodiment, a morphic form or composition as described herein may be provided in combination with ABP959, a monoclonal antibody directed to the complement factor C5 and manufactured and marketed by Amgen. In another embodiment, a morphic form or composition or composition as described herein may be provided in combination with BOWo8o, a monoclonal antibody directed to the complement factor C5 and manufactured and marketed by Epirus Biopharmaceuticals. In another embodiment, a morphic form or composition or composition as described herein may be provided in combination with SB12, a monoclonal antibody directed to the complement factor C5 and manufactured and marketed by Samsung Bioepis.

C3 Inhibitors

Provided herein are methods for treating complement factor D mediated disorders in a subject comprising administering to the subject an effective amount of a C3 inhibitor in combination or alternation with an effective amount of a CFD inhibitor selected from Formula I or Formula II. In certain embodiments the factor D mediated disorder is PNH.

In one embodiment the C3 inhibitor is a small molecule. In another embodiment the C3 inhibitor is a polyclonal antibody targeting C3. In another embodiment the C3 inhibitor is a monoclonal antibody targeting C3. In yet another embodiment the C3 inhibitor is an aptamer.

C3 inhibitors are known in the art. In one embodiment, a morphic form or composition of the present invention is administered in combination or alternation with compstatin and/or a compstatin analog. Compstatin and compastin analogs are known and are found to be useful inhibitors of C3, see U.S. Pat. Nos. 9,056,076; 8,168,584; 9,421,240; 9,291,622; 8,580,735; 9,371,365; 9,169,307; 8,946,145; 7,989,589; 7,888,323; 6,319,897; and US Patent Appl. Pub. Nos. 2016/0060297; 2016/0015810; 2016/0215022; 2016/0215020; 2016/0194359; 2014/0371133; 2014/0323407; 2014/0050739; 2013/0324482; and 2015/0158915. In one embodiment, the compstatin analog having the amino acid sequence ICVVQDWGHHCRT (SEQ. ID. NO. 1). In another embodiment, the C3 inhibitor is a compstatin analog. In one embodiment, the compstatin analog is 4(1MeW)/APL-1 of the sequence Ac-ICV(1-mW)QDWGAHRCT (SEQ. ID. NO. 2), wherein Ac is acetyl and 1-mW is 1-methyltryptophan. In another embodiment, the compstatin analog is Cp40/AMY-101, which has an amino acid sequence yICV(1mW)QDW-Sar-AHRC-mI (SEQ. ID. NO. 3), wherein y is D-tyrosine, 1mW is 1-methyltryptophan, Sar is sarcosine, and mI is N-methylisoleucine. In yet another embodiment, the compstatin analog is PEG-Cp40, having the amino acid sequence PEG-yICV(1mW)QDW-Sar-AHRC-mI (SEQ. ID. NO. 4), wherein PEG is polyethyleneglycol (40 kDa), y is D-tyrosine, 1mW is 1-methyltryptophan, Sar is sarcosine, and mI is N-methylisoleucine. In yet another embodiment, the compstatin analog is 4(1MeW) POT-4. 4(1MeW)POT-4 was developed by Potentia. In yet another embodiment, the compstatin analog is AMY-201. AMY-201 was developed by Amyndas Pharmaceuticals.

In some embodiments, a morphic form or composition of the present invention can be combined with C3 inhibitors that include, but are not limited to: H17 (monoclonal antibody, EluSys Therapeutics, Pine Brook, N.J.); mirococept (CR1-based protein); sCR1 (CR1-based protein, Celldex, Hampton, N.J.); TT32 (CR-1 based protein, Alexion Pharmaceuticals, New Haven, Conn.); HC-1496 (recombinant peptide); CB 2782 (enzyme, Catalyst Biosciences, South San Francisco, Calif.); APL-2 (pegylated synthetic cyclic peptide, Apellis Pharmaceuticals, Crestwood, Ky.); or combinations thereof.

In one embodiment, the C3 inhibitor is H17. H17 is a humanized monoclonal antibody in development by EluSys Therapeutics. H17 is described in Paixao-Cavalcante et al. J. Immunol. 2014, 192(10):4844-4851.

In one embodiment, the C3 inhibitor is mirococept. Mirococept is a CR1-based protein developed by Inflazyme Pharmaceuticals.

In one embodiment, the C3 inhibitor is sCR1. sCR1 is a soluble form of the CR1 protein developed by Celldex.

In one embodiment, the C3 inhibitor is TT32. TT32 is a CR-1 based protein developed by Alexion Pharmaceuticals.

In one embodiment, the C3 inhibitor is HC-1496. HC-1496 is a recombinant peptide developed by InCode.

In one embodiment, the C3 inhibitor is CB 2782. CB 2782 is novel protease derived from human membrane type serine protease 1 (MTSP-1) that was developed by Catalyst Biosciences.

In one embodiment, the C3 inhibitor is APL-2. APL-2 is a pegylated version of APL-1 developed by Apellis Pharmaceuticals.

Complement Factor B (CFB) Inhibitors

Provided herein are methods for treating complement factor D mediated disorders comprising administering a CFB inhibitor in combination or alternation with a morphic form or composition of the present invention. In certain embodiments the factor D mediated disorder is PNH. CFB inhibitors are known in the art. In some embodiments, a morphic form or composition of the present invention can be combined with CFB inhibitors that include, but are not limited to: anti-FB SiRNA (Alnylam Pharmaceuticals, Cambridge, Mass.); TA106 (monoclonal antibody, Alexion Pharmaceuticals, New Haven, Conn.); LNP023 (small molecule, Novartis, Basel, Switzerland); SOMAmers (aptamers, SomaLogic, Boulder, Colo.); bikaciomab (Novelmed Therapeutics, Cleveland, Ohio); complin (see, Kadam et al., J. Immunol. 2010, DOI:10.409/jimmunol.10000200); Ionis-FB-$L_{Rx}$ (ligand conjugated antisense drug, Ionis Pharmaceuticals, Carlsbad, Calif.); or a combination thereof. In another embodiment, CFB inhibitors that can be combined with a compound of the present invention include those disclosed in PCT/US17/39587. In another embodiment, CFB inhibitors that can be combined with a compound of the present invention as described herein include those disclosed in PCT/US17/014458. In another embodiment, CFB inhibitors that can be combined with a compound of the present invention as described herein include those disclosed in U.S. Patent Appl. Pub. No. 2016/0024079; PCT Int. Appl. WO 2013/192345; PCT Int. Appl. WO 2013/164802; PCT Int. Appl. WO 2015/066241; PCT Int. Appl. WO 2015/009616 (assigned to Novartis AG).

In one embodiment the CFB inhibitor is a small molecule. In another embodiment the CFB inhibitor is a polyclonal antibody targeting CFB. In another embodiment the CFB inhibitor is a monoclonal antibody targeting CFB. In yet another embodiment the CFB inhibitor is an aptamer.

In one embodiment, the CFB inhibitor is

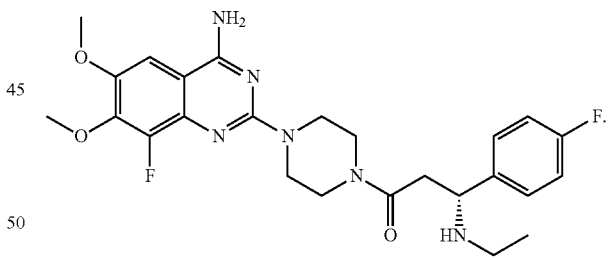

In another embodiment, the CFB inhibitor is

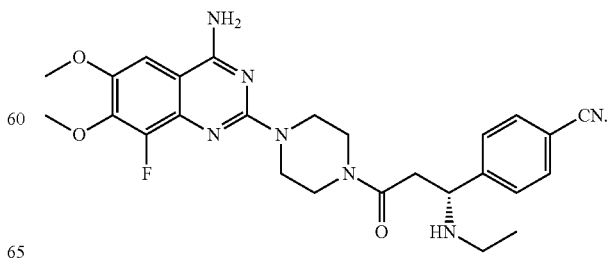

In another embodiment, the CFB inhibitor is

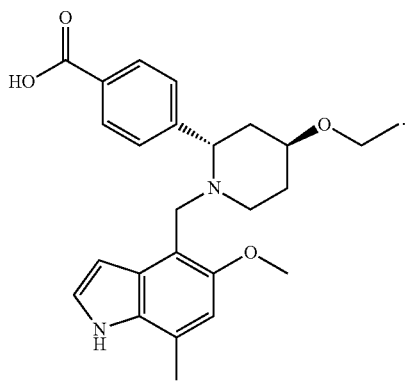 [SMILES: CCO[C@H]1CCN(Cc2c(OC)cc(C)c3[nH]ccc23)[C@H](c2ccc(C(=O)O)cc2)C1]

In one embodiment, the CFB inhibitor is anti-FB siRNA. Anti-FB siRNA was developed by Alnylam Pharmaceuticals.

In one embodiment, the CFB inhibitor is TA106. TA106 is a monoclonal antibody developed by Alexion Pharmaceuticals.

In one embodiment, the CFB inhibitor is LNP023. LNP023 is a small molecule inhibitor of CFB developed by Novartis.

In one embodiment, the CFB inhibitor is complin. Complin is a peptide inhibitor that is described in Kadam et al. J. Immunol. 2010 184(12):7116-24.

In one embodiment, the CFB inhibitor is Ionis-FB-$L_{Rx}$. Ionis-FB-$L_{Rx}$ is a ligand conjugated antisense drug developed by Ionis Pharmaceuticals.

Pan-Inhibitors of Complement Components

Provided herein are methods for treating PNH comprising administering a pan-inhibitor of complement components in combination or alternation with a compound of the present invention. Pan-inhibitors of complement components are known in the art. In one embodiment, the inhibitor is FUT-175.

Combinations for Prophylactic or Concomitant Anti-Bacterial Therapy

In one aspect of the present invention, a method is provided for treating a host in need thereof that comprises administering an effective amount of a prophylactic anti-bacterial vaccine prior to administration of a morphic form or composition for any of the disorders described herein. In another aspect of the present invention, a method is provided for treating a host in need thereof that comprises administering an effective amount of a prophylactic anti-bacterial drug, such as a pharmaceutical drug, prior to administration of a morphic form or composition for any of the disorders described herein. In one aspect of the present invention, a method is provided for treating a host in need thereof that comprises administering an effective amount of an anti-bacterial vaccine after administration of a morphic form or composition for any of the disorders described herein. In another aspect of the present invention, a method is provided for treating a host in need thereof that comprises administering an effective amount of an anti-bacterial drug, such as a pharmaceutical drug, after administration of a morphic form or composition for any of the disorders described herein. In one embodiment, the disorder is PNH, C3G, or aHUS. In one embodiment, the host has received an organ or other tissue or biological fluid transplant. In one embodiment, the host is also administered eculizumab.

In one aspect of the present invention, a morphic form or composition as described herein is administered to a host concomitantly to a subject following the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, a morphic form or composition as described herein is administered to a subject concomitantly with the prophylactic administration of a vaccine against a bacterial infection. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, a morphic form or composition as described herein is administered to a subject and, during the administration period of the morphic form, a vaccine against a bacterial infection is administered to the subject. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, the subject is administered a morphic form or composition as described herein in combination with an antibiotic compound for the duration of Factor D inhibitor administration. In one embodiment, the complement mediated disorder is PNH, C3G, or aHUS. In one embodiment, the subject has received an organ or other tissue or biological fluid transplant. In one embodiment, the subject is also administered eculizumab.

In one aspect of the present invention, a morphic form or composition as described herein is administered to a subject following the prophylactic administration of a vaccine against a bacterial infection, and in combination with an antibiotic compound for the duration of Factor D inhibitor administration. In one embodiment, the complement mediated disorder is PNH or aHUS. In one embodiment, the subject has received an organ or other tissue or biological fluid transplant. In one embodiment, the subject is also administered eculizumab. In one embodiment, the subject, prior to receiving a morphic form or composition as described herein, is vaccinated against a bacterial infection caused by the bacterium *Neisseria meningitidis*. In one embodiment, the subject is vaccinated against a bacterial infection caused by the bacterium *Haemophilus influenzae*. In one embodiment, the *Haemophilus influenzae* is *Haemophilus influenzae* serotype B (Hib). In one embodiment, the subject is vaccinated against a bacterial infection caused by *Streptococcus pneumoniae*. In one embodiment, the subject is vaccinated against a bacterial infection caused by the bacterium *Nisseria meningitidis, Haemophilus influenzae*, or *Streptococcus pneumoniae*, or a combination of one or more of *Nisseria meningitidis, Haemophilus influenzae*, or *Streptococcus pneumoniae*. In one embodiment, the subject is vaccinated against a bacterial infection caused by the bacterium *Nisseria meningitidis, Haemophilus influenzae*, and *Streptococcus pneumoniae*.

In other embodiments, the subject is vaccinated against a bacterial infection caused by a bacterium selected from a Gram-negative bacterium. In one embodiment, the subject is vaccinated against a bacterial infection caused by a bacterium selected from a Gram-positive bacterium. In one embodiment, the subject is vaccinated against a bacterial infection caused by the bacterium *Nisseria meningitidis, Haemophilus influenzae,* or *Streptococcus pneunemoniae,* or a combination of one or more of *Nisseria meningitidis, Haemophilus influenzae,* or *Streptococcus pneumoniae,* and one or more of, but not limited to, *Bacillus anthracis, Bordetella pertussis, Clostridium tetani, Corynebacterium diphtheria, Coxiella burnetii, Mycobacterium tuberculosis, Salmonella typhi, Vibrio cholerae, Anaplasma phagocytophilum, Ehrlichia ewingii, Ehrlichia chaffeensis, Ehrlichia canis, Neorickettsia sennetsu, Mycobacterium leprae, Borrelia burgdorferi, Borrelia mayonii, Borrelia afzelii, Borrelia garinii, Mycobacterium bovis, Staphylococcus aureus, Streptococcus pyogenes, Treponema pallidum, Francisella tularensis, Yersinia pestis.*

In one embodiment, the subject is vaccinated with one or more vaccines selected from, but not limited to, typhoid vaccine, live (Vivotif Berna Vaccine, PaxVax), typhoid Vi polysaccharide vaccine (Typhim Vi, Sanofi), pneumococcal 23-polyvalent vaccine, PCV13 (Pneumovax 23, Merck), pneumococcal 7-valent vaccine, PCV7 (Prevnar, Pfizer), pneumococcal 13-valent vaccine, PCV13 (Prevnar 13, Pfizer), *Haemophilus* b conjugate (prp-t) vaccine (ActHIB, Sanofi; Hibrix, GSK), *Haemophilus* b conjugate (hboc) vaccine (HibTITER, Neuron Biotech), *Haemophilus* b conjugate (prp-omp) vaccine (PedvaxHIB, Merck), *Haemophilus* b conjugate (prp-t) vaccine/meningococcal conjugate vaccine (MenHibrix, GSK), *Haemophilus* b conjugate (prp-t) vaccine/meningococcal conjugate vaccine/Hepatitis B vaccine (Comvax, Merck), meningococcal polysaccharide vaccine (Menomune A/C/Y/W-135, Sanofi), meningococcal conjugate vaccine/diphtheria CRM197 conjugate (Menveo, GSK; Menactra, Sanofi), meningococcal group B vaccine (Bexsero, GSK; Trumenba, Pfizer), anthrax vaccine adsorbed (Biothrax, Emergent Biosolutions), tetanus toxoid (Te Anatoxal Berna, Hendricks Regional Health), *Bacillus* Calmette and Guérin, live, intravesical (TheraCys, Sanofi; Tice BCG, Organon), cholera vaccine, live, oral (Vachora, Sanofi; Dukoral, SBL Vaccines; ShanChol, Shantha Biotec; Micromedex, Truven Health), tetanus toxoids and diphtheria absorbed (Tdap; Decavac, Sanofi; Tenivac, Sanofi; td, Massachusetts Biological Labs), diphtheria and tetanus toxois and pertussis (DTap; Daptacel, Sanofi; Infanrix, GSK; Tripedia, Sanofi), diphtheria and tetanus toxois and pertussis/polio (Kinrix, GSK; Quadracel, Sanofi), diphtheria and tetanus toxois and pertussis tetanus/hepatitis B/polio (Pediarix, GSK), diphtheria and tetanus toxois and pertussis/polio, *Haemophilus* influenza tybe b (Pentacel, Sanofi), and/or diphtheria, and pertussis (Tdap; Boostrix, GSK; Adacel, Sanofi), or a combination thereof.

As described above, a subject receiving a compound of the present invention to treat a disorder is prophylactically administered an antibiotic compound in addition to a Factor D inhibitor described herein. In one embodiment, the subject is administered an antibiotic compound for the duration of administration of the active compound to reduce the development of a bacterial infection. Antibiotic compounds for concomitant administration with a Factor D inhibitor described herein can be any antibiotic useful in preventing or reducing the effect of a bacterial infection. Antibiotics are well known in the art and include, but are not limited to, amikacin (Amikin), gentamicin (Garamycin), kanamycin (Kantrex), neomycin (Neo-Fradin), netilmicin (Netromycin), tobramycin (Nebcin), paromomycin (Humatin), streptomycin, spectinomycin (Trobicin), geldanamycin, herbimycin, rifaximin (Xifaxan), loracarbef (Lorabid), ertapenem (Invanz), doripenem (Doribax), imipenem/cilastatin (Primaxin), meropenem (Merrem), cefadroxil (Duricef), cefazolin (Ancef), cefalotin/cefalothin (Keflin), cephalexin (Keflex), cefaclor (Distaclor), cefamandole (Mandol), cefoxitin (Mefoxin), cefprozil (Cefzil), cefuroxime (Ceftin, Zinnat), cefixime (Cefspan), cefdinir (Omnicef, Cefdiel), cefditoren (Spectracef, Meiact), cefoperazone (Cefobid), cefotaxime (Claforan), cefpodoxime (Vantin) ceftazidime (Fortaz), ceftibuten (Cedax), ceftizoxime (Cefizox), ceftriaxone (Rocephin), cefepime (Maxipime), ceftaroline fosamil (Teflaro), ceftobiprole (Zeftera), teicoplanin (Targocid), vancomycin (Vancocin), telavancin (Vibativ), dalbavancin (Dalvance), oritavancin (Orbactiv), clindamycin (Cleocin), lincomycin (Lincocin), daptomycin (Cubicin), azithromycin (Zithromax, Surnamed, Xithrone), clarithromycin (Biaxin), dirithromycin (Dynabac), erythromycin (Erythocin, Erythroped), roxithromycin, troleandomycin (Tao), telithromycin (Ketek), spiramycin (Rovamycine), aztreonam (Azactam), furazolidone (Furoxone), nitrofurantoin (Macrodantin, Macrobid), linezolid (Zyvox), posizolid, radezolid, torezolid, amoxicillin (Novamox, Amoxil), ampicillin (Principen),azlocillin, carbenicillin (Geocillin), cloxacillin (Tegopen), dicloxacillin (Dynapen), flucloxacillin (Floxapen), mezlocillin (Mezlin), methicillin (Staphcillin), nafcillin (Unipen),oxacillin (Prostaphlin), penicillin G (Pentids),penicillin V (Veetids (Pen-Vee-K), piperacillin (Pipracil), penicillin G (Pfizerpen), temocillin (Negaban), ticarcillin (Ticar), amoxicillin/clavulanate (Augmentin), ampicillin/sulbactam (Unasyn), piperacillin/tazobactam (Zosyn), ticarcillin/clavulanate (Timentin),bacitracin, colistin (Coly-Mycin-S), polymyxin B, ciprofloxacin (Cipro, Ciproxin, Ciprobay), enoxacin (Penetrex), gatifloxacin (Tequin), gemifloxacin (Factive), levofloxacin (Levaquin), lomefloxacin (Maxaquin), moxifloxacin (Avelox), nalidixic acid (Neg-Gram), norfloxacin (Noroxin), ofloxacin (Floxin, Ocuflox), trovafloxacin (Trovan), grepafloxacin (Raxar), sparfloxacin (Zagam), temafloxacin (Omniflox), mafenide (Sulfamylon), sulfacetamide (Sulamyd, Bleph-10), sulfadiazine (Micro-Sulfon), silver sulfadiazine (Silvadene), sulfadimethoxine (Di-Methox, Albon), sulfamethizole (Thiosulfil Forte), sulfamethoxazole (Gantanol), sulfanilamide, sulfasalazine (Azulfidine), sulfisoxazole (Gantrisin), trimethoprim-sulfamethoxazole (Co-trimoxazole) (TMP-SMX) (Bactrim, Septra), sulfonamidochrysoidine (Prontosil), demeclocycline (Declomycin), doxycycline (Vibramycin), minocycline (Minocin), oxytetracycline (Terramycin), tetracycline (Sumycin, Achromycin V, Steclin), clofazimine (Lamprene), dapsone (Avlosulfon), capreomycin (Capastat), cycloserine (Seromycin), ethambutol (Myambutol), ethionamide (Trecator), isoniazid (I.N.H.), pyrazinamide (Aldinamide), rifampicin (Rifadin, Rimactane), rifabutin (Mycobutin), rifapentine (Priftin), streptomycin, arsphenamine (Salvarsan), chloramphenicol (Chloromycetin), fosfomycin (Monurol, Monuril), fusidic acid (Fucidin), metronidazole (Flagyl), mupirocin (Bactroban), platensimycin, quinupristin/dalfopristin (Synercid), thiamphenicol, tigecycline (Tigacyl), tinidazole (Tindamax Fasigyn), trimethoprim (Proloprim, Trimpex), and/or teixobactin, or a combination thereof.

In one embodiment, the subject is administered a prophylactic antibiotic selected from cephalosporin, for example, ceftriaxone or cefotaxime, ampicillin-sulbactam, Penicillin G, ampicillin, chloramphenicol, fluoroquinolone, aztreonam, levofloxacin, moxifloxacin, gemifloxacin, vancomycin, clindamycin, cefazolin, azithromycin, meropenem, ceftaroline, tigecycline, clarithromycin, moxifloxacin, trimethoprim/sulfamethoxazole, cefuroxime, axetil, ciprofloxacin, rifampin, minocycline, spiramycin, and cefixime, or a combination of two or more thereof.

Synthesis of Compound 1 and Compound 2

Compound 1, for example, can be synthesized by the procedure disclosed in PCT Application WO2015130795 and Compound 2, for example, can be synthesized by the procedure disclosed in PCT Application WO2017035353. An alternative synthesis of Compound 1 is shown below in Scheme 1 and an alternative synthesis of Compound 2 is shown below in Schemes 2-7.

In the synthesis of Compound 1, intermediate 9 was synthesized from intermediate 6 via a one-pot palladium-catalyzed Miyaura borylation/Suzuki cross-coupling reaction. 4-Bromo-2-methylpyrimidine (7) was reacted with bis(pinacolato)diboron to afford boronate ester 8. In the presence of catalyst Pd(ddpf)Cl$_2$, intermediate 6 underwent a Suzuki reaction with boronate ester 8 to generate the coupled product, intermediate 9. Similarly, in the synthesis of Compound 2, intermediate 12 was synthesized from intermediate 11 using a one-pot Miyaura borylation/Suzuki coupling.

This one-pot Miyaura borylation/Suzuki coupling can be conducted between bromine-containing reagents, chloride-containing reagents, iodide-containing reagents, organotriflate-containing reagents, or any combination thereof. As described in Molander et al. (*Journal of Organic Chemistry*, 2012, 72, 8678-8688), the reaction can also be conducted with alternative Suzuki catalysts including, but not limited to, XPhos-Pd-G1, XPhos-Pd-G2, XPhos, or CataCXium A as defined in Molander et al. In one embodiment, the reaction is conducted with Suzuki catalysts XPhos-Pd-G1 and XPhos or XPhos-Pd-G2 and XPhos. In addition to bis(pinacolato)diboron, the borylation reagent can also be selected from, but not limited to, pinacolborane or bisboronic acid.

EXAMPLES

Scheme 1. Synthesis of Compound 1 ((2S,4R)-1-(2-(3-Acetyl-5-(2-methylpyrimidin-5-yl)-1H-indazol-1-yl)acetyl)-N-(6-bromopyridin-2-yl)-4-fluoropyrrolidine-2-carboxamide) Form II

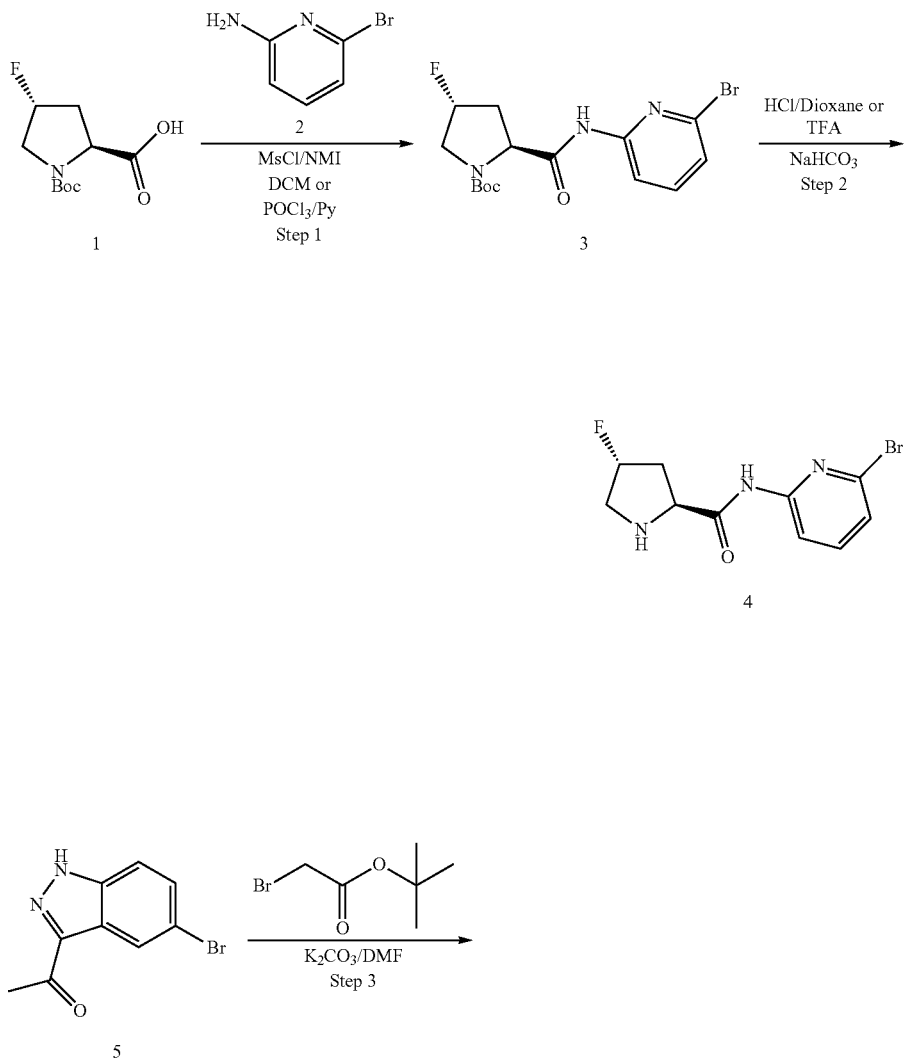

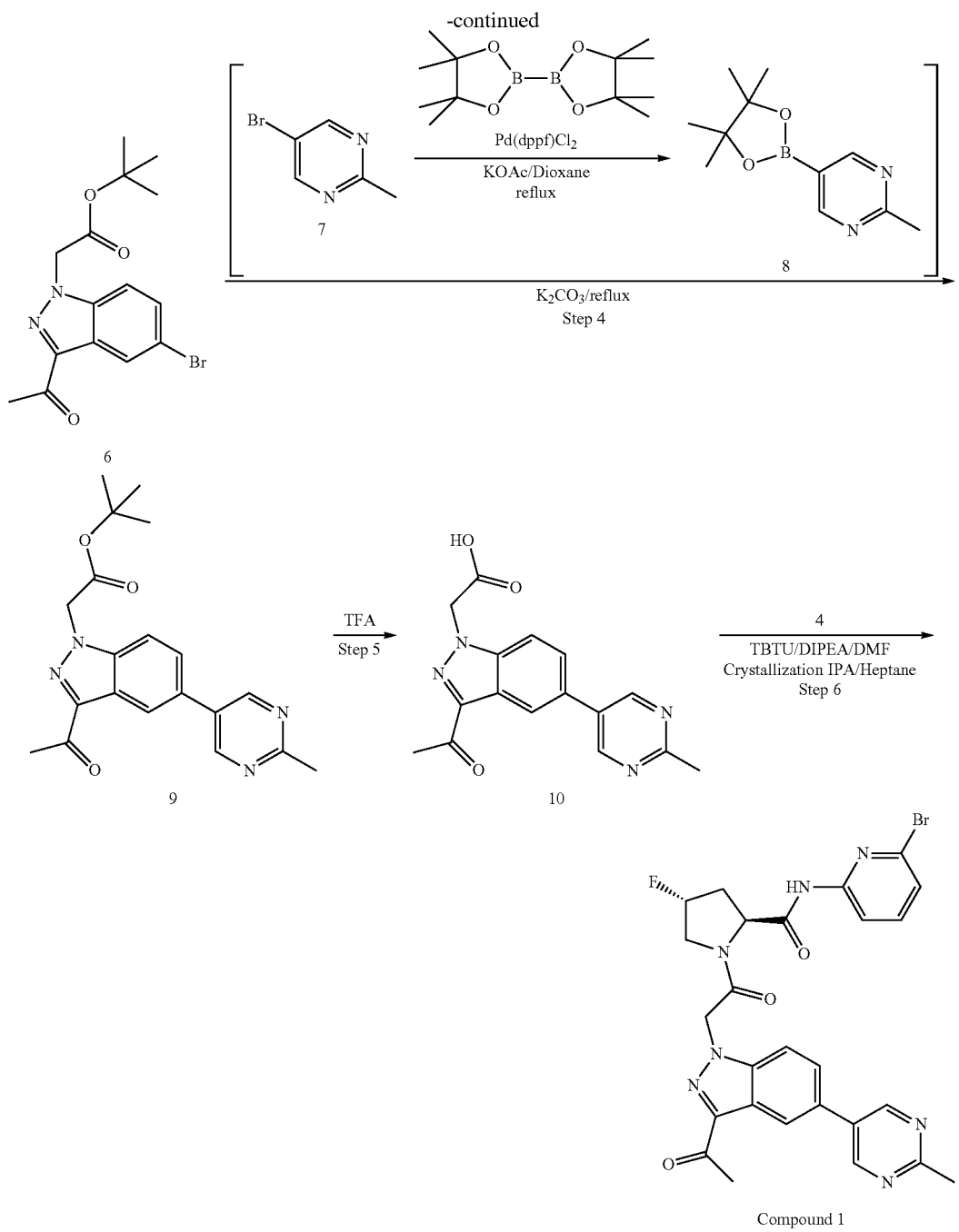

Step 1: Synthesis of tert-Butyl (2S,4R)-2-((6-bromopyridin-2-yl)carbamoyl) fluoropyrrolidine-1-carboxylate (3): N-Boc-trans-4-Fluoro-L-proline (50.8 kg) was added to DCM (1000 L) in a glass-lined reactor under an atmosphere of nitrogen. The reaction mixture was cooled to 0±5° C. and N-methylimidazole (44.7 kg) was added while maintaining the temperature at 0±5° C. Methanesulfonyl chloride (29.97 kg) was slowly added to the reaction mixture followed by the addition of 2-amino-6-bromopyridine (2). The reaction temperature was warmed to room temperature and stirred for 12 h. The reaction was monitored by HPLC. After completion of the reaction water (2,000 kg) was added, the reaction was stirred and the DCM layer separated. The aqueous layer was once more extracted with DCM (1000 L). The combined DCM layer was washed in succession with dilute HCl, aqueous NaHCO₃ and brine. The DCM extract was evaporated to dryness and tert-butyl (2S,4R)-2-((6-bromopyridin-2-yl)carbamoyl)-4-fluoropyrrolidine-1-carboxylate (3) was isolated using DCM heptane mixture and dried. Yield, 71.76 Kg (84.86%))

Step 2: Synthesis of (2S,4R)—N-(6-Bromopyridin-2-yl)-4-fluoropyrrolidine-2-carboxamide (4): To a solution 4M HCl/Dioxane (168 kg) was added intermediate 3 (40 kg) at 25±5° C. under an atmosphere of nitrogen and the reaction was stirred for 1 h. The reaction was monitored by HPLC and after completion, the reaction was diluted with DCM (800 L) and washed with aqueous NaHCO₃. The DCM layer was separated and concentrated. The product, 2S,4R)—N-

(6-bromopyridin-2-yl)-4-fluoropyrrolidine-2-carboxamide, (4), was isolated using DCM/heptane and dried. Yield, 25.81 kg, 87%.

Step 3: Synthesis of tert-Butyl 2-(3-acetyl-5-bromo-1H-indazol-1-yl)acetate (6): 1-(5-Bromo-1H-indazol-yl)ethan-1-one (5, 30 kg) was added to a reactor containing DMF (210 L) under an atmosphere of nitrogen followed by potassium carbonate (4.05 kg). Tert-butyl bromoacetate (3.42 kg) was added to the reaction mixture with stirring and maintaining the temperature at 30±10° C. After addition was complete, the reaction mixture was heated at 50±5° C. for 1 h. After the reaction was complete the reaction mixture was cooled to 25±5° C. and diluted with water (630 L). The precipitated solid was filtered, washed with water (90 L) and dried. Yield, 43.13 kg, 97.13%.

Step 4: Synthesis of tert-Butyl 2-(3-acetyl-5-(2-methylpyrimidin-5-yl)-1H-indazol-1-yl)acetate (9): Bispinnacolato diboron (14.67 kg) was added to a solution of 4-bromo methylpyrimidine (7, 10 kg) in dioxane (206 kg) under an atmosphere of nitrogen followed by the addition of potassium acetate (17 kg). The reaction mixture was degassed using nitrogen. Pd(dppf)Cl$_2$ (0.94 kg) was added and the reaction mixture heated to 90±5° C. until the pyrimidine was consumed. The reaction mixture was cooled to 25±5° C. and intermediate 6 (16.33 kg) was added followed by potassium carbonate (20.7 kg) and water (16.33 kg) and the reaction was degassed using nitrogen. The reaction was again heated to 90±5° C. until completion. The reaction mixture was cooled to 25±5° C. and diluted with ethyl acetate (269 kg) and water (150 kg) maintaining the temp at 10±5° C. Activated charcoal (1 kg) was added to the mixture with stirring and then filtered through a bed of celite. The ethyl acetate layer was separated, washed with 5% aqueous sodium chloride followed by 5% L-Cysteine solution to remove palladium related impurities. The ethyl acetate layer was evaporated to dryness. The product (9) was isolated from MTBE/heptane. Yield, 11.8 kg, 56%.

Step 5: Synthesis of 2-(3-Acetyl-5-(2-methylpyrimidin-5-yl)-1H-indazol-1-yl)acetic acid (10): To a stirred solution of intermediate 9 (50 kg) in DCM (465 kg) at 15±5° C. was added TFA (374.5 kg) while maintaining the said temperature. The reaction was warmed to 35±5° C. and stirring continued until completion of the reaction. DCM and TFA were distilled off under reduced pressure. The residue was dissolved in DCM (kg) and stirred with aqueous sodium bicarbonate. The biphasic mixture was acidified with concentrated HCl and the pH was adjusted to 2-3. The precipitated solid was filtered, washed with water and dried. Yield, 42.4 kg, quantitative.

Step 6: Synthesis of Compound 1: To a solution of intermediate 9 (42 kg) in DMF (277 kg) was added intermediate 4 (38.7 kg) and the reaction was cooled to 10±5° C. Coupling agent TBTU (56.7 kg) was added to the reaction mixture followed by the addition of DIPEA (86.5 kg) while maintaining the reaction temperature at 10±5° C. The reaction was warmed to 25±+5° C. and stirred until complete. The reaction mixture was diluted with ethyl acetate (1344 kg) and washed with water twice. (The reaction may be washed with aq. K$_2$CO$_3$ if fluorine related impurities are present.) Anhydrous sodium sulfate was added to silica gel and added to the ethyl acetate layer and filtered. The ethyl acetate layer was passed over a column of silica gel (40 kg) and the pure fractions were collected. The fractions were treated with activated charcoal and then filtered over celite. The palladium content was checked, and if above 10 ppm, the ethyl acetate layer was treated with palladium scavenging resin (SilabondThiol®). The ethyl acetate was evaporated to dryness under vacuum and the residue was crystallized from IPA (crystalline seed may be added) and heptane to afford Compound 1 Form II. Yield, 60 kg, 78%.

Example 2

Solubility Assessment of Amorphous Compound 1

Figure 1A:
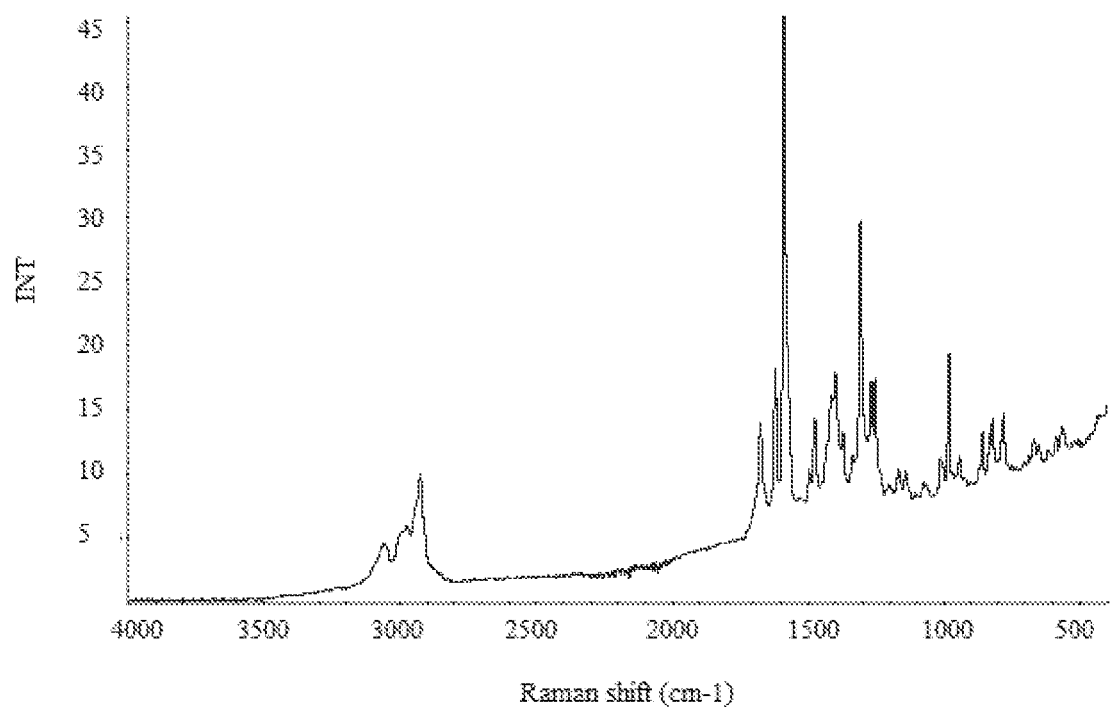
FIG. 1A is a $^1$HNMR of amorphous Compound 1, the material used in the solubility studies of Example 2 and the crystallization studies of Example 3. The x-axis is the Raman shift measured in $cm^{-1}$ and the y-axis is intensity measured in counts.
Figure 1B:
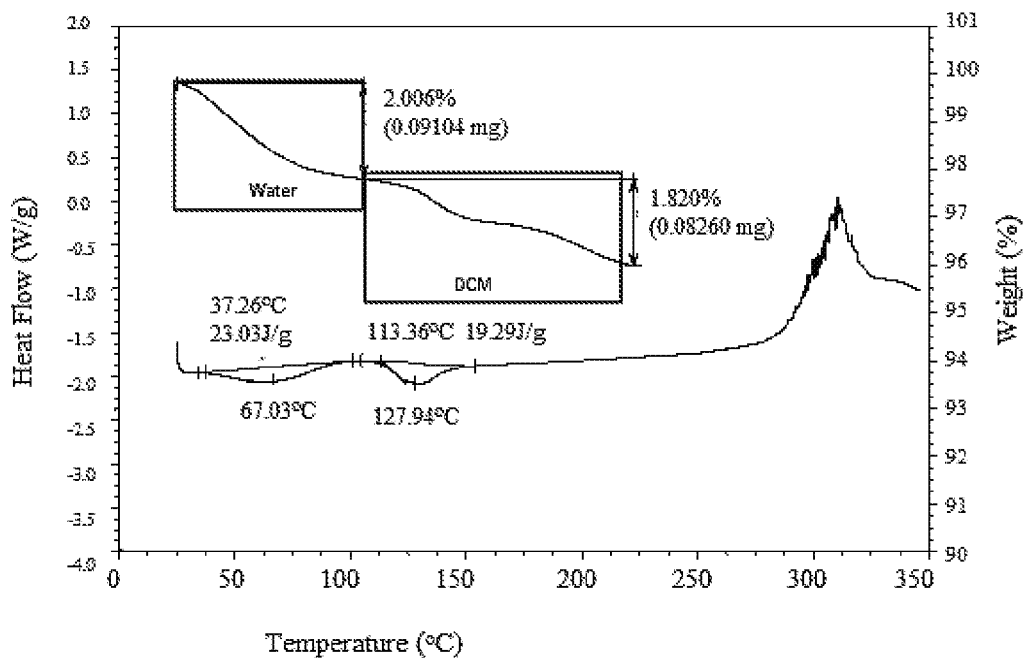
FIG. 1B is a DSC and a TGA graph of amorphous Compound 1, the material used in the solubility studies of Example 2 and the crystallization studies of Example 3. The x-axis is temperature measured in ° C., the left y-axis is heat flow measured in (W/g), and the right y-axis is weight measured in percent.
Figure 1C:
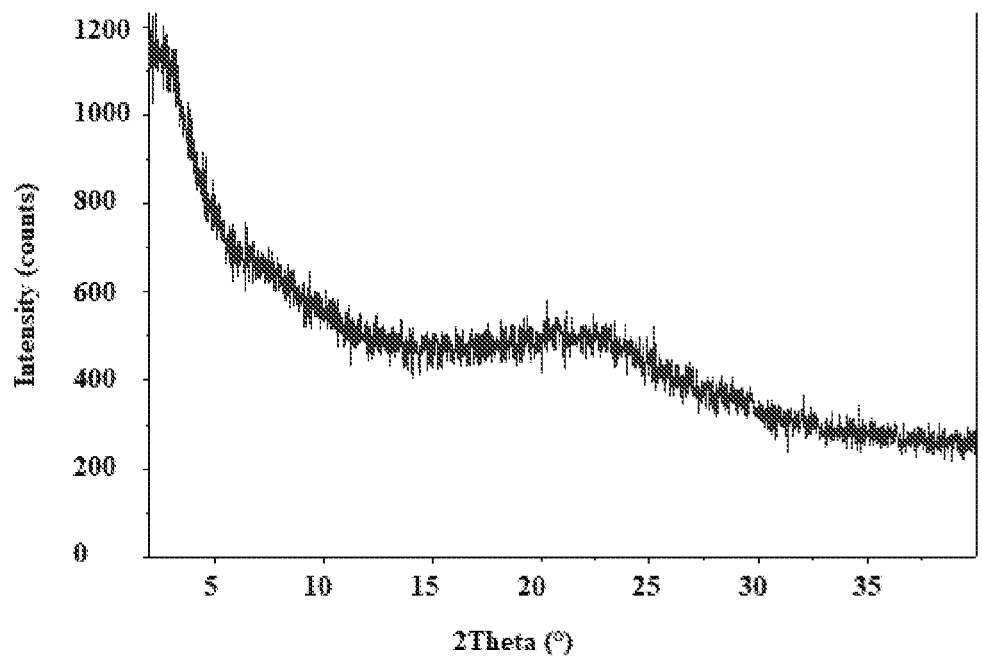
FIG. 1C is a PXRD (powder X-ray diffraction) of amorphous Compound 1, the material used in the solubility studies of Example 2 and the crystallization studies of Example 3. The x-axis is 2Theta measured in degrees and the y-axis is intensity measured in counts.
Figure 1D:
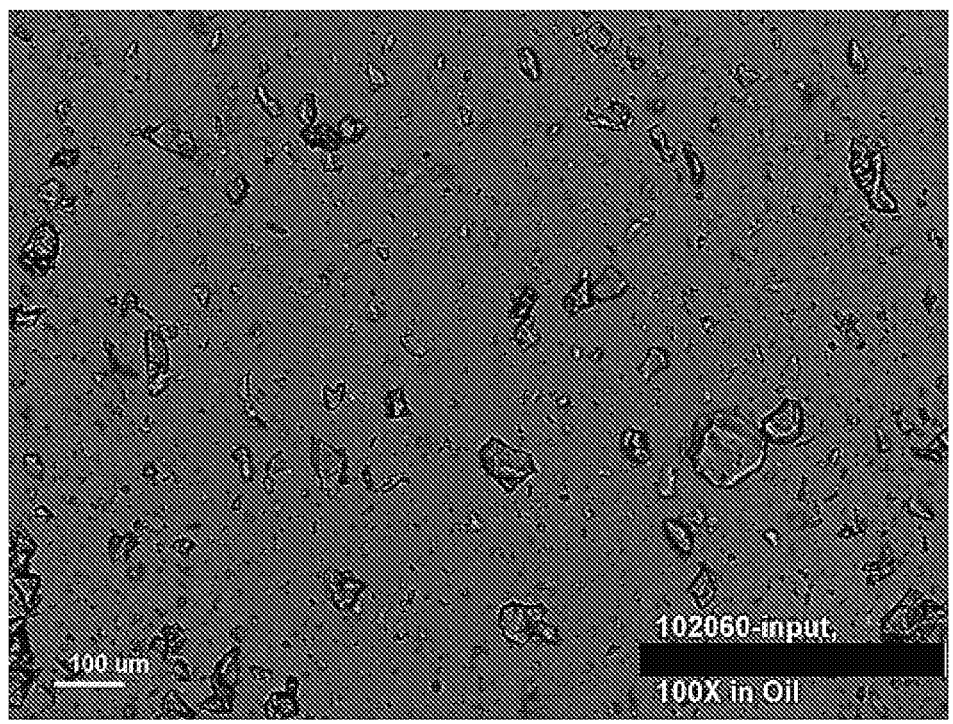
FIG. 1D is a PLM image of amorphous Compound 1, the material used in the solubility studies of Example 2 and the crystallization studies of Example 3.
Figure 1E:
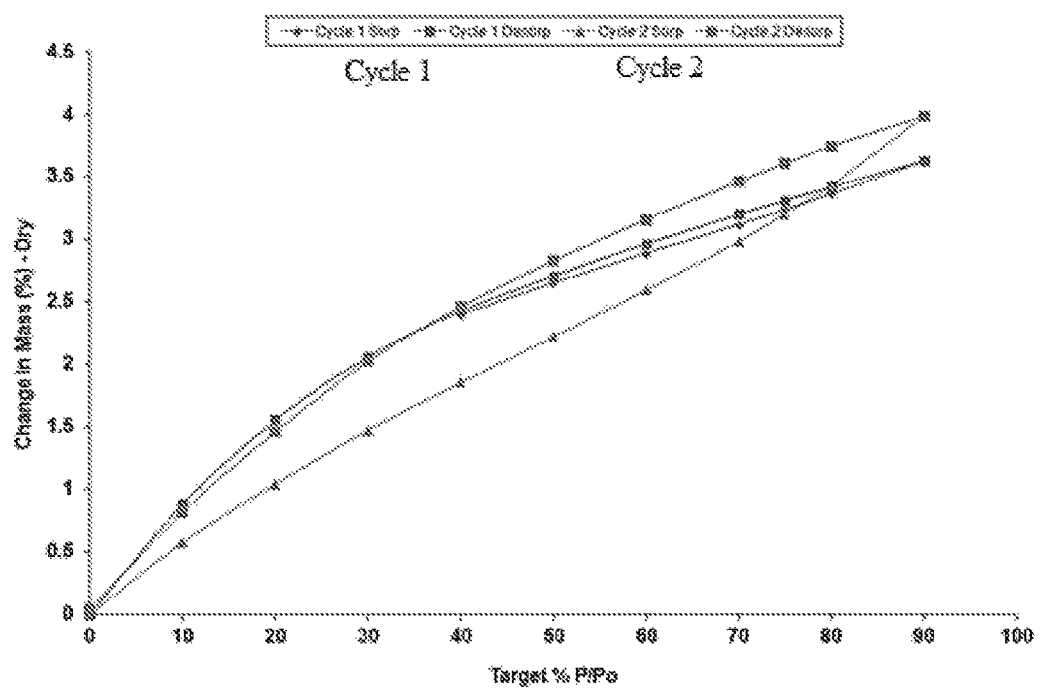
FIG. 1E is a DVS isotherm plot of amorphous Compound 1, the material used in the solubility studies of Example 2 and the crystallization studies of Example 3. The x-axis is target $P/P_o$ measured in percent and the y-axis is change in mass measured in percent.
Figure 1F:
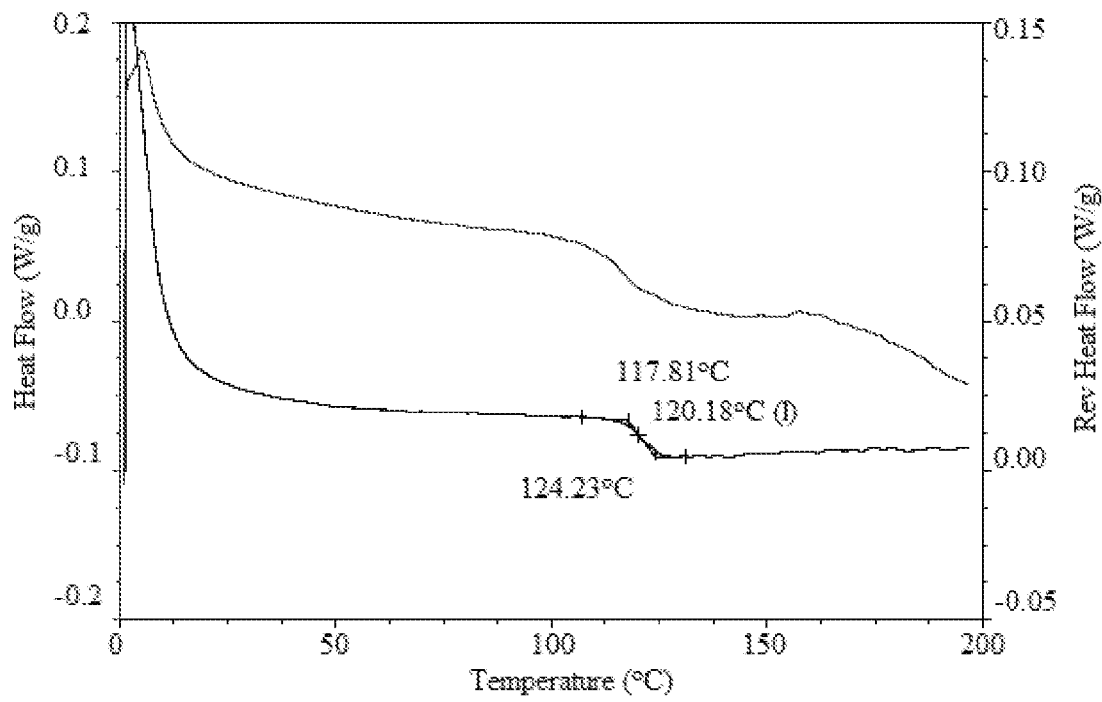
FIG. 1F is a modulated DSC graph of amorphous Compound 1, the material used in the solubility studies of Example 2 and the crystallization studies of Example 3. The x-axis is temperature measured in ° C., the left y-axis is heat flow measured in W/g and the right y-axis is rev. heat flow measured in W/g.

Amorphous Compound 1 was analyzed by FT-Raman spectroscopy, differential scanning calorimetry, (DSC), thermogravimetric analysis (TGA), TGA with IR off-gas detection (TGA-IR), polarized light microscopy (PLM), powder X-ray diffraction (PXRD), dynamic vapor sorption (DVS), and modulated DSC. The selected physicochemical data of amorphous Compound 1 is presented in FIG. 1A, FIG. 1B, FIG. 1C, FIG. 1D, FIG. 1E, and FIG. 1F. The figures indicate that the material is a light brown powder determined to be amorphous by PXRD (FIG. 1C) and PLM (FIG. 1D). The DSC data shows low energy broad endotherms at 37.3° C. and 113.4° C. (FIG. 1B). TGA-IR data (FIG. 1B) indicates that the material contains residual water (2.0%) and DCM (1.8%). DVS analysis conducted on the amorphous form indicates 4.0% water uptake from 0-90% RH (FIG. 1E). The sample remained amorphous after the DVS experiment by PXRD. In addition, no visual change to the physical appearance was observed. An estimated glass transition temperature of 117.8° C. was observed by mDSC (FIG. 1F).

The solubility of amorphous Compound 1 was estimated in 14 solvents to facilitate the solvent selection for the crystallization study. The solubility of Compound 1 was visually estimated at room temperature (RT; ~23° C.) by dosing small aliquots of solvent into a fixed amount of solid (~10 mg) until the dissolution point or a maximum volume (1.7 mL) was reached.

The solubility data are shown in Table 1 and indicate that amorphous Compound 1 is very highly soluble in DMSO (>452 mg/mL) and in most organic solvents including acetone (121-484 mg/mL). It is also highly soluble in methanol (48-96 mg/mL), but poorly soluble in heptane (<6 mg/mL), MTBE (<6 mg/mL) and water (<6 mg/mL).

TABLE 1

| | Solubility of Amorphous Compound 1 | | |
|---|---|---|---|
| # | Solvent | Solubility at RT (mg/mL) | Solubility at 40° C. (mg/mL) |
| 1 | Dimethyl Sulfoxide | >452 | N/A |
| 2 | Acetone | 121-484 | N/A |
| 3 | Dichloromethane | 99-396 | N/A |
| 4 | 1,4-Dioxane | 98-392 | N/A |
| 5 | Acetonitrile | 98-392 | N/A |
| 6 | Tetrahydrofuran | 92-368 | N/A |
| 7 | Chloroform | 92-368 | N/A |
| 8 | Ethyl Acetate | 91-364 | N/A |
| 9 | Methanol | 48-96 | N/A |
| 10 | 2-Propanol | <5.71 | >5.71 |
| 11 | t-Butyl Methyl Ether | <5.71 | <5.71 |
| 12 | Water | <5.59 | <5.59 |
| 13 | Heptane | <5.59 | <5.59 |
| 14 | Toluene | <5.35 | >5.35 |

The samples were processed by thermocycling the suspensions overnight between 40 and 5° C. Solutions were placed in a freezer overnight to induce nucleation, and subsequently evaporated to dryness at room temperature over one week. The results are shown in Table 2 and further discussed in Example 3.

TABLE 2

Products obtained from Visual Solubility

| # | Final Solvent Composition | Temperature Cycling | Cooling | Evaporation |
|---|---|---|---|---|
| CS-1 | 1-BuOH:EtOH:Water (0.4:0.4:1) | No Solid | No Solid | Amorphous |
| CS-2 | Pentane:EtOH:Water (0.4:0.2:1) | Amorphous | No Experiment | No Experiment |
| CS-3 | IPE:EtOAc:Acetone (1:0.4:0:1) | Amorphous | No Experiment | No Experiment |
| CS-4 | Water:Acetone (0.9:1) | No Solid | No Solid | Amorphous |
| CS-5 | Water:ACN:MeOH (1:0.1:0.5) | No Solid | No Solid | Amorphous |
| CS-6 | Water:MeOH (1:0.25) | No Solid | No Solid | Amorphous |
| CS-7 | Water:DMSO (1:0.37) | Amorphous | No Solid | No Solid |
| CS-8 | 2-PrOH:Water (1:0.1) | No Solid | No Solid | Amorphous |
| CS-9 | 2-PrOH:Acetone:EtOH (1:0.1:0.8) | No Solid | No Solid | Amorphous |
| CS-10 | 2-PrOH:THF:Heptane:ACN (1:0.1:08:0.25) | Nd Solid | No Solid | Amorphous |
| CS-11 | MTBE:EtOAc (1:0.1) | Amorphous | No Experiment | No Experiment |
| CS-12 | MTBE:MeOH:EtOH (1:0.1:0.1) | No Solid | Amorphous | No Experiment |
| CS-13 | MTBE:1,4-Dioxane (1:01) | No Solid | No Solid | Amorphous |
| CS-14 | Toluene:Acetone:Heptane:ACN (1:0.07:0.1:0.1) | No Solid | No Solid | Amorphous |
| CS-15 | Toluene:EtOH:Heptane (1:0.5:0.25) | No Solid | No Solid | Amorphous |
| CS-16 | Toluene:ACN (1:0.1) | No Solid | Amorphous | No Experiment |
| CS-17 | Heptane:THF (0.9:1) | Form II | No Experiment | No Experiment |
| CS-18 | Heptane:DCM (1:0.9) | Amorphous | No Experiment | No Experiment |
| CS-19 | Heptane:MeOH:EtOH (1:0.1:1) | Form II | No Experiment | No Experiment |
| CS-20 | 1-BuOH:Chloroform:Heptane (0.8:0.1:1) | Form II | No Experiment | No Experiment |
| CS-21 | 1-BuOH:1,4 Dioxane:EtOH:Heptane (1:0.1:0.75:0.5) | Form II | No Experiment | No Experiment |
| CS-22 | Cyclohexanone:1-BuOH:Heptane (0.5:0.5:1) | No Solid | No Solid | Amorphous |
| CS-23 | IPE:MTBE:Acetone (1:1:0.4) | Amorphous | No Experiment | No Experiment |
| CS-24 | Cyclohexane:Toluene:ACN (1:1:0.4) | Form II | No Experiment | No Experiment |

Example 3

Crystallization Assessment and Results

The crystallization study involved 24 unique solvent systems, three crystallization modes, and temperatures ranging between 5 and 40° C.

Solvent Selection

The crystallization study involved a total of 24 solvent systems. The solubility data from Example 2 was utilized to create a diverse set of neat and binary solvent mixtures to target a solubility of 5-100 mg/mL. Where applicable, the composition of binary mixtures was varied during the course of crystallization to achieve various levels of supersaturation to encourage crystallization. In addition, aqueous mixtures were employed to probe for the formation of hydrates.

Sample Preparation

Samples were prepared by adding ~15 mg of amorphous Compound 1 to 2 mL vials containing a tumble-stir disk. Solvents were added with volumes ranging from 250 µL to 500 µL (experiment dependent).

Crystallization Modes

The crystallization studies were comprised of the following crystallization modes:
  Slurry crystallization carried out while cycling the temperature between 40-5° C. for up to three weeks
  Cooling of clarified solutions from RT to 5° C. followed by a hold for seven days
  Evaporation of solutions at RT over 7-14 days. Solutions were slowly evaporated in a fume hood in a 2-mL vial with a loose cap Analysis of Products Polarized-Light microscopy (PLM) was chosen as the primary method for crystallinity assessment of samples produced from the crystallization study. Powder X-Ray Diffraction (PXRD) was employed to confirm the crystallinity and to obtain the solid-state fingerprint, which was subsequently used to classify the samples into groups.

For PLM, the photomicrographs were collected using Olympus BX60 polarized-light microscope equipped with Olympus DP70 camera.

PXRD diffractograms were acquired using PANalytical X'Pert Pro diffractometer on Si zero-background wafers. All diffractograms were collected using a Cu Kα (45 kV/40 mA) radiation and a step size of 0.02° 2θ and X'celerator™ RTMS (Real Time Multi-Strip) detector. Nickel filter was used to reduce unwanted radiation, unless noted otherwise. Configuration on the incidental beam side: fixed divergence slit (¼ deg), 0.04 rad soller slits, anti-scatter slit (¼ deg), and 10 mm beam mask. Configuration on the diffracted beam side: fixed divergence slit (¼ deg) and 0.04 rad soller slit.

Characterization of Forms-of-Interest

Unique crystalline products were characterized via PLM, PXRD, DSC, TGA-IR, and FT-Raman, as sample quantity permitted.

Raman spectra were collected with a Nicolet NXR9650 or NXR 960 spectrometer (Thermo Electron) equipped with 1064 nm Nd:YVO4 excitation laser, InGaAs and liquid-N2 cooled Ge detectors, and a MicroStage. All spectra were acquired at 4 cm-1 resolution, 64-128 scans, using Happ-Genzel apodization function and 2-level zero-filling.

DSC was conducted with a TA Instruments Q100 differential scanning calorimeter equipped with an autosampler and a refrigerated cooling system under 40 mL/min N2 purge. DSC thermograms were obtained at 15° C./min in crimped Al pans.

TGA thermograms were obtained with a TA Instruments Q500 thermogravimetric analyzer under 40 mL/min N2 purge at 15° C./min in Pt or Al pans.

TGA-IR was conducted with a TA Instruments Q5000 thermogravimetric analyzer interfaced to a Nicolet 6700 FT-IR spectrometer (Thermo Electron) equipped with an external TGA-IR module with a gas flow cell and DTGS detector. TGA was conducted with 60 mL/min N2 flow and heating rate of 15° C./min in Pt or Al pans. IR spectra were collected at 4 cm-1 resolution and 32 scans at each time point.

Results

As summarized in Table 2 and 3, the crystallization study and solids obtained from visual solubility experiments produced primarily amorphous products. One new crystalline hit, designated Form II, was observed in five experiments.

TABLE 3

Products obtained from Crystallization Study

| # | Solent | Temperature Cycling (TC) | Cooling | Evaporation |
|---|---|---|---|---|
| VS-1 | Water | Amorphous | No Experiment | No Experiment |
| VS-2 | DMSO | No Solid | No Solid | Amorphous |
| VS-3 | 2-Propanol | No Solid | No Solid | Amorphous |
| VS-4 | Acetone | Amorphous | No Experiment | No Experiment |
| VS-5 | Acetonitrile | No Solid | No Solid | Amorphous |
| VS-6 | 1,4-Dioxane | No Solid | No Solid | Amorphous |
| VS-7 | THF | No Solid | No Solid | Amorphous |
| VS-8 | Dichloromethane | No Solid | No Solid | Amorphous |
| VS-9 | Ethyl Acetate | No Solid | No Solid | Amorphous |
| VS-10 | t-Butyl Methyl Ether | Amorphous | No Experiment | No Experiment |
| VS-11 | Toluene | No Solid | No Solid | Amorphous |
| VS-12 | Heptane | Amorphous | No Experiment | No Experiment |
| VS-13 | MeOH | No Solid | No Solid | Amorphous |
| VS-14 | Chloroform | No Solid | No Solid | Amorphous |

Example 4

Preparation and Characterization of Crystal Forms

Figure 2:
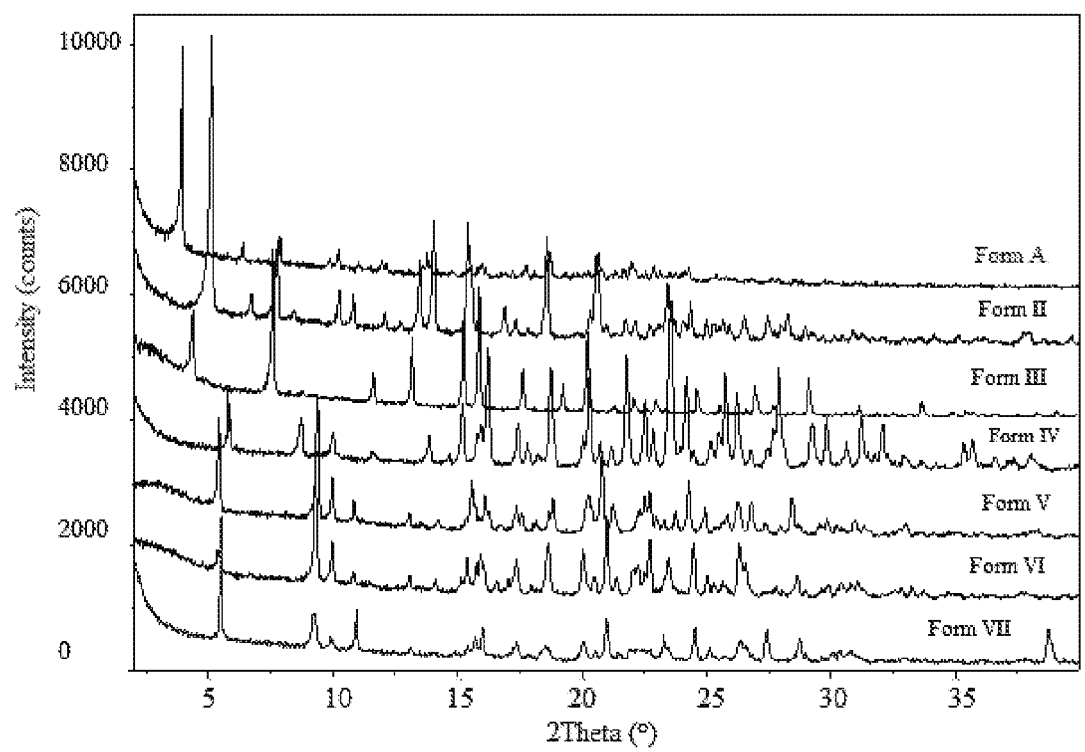
FIG. 2 is an overlay of PXRD patterns of Form A, Form II, Form III, Form IV, Form V, Form VI, and Form VII of Compound 1 as discussed in Example 4.

A summary of all identified Compound 1 Forms is shown in Table 4. Each Form is discussed in further detail. An overlay of the PXRD patterns of each form is shown in FIG. 2. A peak table containing the ten most intense peaks for each form is provided in Table 5 (all values in degrees two-theta. The ten most intense peaks (1=high intensity) for each form are provided).

TABLE 4

Summary of Amorphous Compound 1 Crystal Forms

| Designation | Form | DSC event 1 (° C.) | DSC event 2 (° C.) | Water content | Molar Eq. (~) |
|---|---|---|---|---|---|
| Form A | Hydrate | 68.6 (br.) | N/A | 2.4 | 0.8 |
| Form II | Hydrate | 40-125 (br.) | 155.3 | 2.7 | 1 |
| Form III | Hydrate | 40-100 (br.) | 139.9 | 4.1 | 1.4 |
| Form IV | Hydrate | 76.7 | N/A | 7.2 | 2.5 |
| Form V | Hydrate | 62.3 | N/A | 11.1[A] | 4 |
| Form VI[B] | Mixed Solvate | 44-100 (br.) | N/A | 13.8[D] | N/A |
| Form VII[C] | Mixed Solvate | N/A | N/A | 14.0[D] | N/A |

[A] some MeOH content
[B] water/acetone mixed solvate
[C] water/IPA mixed solvate
[D] includes solvent content
br.—broad

TABLE 5

PXRD Peak Table for all Amorphous Compound 1 Crystal Forms

| Peak # | Form A | Form II | Form III | Form IV | Form V | Form VI | Form VII |
|---|---|---|---|---|---|---|---|
| 1 | 3.9 | 5.1 | 7.6 | 23.6 | 9.4 | 9.3 | 5.5 |
| 2 | 7.9 | 14.0 | 15.9 | 21.8 | 5.4 | 21.0 | 21.0 |
| 3 | 20.6 | 15.4 | 4.4 | 16.2 | 20.8 | 22.7 | 10.9 |
| 4 | 13.8 | 18.6 | 15.3 | 27.9 | 24.3 | 26.3 | 38.7 |
| 5 | 18.7 | 20.5 | 20.2 | 18.7 | 15.6 | 24.5 | 9.2 |
| 6 | 10.2 | 7.8 | 13.2 | 25.8 | 22.7 | 18.6 | 24.5 |
| 7 | 6.4 | 13.5 | 17.7 | 20.3 | 10.0 | 20.0 | 27.4 |
| 8 | 22.0 | 15.6 | 29.1 | 24.1 | 20.3 | 10.0 | 16.0 |
| 9 | 24.3 | 20.7 | 11.6 | 26.2 | 28.4 | 15.9 | 9.3 |
| 10 | 22.9 | 23.4 | 27.0 | 5.8 | 18.8 | 23.5 | 23.3 |

Compound 1 Form A

Figure 3A:
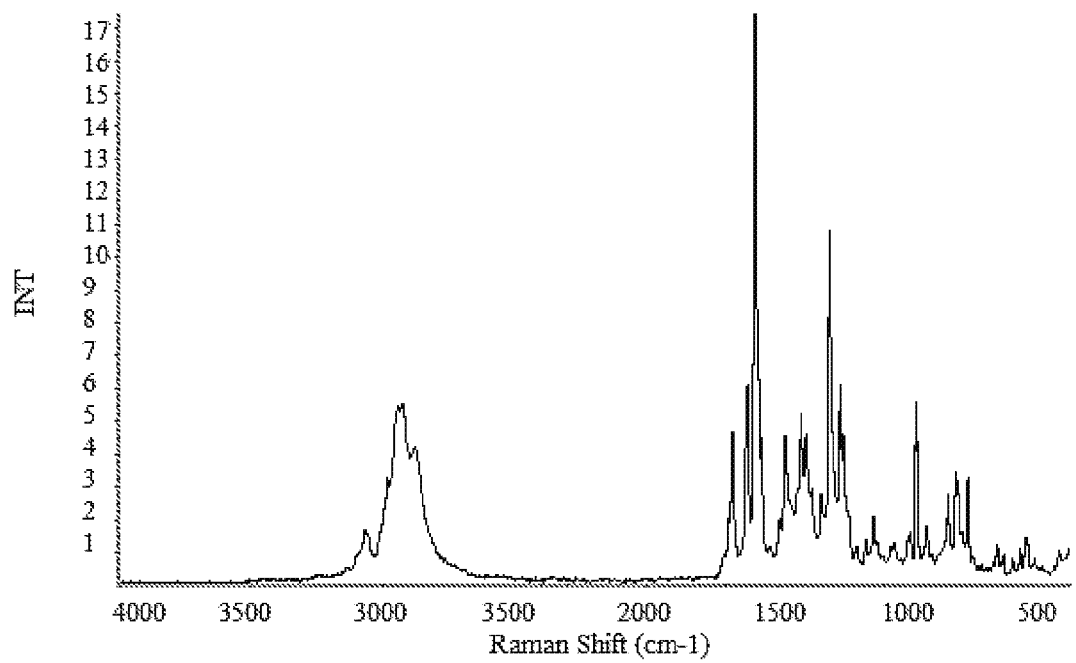
FIG. 3A is a $^1$HNMR of Compound 1 Form A as discussed in Example 4. The x-axis is the Raman shift measured in $cm^{-1}$ and the y-axis is intensity measured in counts.
Figure 3B:
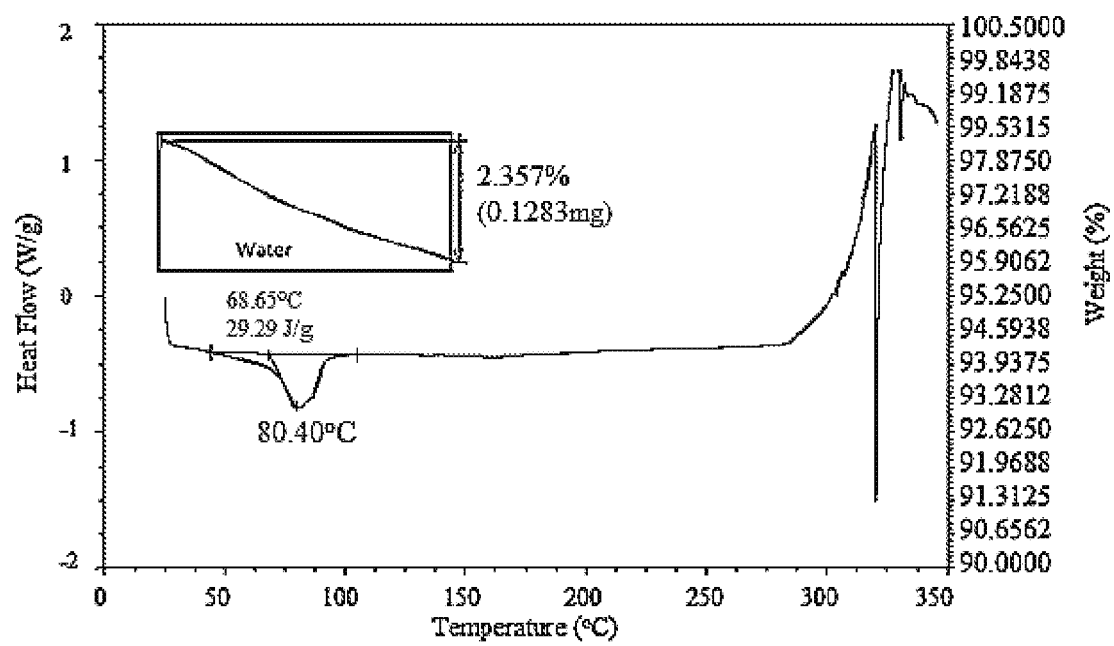
FIG. 3B is a DSC and a TGA graph of Compound 1 Form A as discussed in Example 4. The x-axis is temperature measured in ° C., the left y-axis is heat flow measured in (W/g), and the right y-axis is weight measured in percent.
Figure 3C:
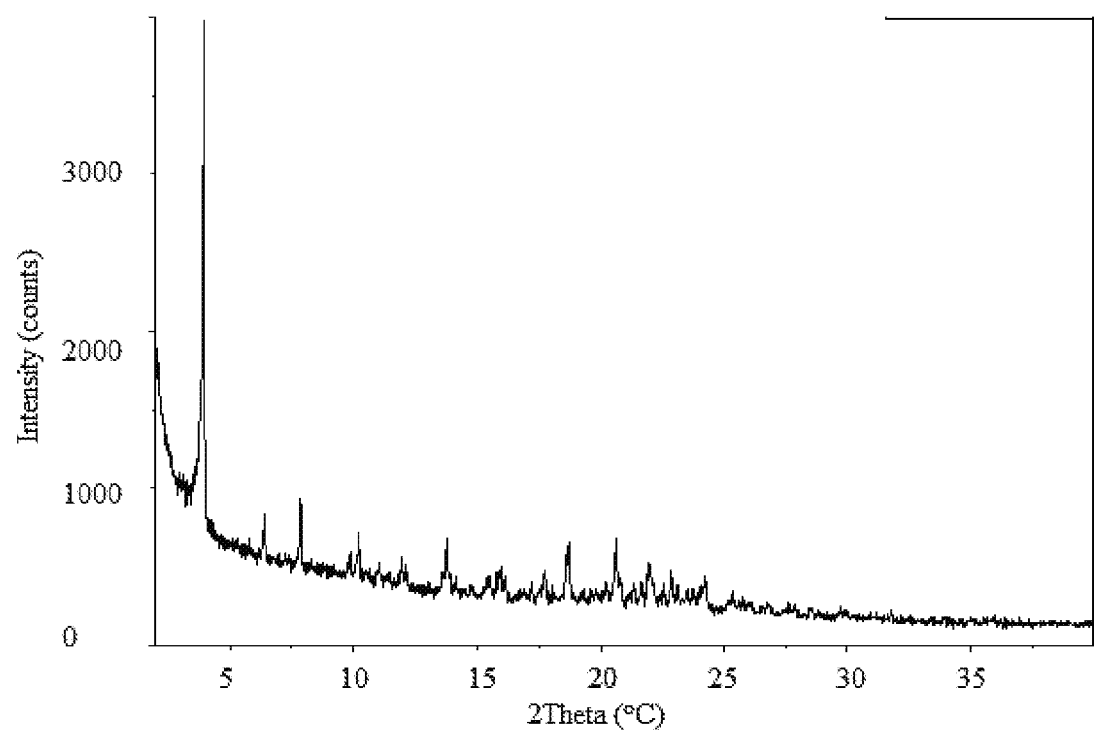
FIG. 3C is a PXRD (powder X-ray diffraction) of Compound 1 Form A as discussed in Example 4. The x-axis is 2Theta measured in degrees and the y-axis is intensity measured in counts.
Figure 3D:
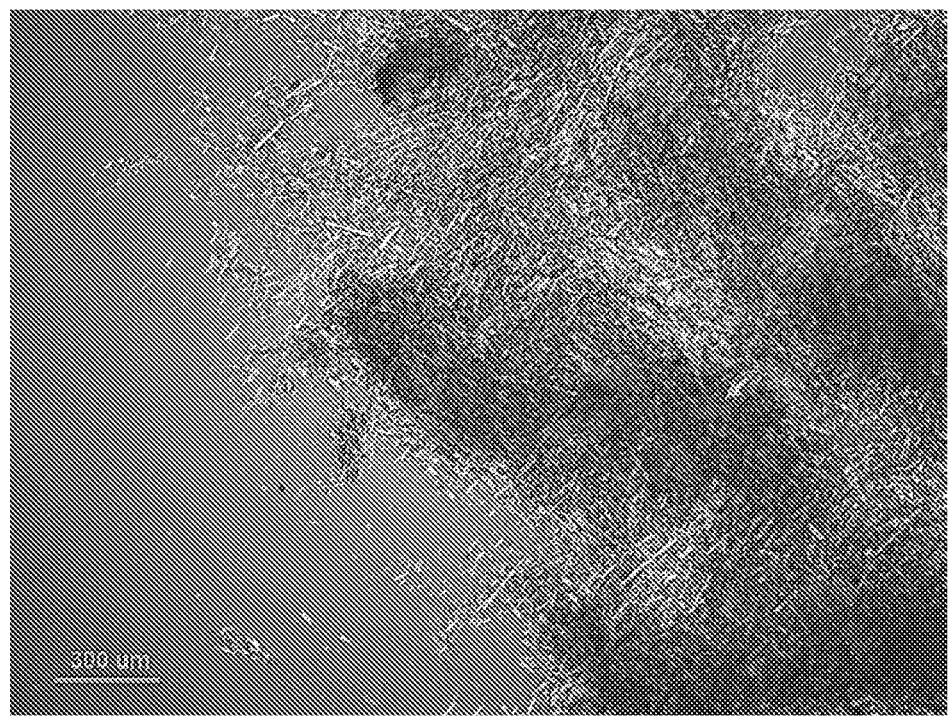
FIG. 3D is a PLM image of Compound 1 Form A as discussed in Example 4.

Form A is a crystal form precipitated from a solution in PEG300 during an excipient solubility study of Compound 1. Form A was not observed during the crystallization study of Example 3, but the crystal form was characterized by PXRD, FT-Raman, PLM, DSC, and TGA-IR. The physicochemical data of Form A are presented in FIG. 3A, FIG. 3B, FIG. 3C and FIG. 3D. Form I is crystalline by PXRD (FIG. 3C) and PLM (FIG. 3D). DSC shows a low energy broad endotherm at 68.6° C. and 2.4% (0.8 eq.) weight loss from water is observed from 25° C.-150° C. by TGA-IR (FIG. 3B).

Compound 1 Form II (Monohydrate)

Form II is a monohydrate form observed in the crystallization study of Example 3. A lower crystallinity sample of Form II was also found in an evaporation experiment from ethanol.

Form II was prepared by adding amorphous Compound 1 (82.1 mg) to a 4-mL vial containing a tumble-stir disk. Heptane (1 mL) and ethanol (1 mL) were added along with 2 mg of Form II seeds (CS-19). The suspension was stirred while cycling the temperature between 40° C. and 5° C. for 3 days. The suspension was filtered and then dried under vacuum for 20 minutes.

The physicochemical data of Form II are presented in FIG. 4A, FIG. 4B, FIG. 4C, FIG. 4D, and FIG. 4E. Form II is crystalline by PLM (FIG. 4D) and PXRD (FIG. 4C) and contains 2.7% bound water (~0.9 eq) which is released with a broad endotherm in the DSC from 40-125° C. (FIG. 4B). A final melting endotherm is observed at 155.3° C. Heating Form II past the dehydration endotherm and returning to room temperature does not change the crystal-form by PXRD or water content by TGA, indicating it is a reversible hydrate. Furthermore, DVS analysis conducted on the material (FIG. 4E) indicates the hydrate exists with ~2.7-4.0% water and shows a critical RH step at 30% RH which supports the data indicating that Form II reversibly hydrates.

Compound 1 Form III

Figure 5:
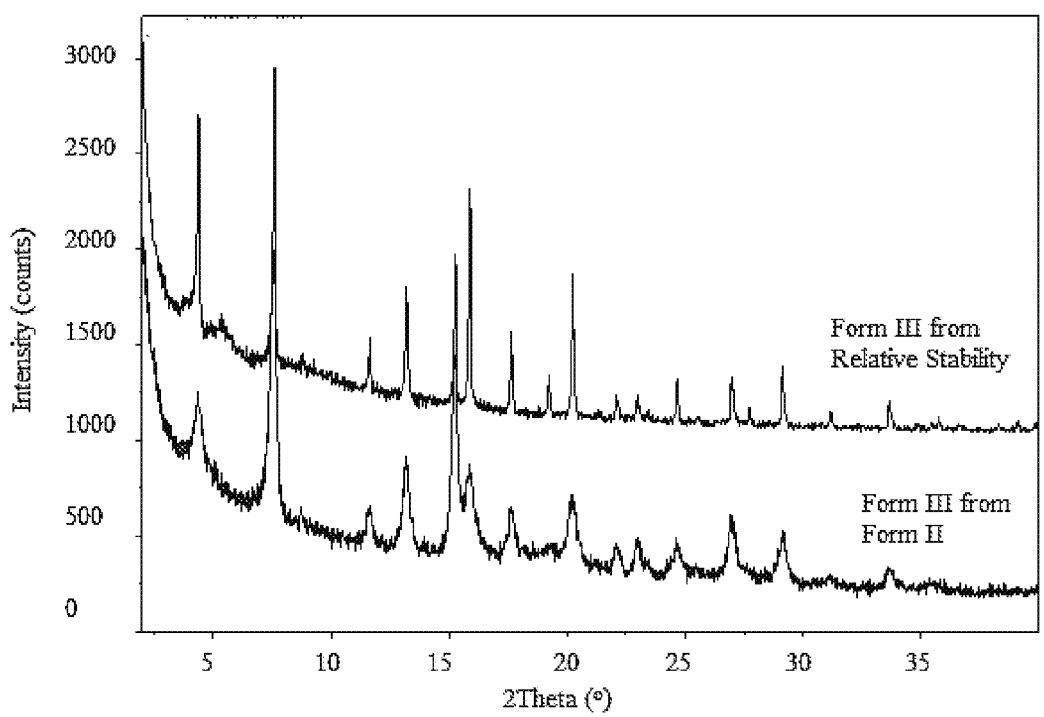
FIG. 5 is an overlay of PXRD patterns comparing Compound 1 Form III obtained from the crystallization of Compound 1 Form II (discussed in Example 4) and Compound 1 Form III observed during the relative stability experiments of Example 5. The x-axis is 2Theta measured in degrees and the y-axis is intensity measured in counts.

Form III is a crystal form observed from the residual solids of a sample of Form II stirred in water for 4 days. Form III was also observed during relative stability experiments (Example 5) with higher crystallinity than the batch observed from the residual solids of a sample of Form II (FIG. 5).

Figure 6B:
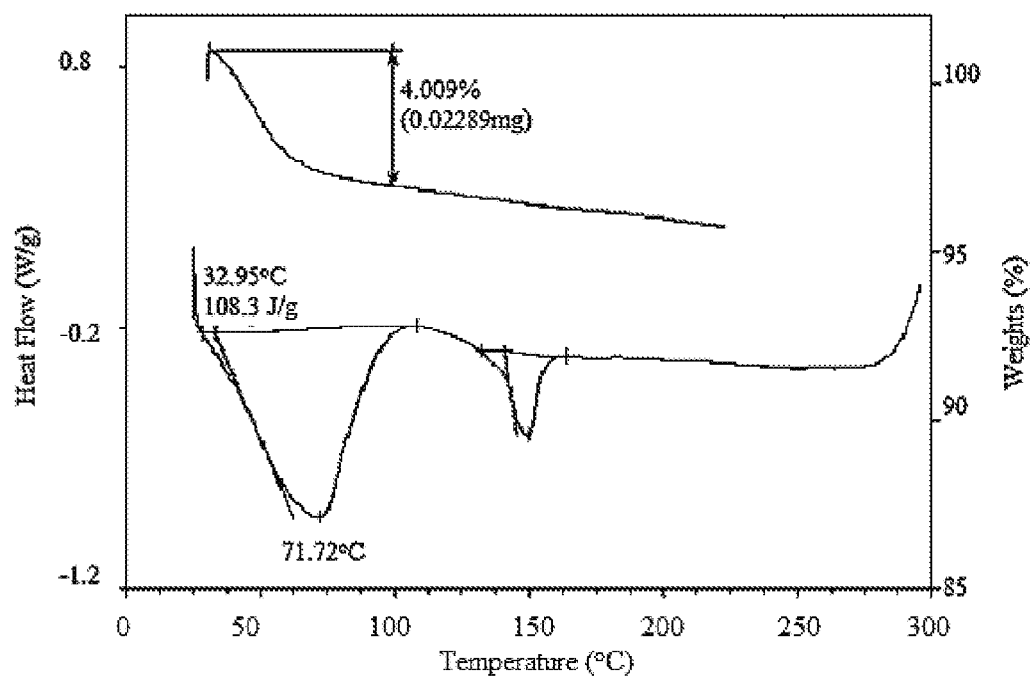
FIG. 6B is a DSC and a TGA graph of Compound 1 Form III as discussed in Example 4. The x-axis is temperature measured in ° C., the left y-axis is heat flow measured in (W/g), and the right y-axis is weight measured in percent.

The physicochemical data of Form III is presented in FIG. 6A and FIG. 6B. Form III is crystalline by PXRD (FIG. 6A) and contains 4.0% bound water (~1.3 eq) which is released with a broad endotherm in the DSC from 40-125° C. (FIG. 6B). A final endotherm is observed at 141.0° C. Drying Form III at 70° C. under vacuum for 1 hour did not change the crystal-form Compound 1 Form IV Form IV is a hydrated form observed in one sample that was filtered from PEG400.

Figure 7A:
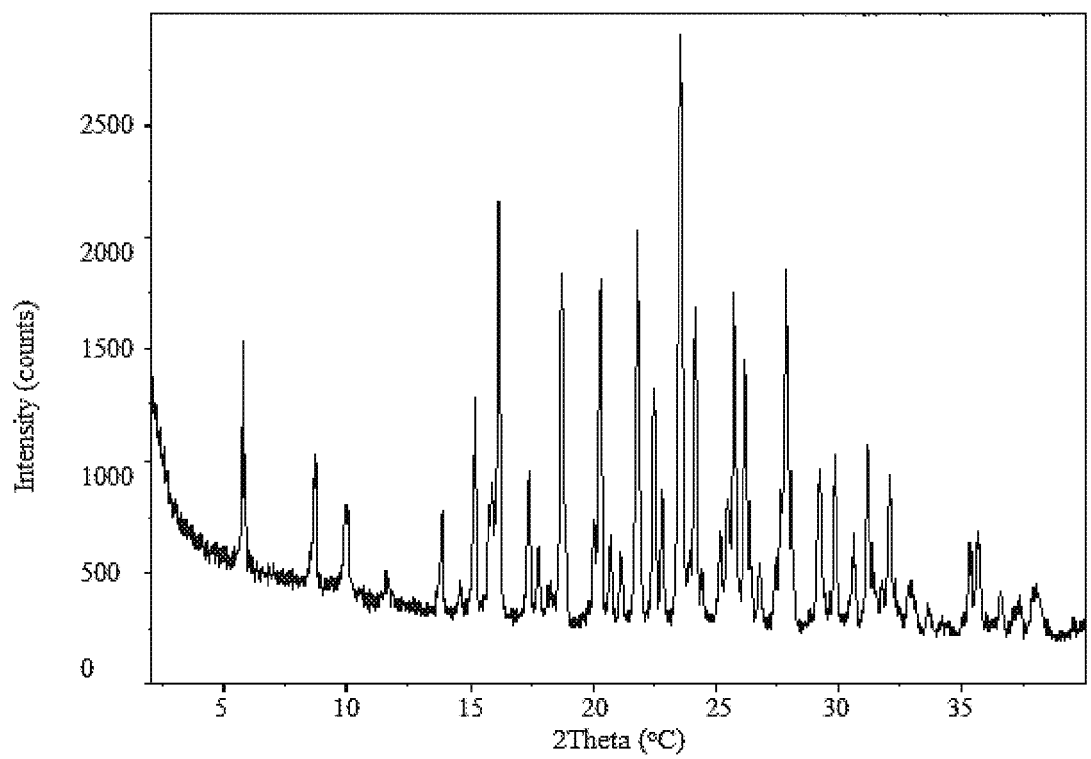
FIG. 7A is a PXRD (powder X-ray diffraction) of Compound 1 Form IV as discussed in Example 4. The x-axis is 2Theta measured in degrees and the y-axis is intensity measured in counts.
Figure 7B:
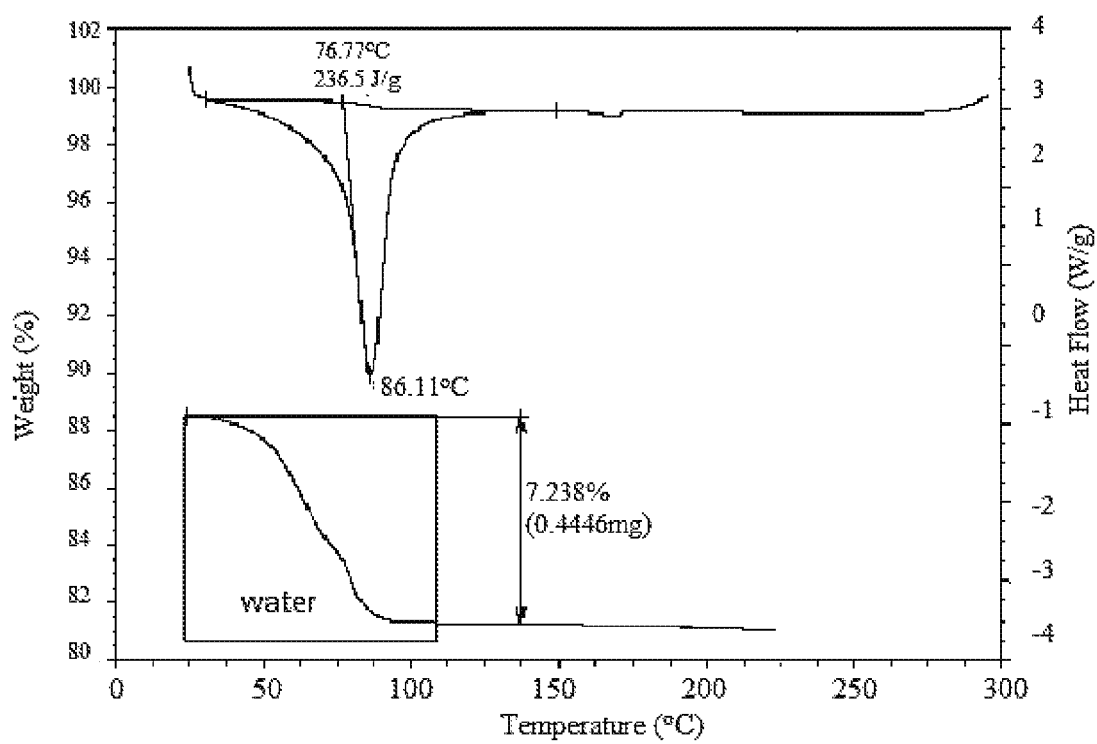
FIG. 7B is a DSC and a TGA graph of Compound 1 Form IV as discussed in Example 4. The x-axis is temperature measured in ° C., the left y-axis is heat flow measured in (W/g), and the right y-axis is weight measured in percent.

The physicochemical data of Form IV is presented in FIG. 7A and FIG. 7B. Form IV is crystalline by PXRD (FIG. 7A) and contains 7.2% bound water (~2.5 eq) which is released with an endotherm in the DSC at 76.8° C. (FIG. 7B). Form IV is physically stable in sealed vial for at least 10 days by PXRD.

Compound 1 Form V

Form V is a hydrated form observed during a scale-up attempt of Form IV.

Form V was prepared by adding amorphous Compound 1 (30 mg) to methanol/10 vol % water (500 uL) at 25° C. and stirring for 10 minutes. A clarifying filtration was performed into clean HPLC vial. Seeds of Form IV (1 mg) were added and stirred at 25° C. Clouding occurred after a few minutes. Solids were isolated after 30 minutes of stirring at 25° C. (thick slurry).

Figure 8B:
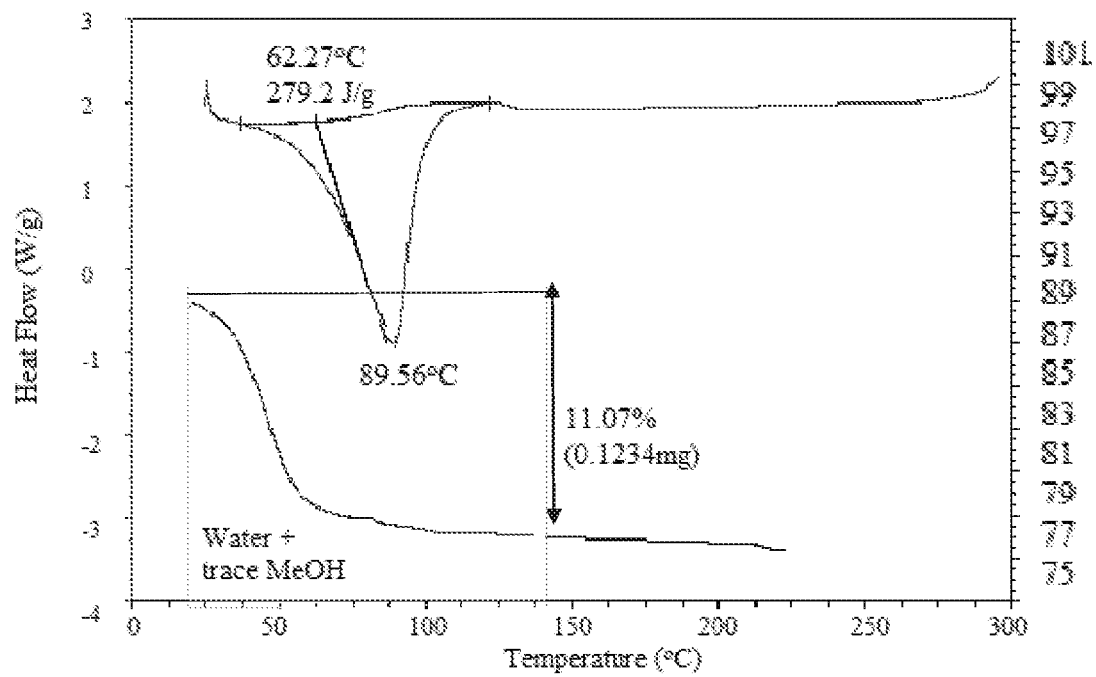
FIG. 8B is a DSC and a TGA graph of Compound 1 Form V as discussed in Example 4. The x-axis is temperature measured in ° C., the left y-axis is heat flow measured in (W/g), and the right y-axis is weight measured in percent.

The physicochemical data of Form V is presented in FIG. 8A and FIG. 8B. Form V is crystalline by PXRD (FIG. 8A) and contains 11.1% water (~4.0 eq) and a trace amount of methanol. DSC shows a broad endotherm at 62.3° C. (FIG. 8B). The thermal analysis data does not definitively indicate whether the water and methanol are bound or residual. Further studies on Form V are required (e.g. drying).

Compound 1 Form VI

Form VI is a mixed water/acetone solvate form observed during a scale-up attempt of Form IV.

Form VI was prepared by adding amorphous Compound 1 (30 mg) to acetone:water (3:2, 500 uL) at 25° C. and stirring for 10 minutes. A clarifying filtration was performed into clean HPLC vial. Seeds of Form IV (1 mg) were added and stirred at 25° C. Clouding occurred after a few minutes.

Figure 9A:
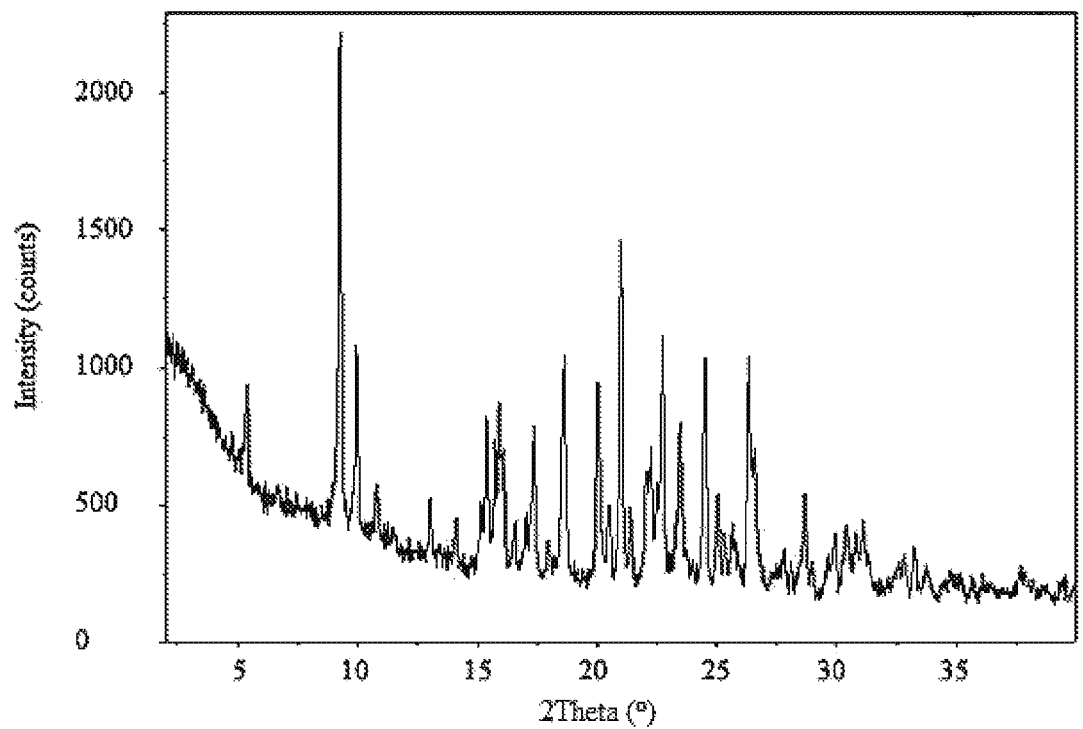
FIG. 9A is a PXRD (powder X-ray diffraction) of Compound 1 Form VI as discussed in Example 4. The x-axis is 2Theta measured in degrees and the y-axis is intensity measured in counts.
Figure 9B:
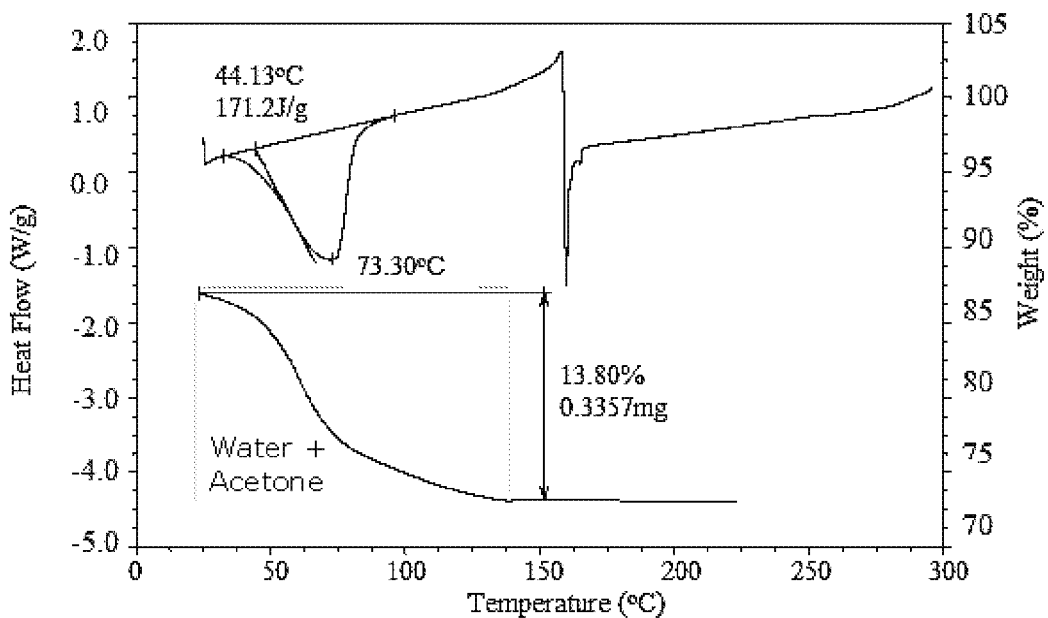
FIG. 9B is a DSC and a TGA graph of Compound 1 Form VI as discussed in Example 4. The x-axis is temperature measured in ° C., the left y-axis is heat flow measured in (W/g), and the right y-axis is weight measured in percent.
Figure 10A:
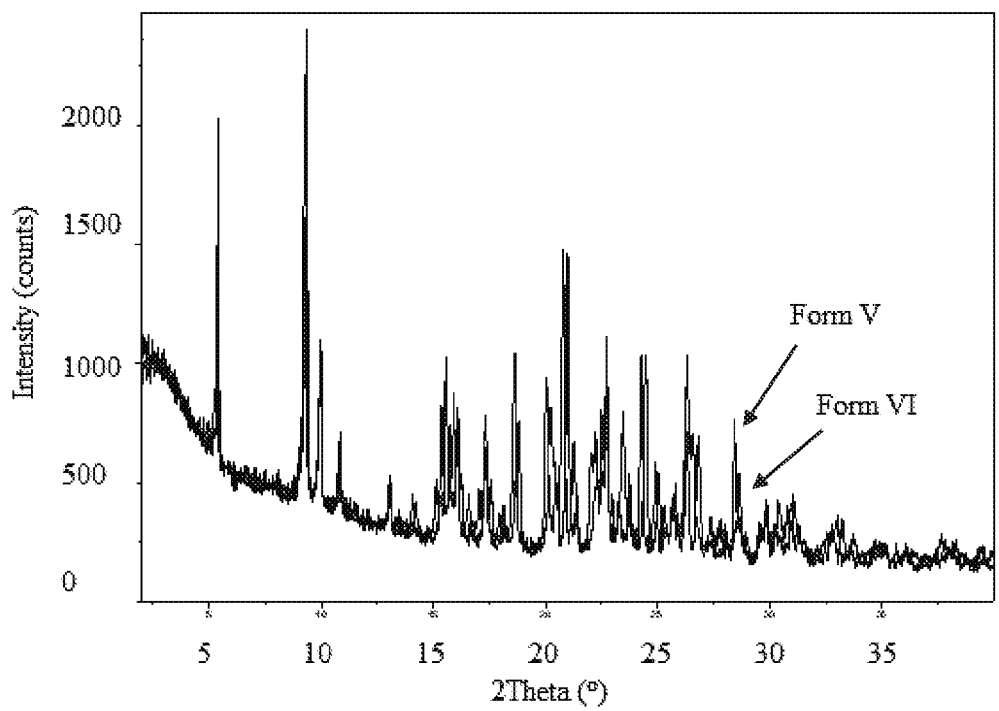
FIG. 10A is an overlay of PXRD patterns comparing Compound 1 Form V and Compound 1 Form VI as discussed in Example 4. The two PXRD patterns share significant overlap.
Figure 10B:
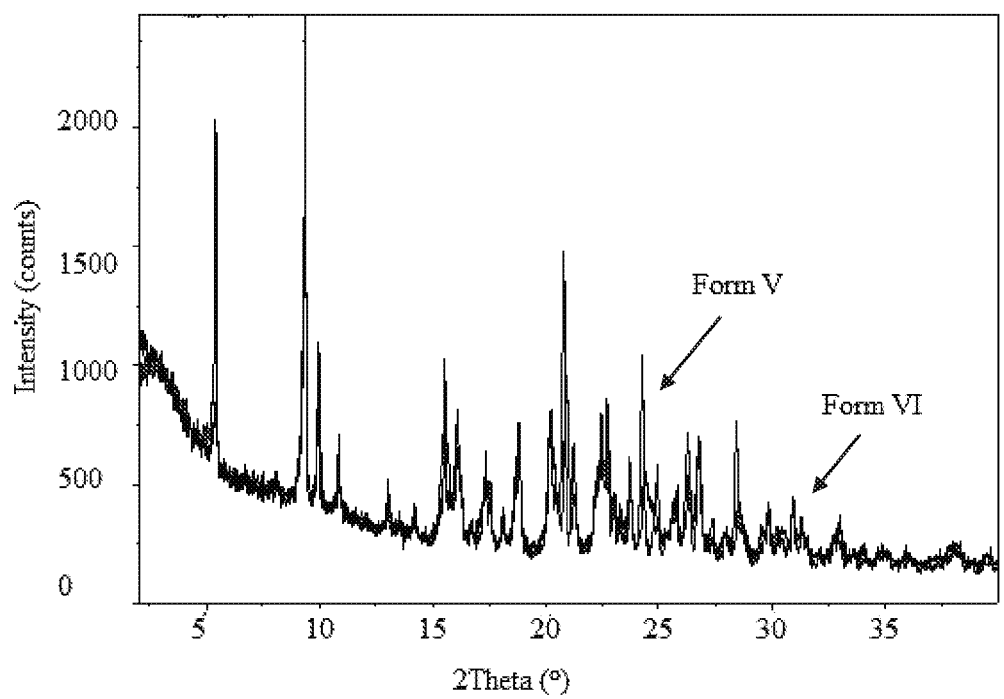
FIG. 10B is an overlay of PXRD patterns comparing Form Compound 1 V and Compound 1 Form VI after exposure to ambient temperature overnight as discussed in Example 4. The two PXRD patterns share significant overlap.

The physicochemical data of Form VI is presented in FIG. 9A and FIG. 9B. Form VI is crystalline by PXRD (FIG. 9A) and contains 13.8% bound water and acetone which is released with a broad endotherm in the DSC at 44.1° C. (FIG. 9B). The PXRD pattern of Form VI is similar to Form V as shown in FIG. 10A. After sitting overnight on a PXRD holder, Form VI closely resembles Form V as shown in FIG. 10B.

Compound 1 Form VII

Form VII is a mixed water/IPA solvate form observed from a sample submitted for single crystal analysis.

Figure 11A:
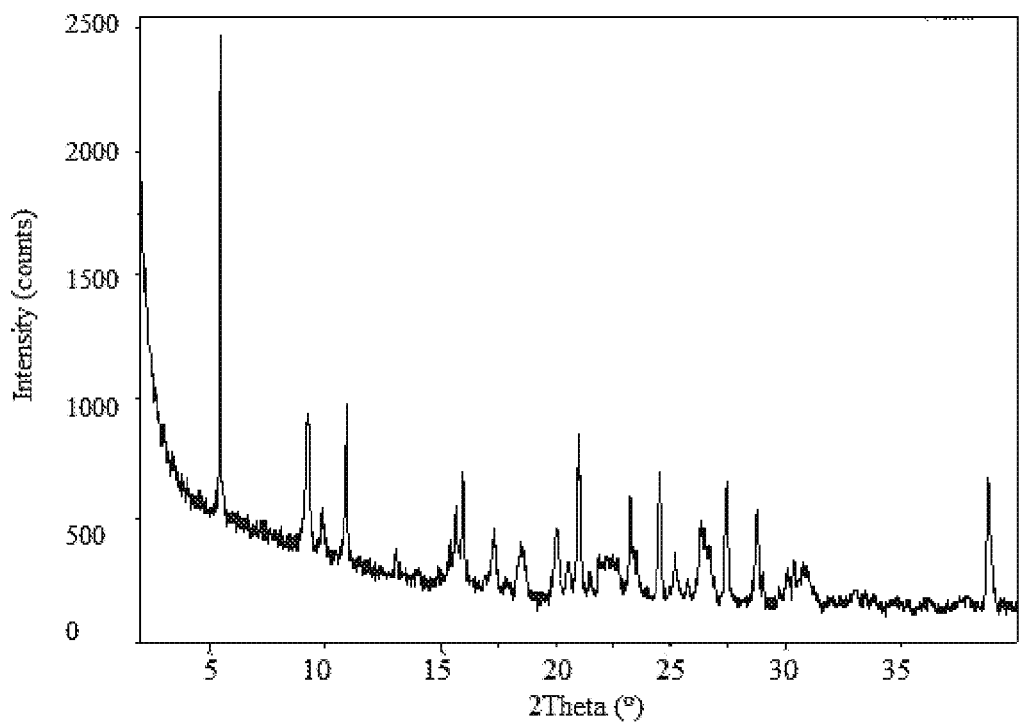
FIG. 11A is a PXRD (powder X-ray diffraction) of Compound 1 Form VII as discussed in Example 4. The x-axis is 2Theta measured in degrees and the y-axis is intensity measured in counts.
Figure 11B:
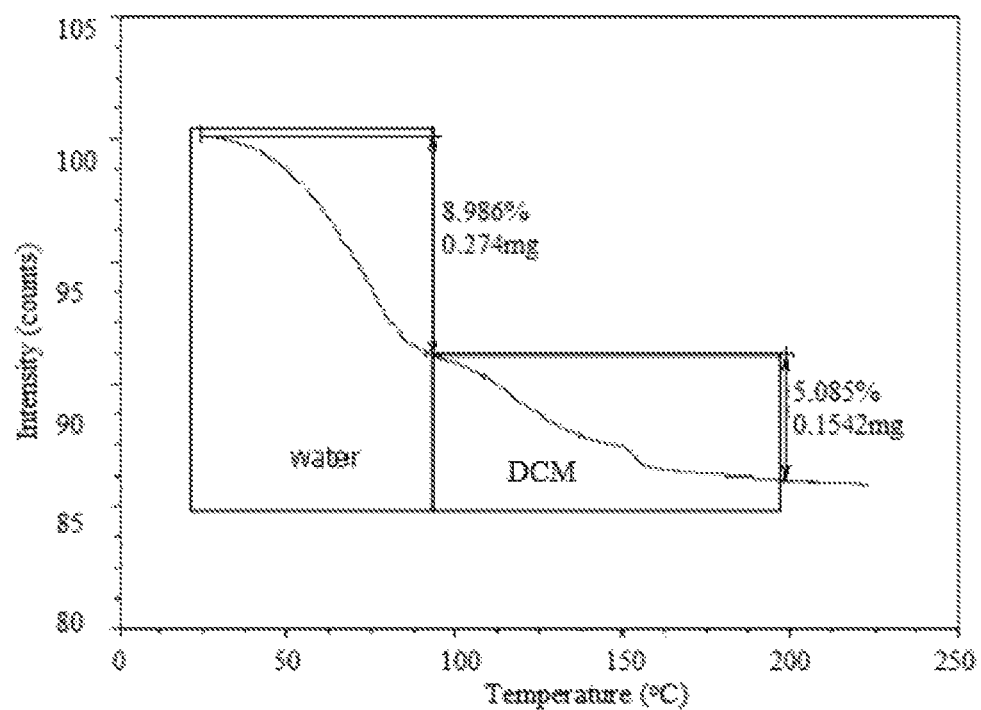
FIG. 11B is a TGA-IRA trace of Compound 1 Form VII as discussed in Example 4. The x-axis is temperature measured in ° C. and the y-axis is weight measured in percent.
Figure 12:
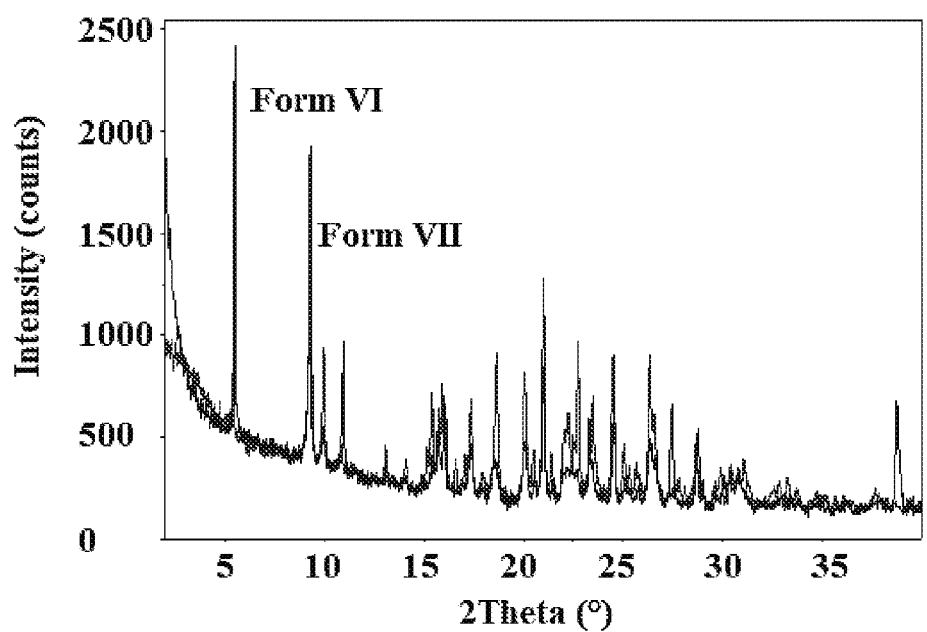
FIG. 12 is an overlay of PXRD patterns comparing Compound 1 Form VI and Compound 1 Form VII as discussed in Example 4. The two PXRD patterns share significant overlap indicating that Compound 1 Form VII is likely a mixed solvate containing water and IPA.

The physicochemical data of Form VII is presented in FIG. 11A and FIG. 11B. Form VII is crystalline by PXRD (FIG. 11A) and contains 14.0% water and IPA by TGA-IR (FIG. 11B). The PXRD pattern of Form VII is similar to Form VI as shown in FIG. 12 indicating that the material is likely a mixed solvate containing water and IPA.

Example 5

Relative Stability of Compound 1 Form II, Form IV, and Form V

The relative stability of hydrated Compound 1 Form II, Form IV, and Form V were studied at 25° C. and the results are shown in Table 6. Form II was shown to be the stable hydrate at or below a water activity value (aw) of 0.55 (at 25° C.). Form V was determined to be the stable hydrate at aw=0.75, with Form III the stable hydrate at aw=0.90. The water activity of the solvent mixture used for the crystallization process must be below 0.55 in order to obtain Form II consistently.

TABLE 6

Results of Relative Stability Experiments

| Sample ID | Solvent System | Water Activity | PXRD Results 4 days/RT | PXRD Results 8 days/RT |
|---|---|---|---|---|
| CR1 | 2-propanol | 0 | Form II | N/A |
| CR2 | EtOAc | 0 | Form II | N/A |
| CR3 | Methanol: 10 vol % Water | 0.33 | Form II | N/A |
| CR4 | 2-propanol: 5 vol % Water | 0.55 | Form II | N/A |
| CR5 | Acetonitrile: 10 vol % Water | 0.75 | Form V | Form V |
| 102097-CR6 | 2-propanol: 20 vol % Water | 0.9 | Form III | Form IH |

Example 6

Synthesis of Compound 2 Form I

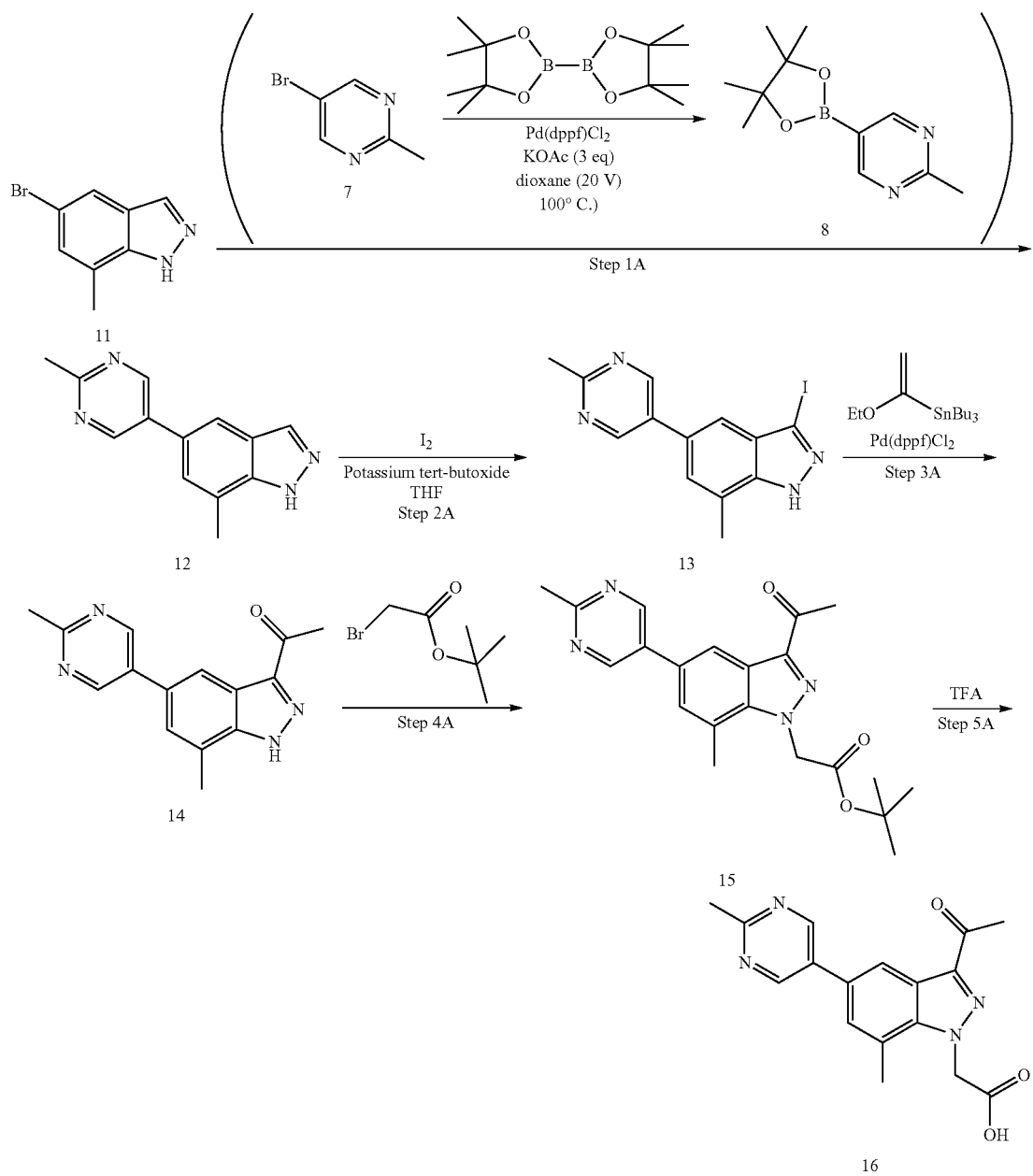

Scheme 2. Synthesis of Intermediate 16

Step 1A: Suzuki coupling: Bromo methyl pyrimidine (11, 10 Kg, 1 eq) was dissolved in 1,4-dioxane (200 Kg, 20 vol.) and bispinacolato diborane (14.7 Kg, 1 eq) and potassium acetate (17 Kg, 3 eq) were added. The reaction was degasified for 15 minutes with $N_2$ for 30 minutes and Pd(dppf)Cl$_2$ (1.4 Kg, 0.03 eq) was added. The reaction was again degasified for 15 minutes and stirred for 2 hours at 95±5° C. The reaction was then cooled to 25±5° C. and charged with bromo-7-methyl-1H-indazole (7, 9.15 Kg, 0.8 eq), K$_2$CO$_3$ (23.9 Kg, 3 eq). The reaction was degasified for 15 minutes and stirred for 2 hours at 95±5° C. The reaction mass was cooled to 25±5° C., diluted with 10% methanol in DCM (20 vol), charged with charcoal (0.1 w/w), stirred for 30 minutes, and filtered through a celite bed. The filtrate layers were separated and the aqueous layer was extracted with 10% methanol in DCM (10 vol.). The combined organic layer was washed with water (20 w/w×2 times) and the organic later was concentrated and co-evaporated with n-heptane (2 vol.). The mass was stirred with n-heptane (10 vol.) at 45±5° C. for 60 minutes and then at 10±5° C. for an additional 60 minutes before being filtered. The bed was washed with a mixture of n-heptane (0.74 w/w) and n-heptane (1.92 w/w) to afford intermediate 12 (yield: 7.31 Kg)

Step 2A: Iodination: Intermediate 12 (11.5 Kg, 1 eq) was dissolved in THF (95.7 Kg, 10 vol) and heated to 60±5° C. to obtain a clear solution. The mass was cooled to 0-5° C. and iodine (19.55 Kg, 1.5) was added followed by potassium tert-butoxide (14.35 Kg, 2.5 eq) lot-wise and the reaction mass was stirred for 1 hour at room temperature. The reaction mass was quenched with 10% sodium thiosulphate solution (15 vol) and 10 vol water was added into the reaction mass at room temperature. The reaction was stirred for 8 hours and the resulting solid was filtered to afford intermediate 13 (Yield: 13.41 Kg. yield 74.7%).

Step 3A: N-Acetylation: A reaction flask was charged with DMF (174.3 Kg, 14 vol) and intermediate 13 (13.2 Kg, 1 eq) and the reaction was heated to 55° C. to 60° C. to obtain a clear solution. The reaction was cooled to 25° C. and ethoxyvinyl stannate (61.25 Kg, 4.5 eq) was added under nitrogen. The reaction was then degasified for 10-15 minutes under a $N_2$ atmosphere before Pd(dppf)Cl$_2$·DCM (3.07 Kg, 0.02 eq) was added and the reaction was stirred for 2 hours at 80° C. The reaction mass was quenched with 3M HCl (50 w/w) and stirred for 2 hours. Ethyl acetate (10 vol) was added and the mass was stirred for 30-35 minutes and filtered through a celite bed. The layers were separated and the resulting aqueous layer was washed with ethyl acetate (5 vol) and basified with solid NaHCO$_3$. The aqueous layer was further washed with ethyl acetate (10 vol) twice and the combined organic layers were washed with water (10 vol) twice and concentrated. n-Heptane (5 Vol) was added and the residue stirred for 1 hour before being filtered to afford intermediate 14 (Yield: 6.21 Kg, yield 61.85%)

Step 4A: N-Alkylation: Intermediate 14 (6.25 Kg, 1 eq) was taken up in DMF (58.3 Kg, 7 vol) and K$_2$CO$_3$ (9.61 Kg, 3 eq) was added at 25±5° C. Tert-butyl bromoacetate (5.0 Kg, 1.2 eq) was added slowly and the reaction mass was stirred for 2 hours at 50±5° C. The reaction mass was cooled to 15±5° C., quenched with water (22 vol.), and stirred for 3 hours at 25±5° C. The resulting solid was filtered and washed with water (5 vol.). The crude material was purified with 10% ethyl acetate in n-heptane to afford intermediate 15 (Yield: 7.11 Kg, yield 80%)

Step 5A (Ester Hydrolysis): A reaction flask was charged with DCM (93.1 Kg, 10 vol) and intermediate 15 (7 Kg, 1 eq). The reaction was cooled to 15±5° C. and TFA (52.1 Kg, 5 vol) was slowly added at 15±5° C. The temperature was raised to 35±5° C. and the reaction was stirred for 2 hours at 35±5° C. DCM and TFA removed under reduced pressure and the resulting crude material was dissolved in DCM (10 vol.). 10% NaHCO$_3$ solution (20 vol.) was slowly added to adjust the pH to 7.5-8. The aqueous layer was stirred for 1 hour and the pH was adjusted to 2-3 using concentrated HCl. The resulting solid was filtered, washed with water (2 vol.), and vacuum-dried at 55±5° C. for 12 hours to afford intermediate 16 (Yield: 5.11 Kg, yield 85.59%).

Scheme 3. Synthesis of Intermediate 26

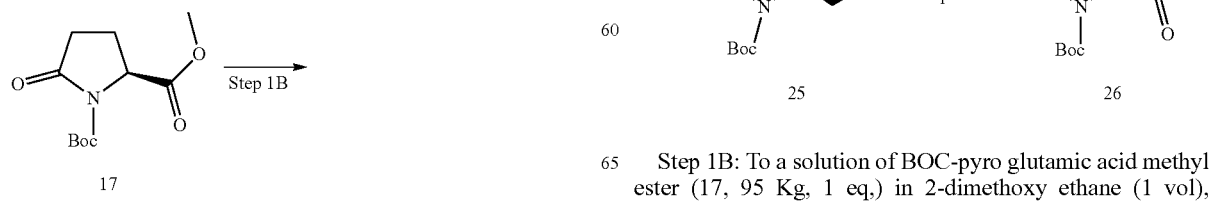

Step 1B: To a solution of BOC-pyro glutamic acid methyl ester (17, 95 Kg, 1 eq.) in 2-dimethoxy ethane (1 vol), Bredereck reagent (95 Kg, 1.05 eq.) was added. The mass was stirred for 4 hours at 75°±5° C. After the completion, the mass was cooled to 25±5° C. and n-heptane (5 vol) was added. The mass was further cooled mass to 0±5° C. and stirred for 2-3 hours. The resulting solid was filtered and washed with n-heptane. The crude material (18) was used in the next step.

Step 2B: Crude material (18) was dissolved in IPA (5 vol) and Pd/C (0.1 w/w, 9.5 Kg) was added lot-wise. The reaction was stirred for 14 hours at 55±5° C. After completion, the reaction was cooled to 25±5° C., filtered and washed with IPA. The filtered layer was concentrated, n-heptane (3 vol) was added, and the solution was cooled to 0±5° C. and stirred for 1 hour. The resulting solid was filtered and dried to afford intermediate 19 (Yield: 87.2 Kg; 86.8%).

Step 3B: To a solution of intermediate 19 (1 eq, 75 Kg) in toluene (10 vol), lithium triethylborohydride (abt. 20% in THF) (123 Kg) was added at −60±5° C. and the reaction was stirred for 1 hour. After completion, methanol (2.5 vol) was added followed by water (10 vol). The aqueous layer was extracted with ethyl acetate (10 vol) and the combined organic layers were washed with brine solution and concentrated to afford 80 Kg of crude 20.

Step 4B: Intermediate 20 was dissolved in toluene (10 vol) and 2,6-lutidine (1.5 eq, 46.6 Kg) was added at 0±5° C. Trifluoroacetic anhydride (1 eq, 61.5 Kg) was added at 0±5° C. and the reaction mixture was heated to 50±5° C. and stirred before the temperature was raised to 25±5° C. and quenched with water (10 vol). The aqueous layer was extracted with ethyl acetate (10 vol) and the combined organic layers were washed with brine solution and concentrated. Crude material was purified by column chromatography using ethyl acetate/n-heptane to afford 53.8 Kg of crude 21.

Step 5B: Intermediate 21 was dissolved in THF:ethanol (1:1.5, 25 vol) and sodium borohydride (5 eq, 23.5 Kg+0.314 Kg) was added lot-wise followed by lithium chloride (3 eq, 26.5 Kg+0.314 Kg) lot-wise at 25±5° C. The reaction was stirred for 2 hours at 25±5° C. After completion, the mass was cooled to 0±5° C., quenched with water (10 vol), and concentrated. The mass was further diluted with water (5 vol) and ethyl acetate was added. The mass was filtered through a celite bed and the aqueous layer was washed with ethyl acetate (10 vol×1). The combined organic layers were washed with water (10 vol) and brine solution (5 vol), dried over sodium sulphate, filtered and concentrated to afford intermediate 22.

Step 6B: Intermediate 22 was dissolved in DCM (10 vol) and the reaction was cooled to 0±5° C. DMAP (0.1 eq, 2.24 Kg), TEA (2.5 eq, 65 Kg) and benzoyl chloride (1.05 eq, 37.4 Kg) were added and the temperature was raised to 25±5° C. and stirred for 2 hours. After completion, DCM (10 vol) and water (10 vol) were added. The organic material was washed with water and concentrated. The crude material was purified by column chromatography using ethyl acetate and n-heptane to afford intermediate 23 (Yield: 63.2 Kg; overall yield 51%)

Step 7B: Intermediate 23 (1 eq, 62 Kg) was dissolved in toluene (20 vol) and the mass was cooled to −25 to −30° C. 1.5M Diethyl zinc in toluene (2.5 eq, 262 Kg) was added and the reaction was stirred for 30 minutes at 25 to −30° C. Chloroiodomethane (6 eq, 180 Kg) was added and the reaction was stirred for an additional 30 minutes at 25 to −30° C. The reaction mass temperature was raised to −2±5° C. and stirred for 4 hours. After completion, the reaction mass was cooled to −10±5° C., quenched with 10% sodium bicarbonate solution (10 vol), stirred for 10-15 minutes at 25±5° C., filtered, and washed with ethyl acetate. The organic layer was washed with brine and concentrated to afford intermediate 24.

Step 8B: Intermediate 24 was dissolved in methanol and the reaction was cooled to 0±5° C. Sodium methoxide (1.1 eq, 38.5 Kg) solution was added and the reaction was stirred at 25±5° C. for 2 hours. After completion, the reaction was cooled to 5±5° C., quenched with water (10 vol) and stirred for 8 hours. The methanol was concentrated and the aqueous layer was extracted with ethyl acetate (10×2). The combined organic layers were washed with brine solution and concentrated to afford intermediate 25 (Yield: 34.9 Kg; overall yield 81%)

Step 9B: Intermediate 25 (1 eq, 34.9 Kg) was dissolved in acetonitrile (154 kg, 5 vol) and monosodium phosphate in water solution (2.5 w/w in water, 87.25 Kg) and TEMPO (0.12 eq, 2.44 Kg) were added at 25±5° C. Sodium chlorite (2.9 eq, 36.65 Kg) in water and sodium hypo chloride solution (0.36 vol, 10.5 Kg) was added simultaneously at 35° C. or below and the reaction was stirred for 8 hours below 35° C. After completion, the reaction was cooled to 20±5° C. and 20% sodium sulphite solution (4 w/w 69.8 Kg) was added. The pH was adjusted to 9 using 2M NaOH solution and the mass was washed with MTBE (5 vol×2). The aqueous layer pH was adjusted to 2-3 using 2M HCl solution and extracted with DCM (10×3). The organic layers were washed with water, concentrated and co-distilled with THF. Crude material was dissolved in THF (5 vol) and benzyl amine (0.5 w/w) in THF was added at 10±15° C. The reaction was stirred for 12 hours and then cooled to 0±5° C. and stirred for 1 hour. The resulting solid was filtered and washed with THF (5 vol). The solid was dissolved in DCM (15 vol) and washed with 1.5 M HCl solution (10 vol×2). The organic layer washed with 5% sodium chloride solution and concentrated to afford intermediate 26 (Yield: 21.32 Kg; 57.56%)

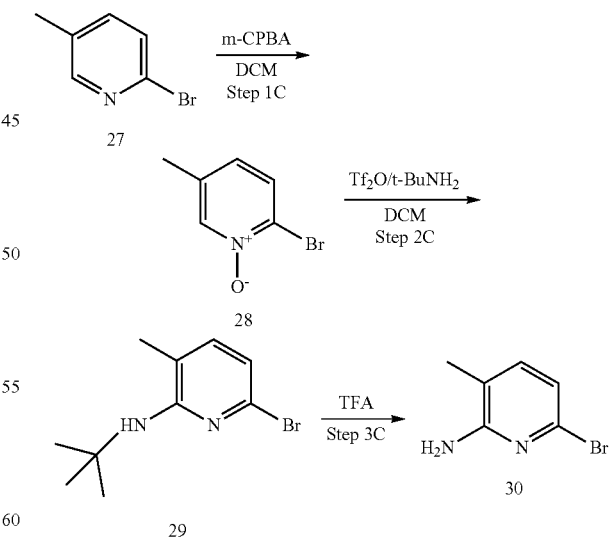

Scheme 4. Synthesis of Intermediate 30

2-Bromo-5-methylpyridine (27, 1 w/w, 14.0 Kg) was added to DCM (10 vol.) and the reaction was stirred for 10 minutes before 3-chloroperbenzoic acid (1.8 w/w, 25.2 Kg) was added and the reaction was stirred for 2 hours at 25±5° C. Purified water (20 w/w) was added and the reaction mass was concentrated. THF (5 vol.), ethyl acetate (5 vol.) and n-heptane (10 vol.) were added to the water layer and the water layer was stirred for 30 minutes. The layers were separated and the aqueous layer was extracted with a THF (5 vol.)/n-heptane (5 vol.) mixture. The combined organic layers were washed with purified water (20 w/w and with 10 w/w). Sodium thiosulfate (10 w/w, 140.0 Kg) was added to the aqueous layer and it was stirred for 10 minutes before sodium chloride (15 w/w, 150.0 Kg) was added and the solution was stirred for an additional 10 minutes. DCM (20 vol.) was then added and the resulting solution was stirred for 15 minutes. Following separation of the two phases, the aqueous layer was extracted with DCM (20 vol.). The combined organic layers were dried over anhydrous sodium sulphate, filtered, and washed with DCM (3 vol.).

The filtrate was concentrated and the resulting mass was dissolved in DCM (10 vol.) at 25±5° C. The solution was then cooled to −25±5° C. and tert-butyl amine (2.97 w/w, 41.58 Kg) was slowly added. The reaction was stirred for 10 minutes before trifluoromethane sulphonic anhydride (9.84 w/w, 137.76 Kg) was added and the reaction was stirred for an additional 2 hours at −25±5° C. After completion, purified water (20 w/w) was slowly added at −20±5° C. and the solution was stirred at 25±5° C. for 15 minutes. The aqueous layer was extracted with DCM (15 vol.) and the organic layer was washed with the 30% K$_2$CO$_3$ solution (purified water 14 w/w, K$_2$CO$_3$ 6.0 w/w, 84.0 Kg) and NaCl solution (purified water 9 w/w, NaCl 1.0 w/w, 14.0 Kg) at 25±5° C.

The organic layer was concentrated and the resulting solid was cooled to 25±5° C. before TFA (7.45 w/w, 104.3 Kg) was added. The reaction stirred for 6 hours at 65±5° C. The reaction was then concentrated and co-evaporated with DCM (5 vol.). The resulting mass was cooled to 25±5° C. and DCM (10 vol.) and 20% K$_2$CO$_3$ solution (purified water 9.6 w/w, K$_2$CO$_3$ 6.0 w/w, 2.4 Kg) were added at 25±5° C. The resulting solution was stirred for 10 minutes. The aqueous layer was extracted with DCM (10 vol.) and the resulting mass was concentrated and purified via column chromatography using n-heptane and ethyl acetate as the mobile phase. The cartridge-filtered product fractions were concentrated and co-evaporated with cartridge-filtered n-heptane (0.7 vol.). The resulting solid was cooled to 25±5° C. and cartridge-filtered n-heptane (0.73 vol.) was added. The solution was again cooled to 7±3° C., stirred for 40 minutes, filtered, and washed with n-heptane (0.29 vol.). Additional Acid Base Purification Procedure:

Crude material was added to HCl solution (4.07 w/w purified water, 4.72 w/w HCl) and the solution was stirred for 10 minutes before DCM (10 vol.) was added. The aqueous layer was extracted with DCM (5 vol.) and the organic layer was washed with 2.69 w/w of HCl solution. The aqueous layer was extracted with DCM and NaHCO$_3$ (6.1 w/w) was added to adjust the pH to 7-8 before DCM was added. The resulting aqueous layer was extracted with DCM (10 vol.×3 times) and the combined organic layers were concentrated.

Scheme 5. Modified Synthesis of Intermediate 23

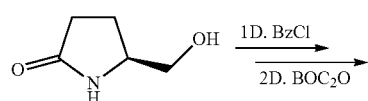

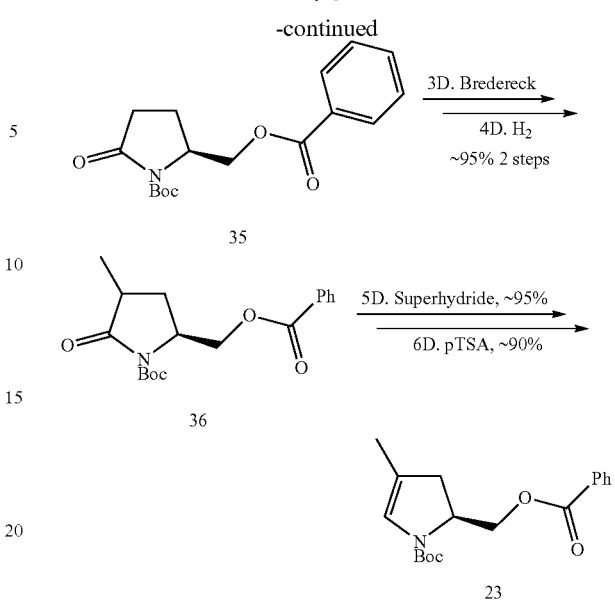

Step 1D: (5S)-5-(Hydroxymethyl)pyrrolidin-2-one (34, 15 g, 130.285 mmol, 1 equiv.), triethylamine (65.918 g, 90.796 mL, 651.426 mmol, 5 equiv.) and 4-dimethylaminopyridine (0.796 g, 6.514 mmol, 0.05 equiv.) in dichloromethane (200 mL, 0.434 M, 20 Vols) was cooled to 5° C. and benzoyl chloride (21.977 g, 18.147 mL, 156.342 mmol, 1.2 equiv.) was slowly added. The reaction was stirred for 3 hours at room temperature. The reaction mixture was quenched with saturated aqueous NaHCO$_3$ and stirred for another 30 minutes. The organic layer was separated, washed with water (×1), dried over sodium sulfate and evaporated to dryness. The residue was dissolved in warm AcOEt (100 mL) and heptane (100 mL) was slowly added. The solution was slowly cooled to room temperature, stirred for 1 hour at 5° C., and filtered to afford [(2S)-5-oxopyrrolidin-2-yl]methyl benzoate (28 g, 127.714 mmol, Yield 98.026%).

Step 2D: [(2S)-5-oxopyrrolidin-2-yl]methyl benzoate (23 g, 104.908 mmol, 1 equiv.), 4-dimethylaminopyridine (6.408 g, 52.454 mmol, 0.5 equiv.) in dichloromethane (230 mL, 0.456 M, 10 Vols) was cooled to 5° C. and di-tert-butyl dicarbonate (34.344 g, 36.152 mL, 157.362 mmol, 1.5 equiv.) was added. The reaction was stirred overnight at room temperature. The solvent was removed from the reaction mixture and heptane (100 mL) was added. The solution was stirred and the supernatant was decanted. The solid was dissolved in CH$_2$Cl$_2$ and washed with 1N HCl to remove DMAP. The DCM solution was evaporated to dryness, titurated with heptane (70 mL) and the solid filtered to afford tert-butyl (2S)-2-[(benzoyloxy)methyl]-5-oxopyrrolidine-1-carboxylate (35, 20.2 g, 63.252 mmol, Yield 99.053%)

Step 3D and 4D: Bredereck reagent was added twice to intermediate 35 (25 g) to yield 28.4 g (97%) of product that was subjected to hydrogenation conditions (overnight reaction in IPA at 50° C.). This resulted in 11.6 g (87% yield) of intermediate 36 after chromatographic purification. The material was solid and can be crystallized if needed.

Step 5D: To a stirred solution of tert-butyl (5S)-5-[(benzoyloxy)methyl]-3-methyl-2-oxopyrrolidine-1-carboxylate (36, 5 g, 14.998 mmol, 1 equiv.) in tetrahydrofuran (75 mL, 0.2 M, 15 Vols) was added lithiumtriethylborohydride (1.748 g, 16.497 mL, 16.497 mmol, 1.1 equiv.) at −78° C. under argon. The reaction mixture was stirred at −78° C. for 20-30 minutes and then quenched with a saturated NaHCO$_3$ solution at −78 to −70° C. The reaction mixture was warmed to −20° C. 30% hydrogen peroxide (5.612 g, 5.055 mL, 49.492 mmol, 3.3 equiv.) was added before further warming up to 0° C. over 15-20 minutes. The aqueous phase was extracted with AcOEt/saturated aqueous NaCl and the organic phase was washed with saturated aqueous NaCl. The aqueous layer was extracted again with CH$_2$Cl$_2$ twice and all organic layers were combined and concentrated. The residue was dissolved in CH$_2$Cl$_2$ and the aqueous layer was extracted three times with CH$_2$Cl$_2$, dried and concentrated to afford crude product, tert-butyl (5S)-5-[(benzoyloxy)methyl]-2-hydroxy-3-methylpyrrolidine-1-carboxylate (5.2 g). This crude material was used in the next step.

Step 6D: tert-butyl (5S)-5-[(benzoyloxy)methyl]-2-hydroxy-3-methylpyrrolidine-1-carboxylate (5.03 g, 14.997 mmol, 1 equiv.) and p-toluenesulfonic acid monohydrate (0.029 g, 0.15 mmol, 0.01 equiv.) were heated in toluene (50.3 mL, 0.298 M, 10 Vols) for 2 hours at 70° C. The reaction was cooled, washed with saturated aqueous NaHCO$_3$, dried and evaporated. The crude material was purified by chromatography over silica gel (10% EtOAc/hexane) to afford 3.5 g of olefin 23.

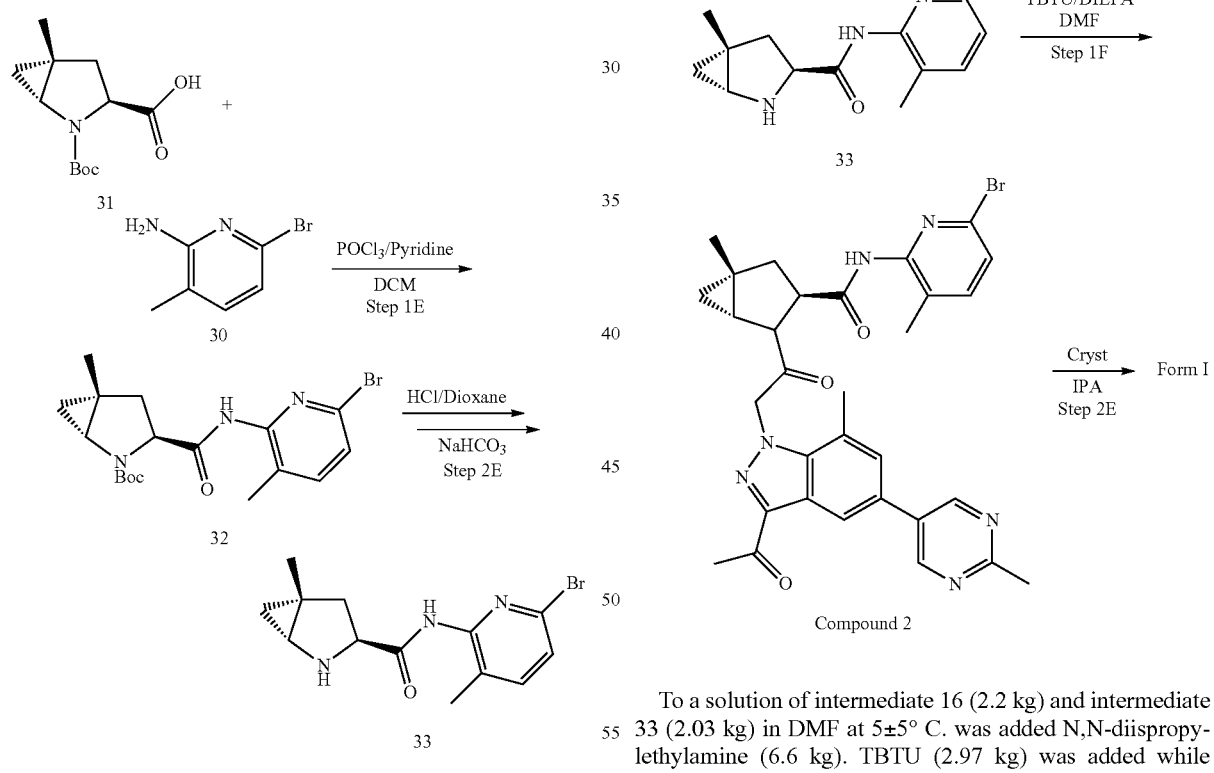

Step 1E: Intermediate 31 (10 kg) and intermediate 30 (7.4 kg) were dissolved in DCM/pyridine and cooled to 0±5° C. Phosphorousoxy chloride (7 kg) was added to the mixture while maintaining the reaction temperature. After the reaction was complete, water was added carefully and the reaction was allowed to warm to room temperature. The aqueous layer was extracted with DCM and the combined DCM layers were washed with dilute HCl and water, dried over anhydrous sodium sulfate and evaporated to dryness. Heptane was added and evaporated and the residue triturated with 5% ethylacetate/heptane. The solid was filtered and dried to afford intermediate 32 (Yield 11.4 kg).

Step 2E: Intermediate 32 (5 kg) was added to 4M HCl/dioxane (21 kg) and the reaction was stirred at room temperature. After completion, the reaction was diluted with DCM and carefully washed with aqueous NaHCO$_3$. The DCM layer was washed with water and evaporated to dryness. The product was crystallized from DCM/heptane to afford intermediate 33 (Yield 3.8 kg).

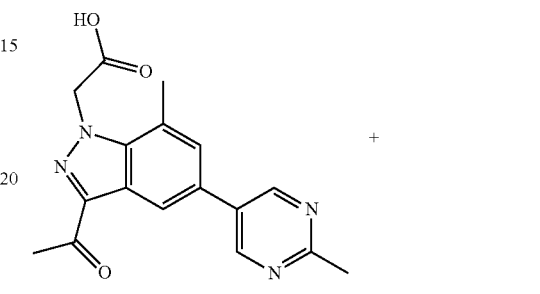

To a solution of intermediate 16 (2.2 kg) and intermediate 33 (2.03 kg) in DMF at 5±5° C. was added N,N-diisopropylethylamine (6.6 kg). TBTU (2.97 kg) was added while maintaining the temperature of the reaction at 5±5° C. The reaction was warmed to room temperature and stirred for 4-8 hours. The reaction was diluted with water and the resulting solid formed was collected by centrifugation. The solid was washed with water two times and then dissolved in DCM and treated with siliabondthiol resin and activated charcoal to remove Pd based impurities. The resin and charcoal were removed by filtration and washed with MeOH/DCM. The filtrates were evaporated to dryness and the reside purified by chromatography over silica gel using methanol/DCM. The pure fractions were combined and evaporated to dryness. The residue was crystallized from IPA/heptane to afford Compounds 2 Form 1 (Yield, 1.84 kg).

Example 7

Polymorph Experiments of Compound 2

A series of experiments were conducted to investigate the polymorphic landscape of Compound 2 (Table 7). A wide variety of solvents/solvent systems were utilized.

Attempts at melting the material were unsuccessful. Compound 2 discolored prior to becoming a uniform liquid phase indicating that decomposition may have occurred.

A number of crash precipitation (CP) experiments were carried out. When water or heptane was used as anti-solvents, solids tended to be generated from solution. A number of these experiments generated extremely small quantities of solids that were not characterized. Only Form 1 and disordered materials were generated from the experiments. When a solvent other than water or heptane were utilized as anti-solvents, the vast majority of the experiments generated no solids. A few others generated material, but the quantity was too small to characterize.

Ambient temperature (RT) solvent/anti-solvent precipitation experiments were generally unsuccessful. A set of experiments utilizing tetrahydrofuran as the solvent and either water or heptane as the anti-solvent generated enough solids for characterization. When hexafluoroisopropyl alcohol (HFIPA) was used as a solvent, the solution discolored (yellow/brown/red). Either Form 1 or disordered Compound 2 was generated from these experiments. The vast majority of the other solvent combinations attempted produced solids free solutions. However, sonicating these solutions generated a number of solid materials. All the recovered solids from these sonication experiments were Compound 2 Form 1.

Evaporative and slow cool experiments that generated materials were almost always Compound 2 Form 1. The only exception was two evaporative experiments (from tetrahydrofuran and dichloromethane) that generated glasses. Upon characterization, these proved to be highly disordered.

The disordered Compound 2 was subjected to water activity slurries in methanol at ambient temperature and Form 1 resulted.

TABLE 7

Polymorph Studies of Compound 2

| Solvent | Conditions | Observation | XRPD Result |
|---|---|---|---|
| — | Melt | Solids persisted in melt, sample turned brown prior to completely melting. | — |
| Acetone | FE | Rosettes of fine needles | Form 1 |
|  | SC | Fine needles in solution | Form 1 |
| Acetone/ACN | CP | Initially, a clear solution resulted. Sample capped and left at RT. Solids free solution resulted. | — |
|  | FE | Thin film of solids - no B/E | — |
| Acetone/EtOAc | CP | Initially, a clear solution resulted. Sample capped and left at RT. A few, fine particles (B/E) in solution - s.s. | — |
|  | FE | Rosettes of needles - s.s. | — |
| Acetone/Heptane | CP | Initially, a slightly hazy solution resulted. Sample capped and left at RT. Fine needles in solution - s.s. | — |
|  | FE | Needles - s.s. | — |
| Acetone/H$_2$O | CP | Initially, a clear solution resulted. Sample capped and left at RT. Needles in solution. | Form 1 |
|  | FE | White, opaque solids; no B/E - s.s. | — |
| ACN | FE | Rosettes of fine needles + a few blades | Form 1 |
|  |  | Rosettes of fine needles - s.s. | — |
| ACN/Toluene | CP | Initially, a clear solution resulted. No solids generated. | — |
|  | VR | Thin, opaque film containing a few, fine particles (B/E) s.s. | — |
| ACN/H$_2$O | CP | Initially, a slightly hazy solution resulted. Needles in cloudy solution generated - s.s. | — |
|  | VR | Needles - s.s. | — |
| CH$_2$Cl$_2$ | FE | Light yellow, opaque glass | Disordered |
|  | ET FE | Light brown solids | Form 1 |
|  | SE | Light yellow, opaque glass | — |
| CH$_2$Cl$_2$/ACN | RT ppt | Light yellow, clear solution immediately present. Sample sealed and left at RT. No solids generated. | — |
|  | Sonication | Needles | Form 1 |
| CH$_2$Cl$_2$/EtOAc | RT ppt | Light yellow, clear solution immediately present. Sample sealed and left at RT. No solids generated. | — |
|  | Sonication | Needles | Form 1 |
| CH$_2$Cl$_2$/Heptane | RT ppt | White ppt immediately formed - s.s. | — |
|  | CP | Sample immediately turned cloudy when contacted with anti-solvent. | Disordered |
|  | CP/Roto-vap | Sample immediately turned cloudy when contacted with anti-solvent. | Disordered |
| CH$_2$Cl$_2$/IPA | RT ppt | Light yellow, clear solution immediately present. Sample sealed and left at RT. No solids generated. | — |
|  | Sonication | Fine needles in solution | Form 1 |
| EtOAc | FE | Needles + orange masses (unknown morphology, no B/E) | Form 1 |
| HFIPA | FE |  | — |
| HFIPA/ACN | Ppt | No solids in light golden solution | — |
|  | VR | Yellow/Brown glass | — |

TABLE 7-continued

Polymorph Studies of Compound 2

| Solvent | Conditions | Observation | XRPD Result |
|---|---|---|---|
| HFIPA/CH$_2$Cl$_2$ | Ppt | Needles in solution - s.s. | — |
| | VR | Light red glass | Disordered |
| HFIPA/EtOAc | Ppt | No solids in light golden solution | — |
| | VR | Yellow/Brown glass | Form 1 |
| HFIPA/H$_2$O | Ppt | Cloudy solution containing oil | — |
| IPA | FE | Needles | Form 1 |
| | | Thin film containing a few, fine needles - s.s. | — |
| | SC | Opaque solids, no B/E in solution | — |
| | SVD | — | Form 1 |
| IPA/Heptane | CP | Initially, a solids free solution resulted. Sample sealed and left at RT. No solids generated. | — |
| | VR | Thin, opaque film - s.s. | — |
| IPA/Toluene | CP | Initially, a clear solution resulted. No solids generated. | — |
| | VR | Thin, opaque film. | — |
| IPA/H$_2$O | CP | Initially, a clear solution resulted. Hazy solution containing fine, suspended particles (no B/E) generated - s.s. | — |
| | VR | Fine particles (some B/E); unknown morphology - s.s. | — |
| | CP | Initially, a solids free solution resulted. Sample sealed and left at RT. No solids generated. | — |
| | VR | Needles - s.s. | — |
| MeOH | FE | Small needles | Form 1 |
| | SC | Fine needles in solution | — |
| MeOH/ACN | CP | Initially, a clear solution resulted. Sample capped and left at RT. No solids generated over time. | — |
| | FE | Needles - s.s. | — |
| MeOH/EtOAc | CP | Initially, a clear solution resulted. Sample capped and left at RT. No solids generated over time. | — |
| | FE | Thin, yellow film, no B/E - s.s. | — |
| MeOH/Toluene | CP | Initially, a clear solution resulted. Sample capped and left at RT. No solids generated over time. | — |
| | FE | White film; no B/E - s.s. | — |
| MeOH/H$_2$O | CP | Initially, a clear solution resulted. Sample capped and left at RT. Needles generated - s.s. | — |
| | FE | White, opaque solids; no B/E - s.s. | — |
| | CP | Initially, a hazy solution resulted. Sample sealed and left at RT. Needles developed in solution - s.s. | — |
| | VR | Needles | Form 1 |
| MeOH/H$_2$O [45/55] | RT Slurry | — | Form 1 |
| MeOH/H$_2$O [60/40] | RT Slurr | — | — |
| MeOH7H$_2$O [80/20] | RT Slurry | — | — |
| MeOH/H$_2$O [90/10] | RT Slurry | — | — |
| MEK | FE | Needles | Form 1 |
| | SC | A few needles in solution - s.s. | — |
| | FE | Needles | Form 1 - some peak shifting detected |
| MEK/Heptane | CP | Initially, a clear solution resulted. Needles - s.s, resulted. | — |
| | VR | Small, fine needles - s.s. | — |
| THF | FE | Light yellow, opaque glass | Disordered |
| | SE | Light yellow, opaque glass | — |
| | SVD | — | Form 1 |
| THF/EtOAc | RT ppt | Light yellow, clear solution immediately present. Sample sealed and left at RT. No solids generated. | — |
| | Sonication | Needles | Form 1 |
| THF/Heptane | RT ppt | White ppt immediately formed in solution. | Disordered |
| THF/IPA | RT ppt | Light yellow, clear solution immediately present. Sample sealed and left at RT. No solids generated. | — |
| | Sonication | Fine needles + opaque solids (no B/E) in solution | Form 1 |
| THF/H$_2$O | RT ppt | White solution immediately formed - oil in solution. Sample capped and left at RT. Some fine solids generated in solution (no B/E). Needles developed with time. | Form 1 |

TABLE 7-continued

Polymorph Studies of Compound 2

| Solvent | Conditions | Observation | XRPD Result |
|---|---|---|---|
| Toluene | FE | Small fine solids, unknown morphology; no B/E | Form 1 |
|  | SVD | — | Form 1 |
| H$_2$O | SC | No solids in solution | — |
|  | FE | Film, s.s. | — |

FE: Fast evaporation
ET: Elevated temperature fast evaporation
SE: Slow evaporation
VR: Volume reduction
SC: Slow cool
RT ppt: Ambient temperature precipitation
CP: Crash precipitation
SVD: Solid-vapor diffusion
Roto-vap: Rotary Evaporation The procedures for the conditions in Table 7 are discussed below.

Fast Evaporation (FE): Solutions of Compound 2 and the solvent/solvent system of interest were prepared and filtered. The solids-free solutions were left open to ambient conditions until all the solvent had evaporated and the generated solids could be collected.

Elevated Temperature (ET) Fast Evaporation: Solutions of Compound 2 and the solvent/solvent system of interest were prepared and filtered at elevated temperature. The solids-free solutions were left open to ambient conditions at temperature until all the solvent had evaporated and the generated solids could be collected.

Slow Evaporation (SE): Solutions of Compound 2 and the solvent/solvent system of interest were prepared and filtered. The samples were covered with aluminum foil which had been perforated. The solids-free solutions were left open to ambient conditions until all the solvent had evaporated and the generated solids could be collected.

Volume Reduction (VR): Saturated solutions of Compound 2 and a solvent/solvent system of interest were prepared. The solutions were filtered and left open to ambient conditions. The volume reduction was halted prior to the sample drying completely, the samples capped and left at ambient temperature.

Slow Cool (SC): Saturated solutions of Compound 2 and the solvent/solvent system of interest were prepared at elevated temperature. After a period of time at temperature to ensure that the solutions were saturated, the samples were filtered into warm receiving vials. The heating source was shut off and the samples were left to slowly cool towards ambient temperature. If no solids were generated, the samples were placed at sub-ambient temperatures.

Ambient Temperature (RI) Precipitation (Ppt): A saturated solution of Compound 2 and a solvent of interest was prepared at ambient temperature. This solution was filtered directly into a vessel containing an anti-solvent at ambient temperature. The samples were monitored for immediate generation of solids.

Crash Precipitation (CP): A saturated solution of Compound 2 and a solvent of interest was prepared at elevated temperature. This solution was filtered directly into a vessel containing an anti-solvent at ambient temperature. The samples were monitored for immediate generation of solids.

Solid-Vapor Diffusion (SVD): Solid samples of Compound 2 were exposed to organic vapors in a sealed chamber. After a period of time, the Compound 2 solids were removed and characterized.

Rotary Evaporation (Roto-vap): Filtered solutions containing Compound 2 were placed onto a Büchi Rotavapor R-114. The samples were kept at ambient temperature as the volumes were reduced under vacuum. Solids collected after all the solvent had been removed from the samples.

An enabling form study was carried out at ambient, elevated (approximately 60° C.) and sub-ambient (2-8° C.) temperature (Table 8). All generated materials were Compound 2 Form 1.

TABLE 8

Enabling Form Study for Morphic Forms of Compound 2

| Solvent | Conditions | Observation | XRPD Result |
|---|---|---|---|
| CH$_2$Cl$_2$ | RT Slurry | — | Form 1 |
|  | ~2-8° C. Slurry | — | Form 1 |
| EtOH | RT Slurry | — | Form 1 |
| HFIPA | RT Slurry | Solids free solution generated | — |
| IPA | ~2-8° C. Slurry | — | Form 1 |
|  | RT Slurry | — | Form 1 |
|  | ~60° C. Slurry | — | Form 1 |
| MTBE | RT Slurry | — | Form 1 |
| THF | ~2-8° C. Slurry | — | Form 1 |
|  | ~60° C. Slurry | — | Form 1 |
| Toluene | ~2-8° C. Slurry | — | Form 1 |
|  | RT Slurry | — | Form 1 |

Example 8

Characterization of Compound 2 Form I Polymorph

Figure 14:
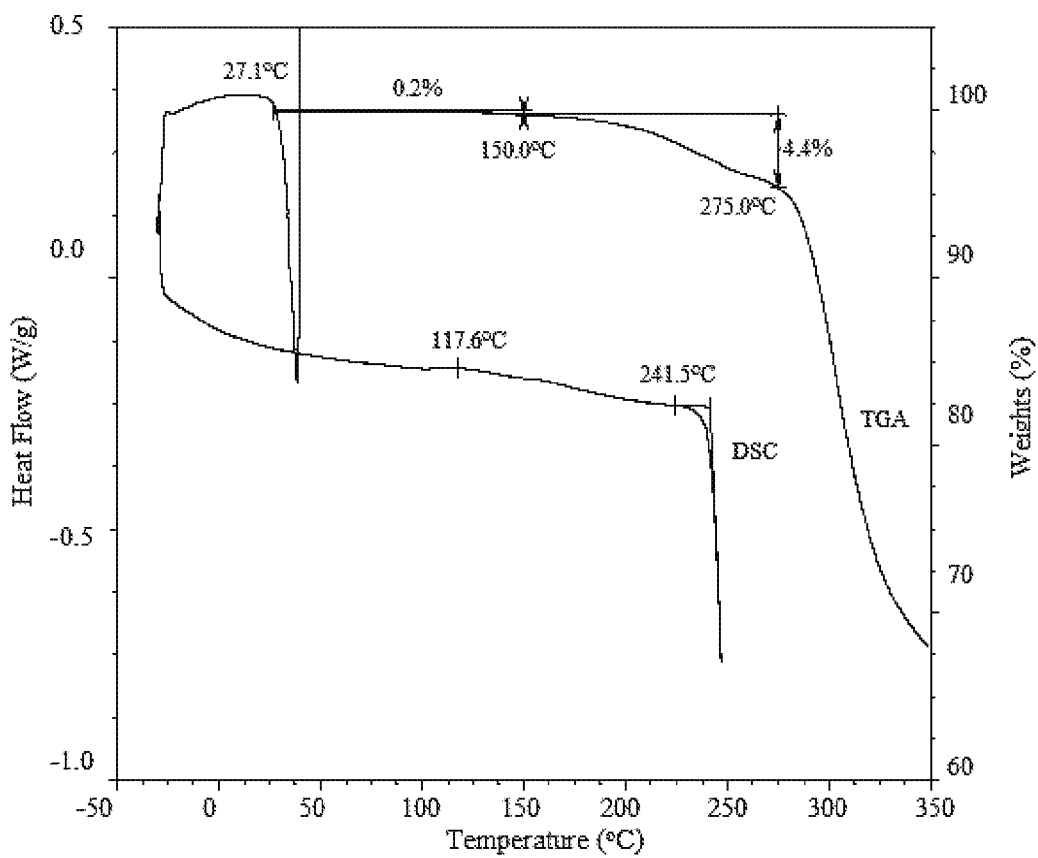
FIG. 14 is a DSC and a TGA graph of Compound 2 Form I as discussed in Example 8. The x-axis is temperature measured in ° C., the left y-axis is heat flow measured in (W/g), and the right y-axis is weight measured in percent.
Figure 15A:
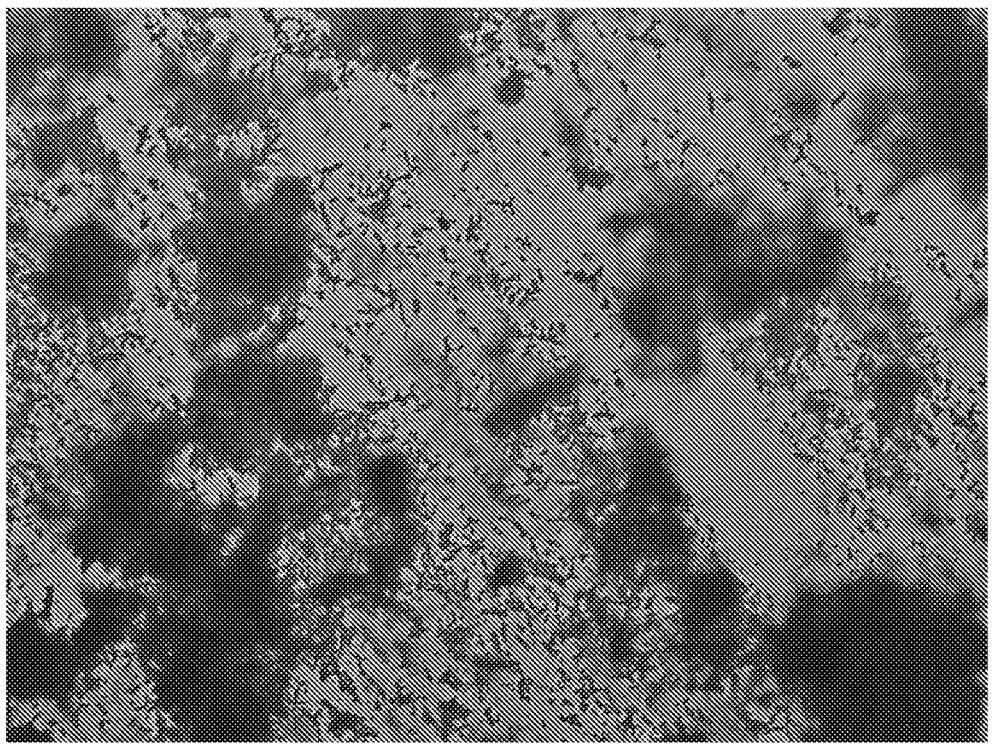
FIG. 15A is an image collected from the hot stage microscopy analysis of Compound 2 Form I as discussed in Example 8. The image was taken as heating was initiated (26° C.).
Figure 15B:
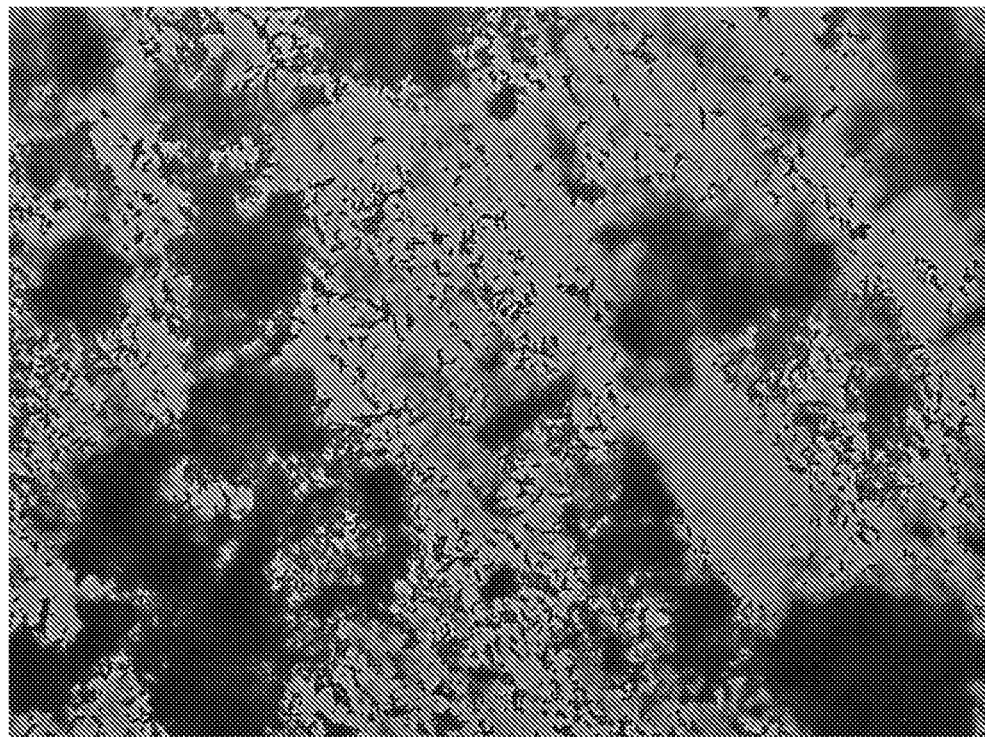
FIG. 15B is an image collected from the hot stage microscopy analysis of Compound 2 Form I as discussed in Example 8. The image was taken at 116.4° C. A slight increase in birefringent character was detected.
Figure 15C:
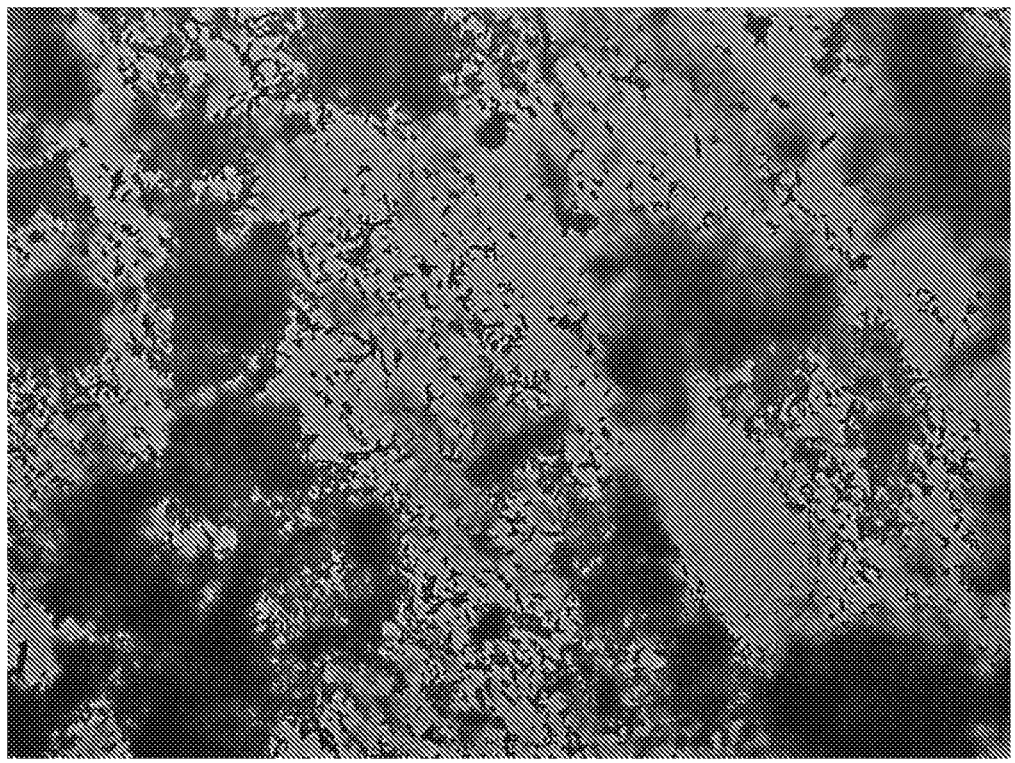
FIG. 15C is an image collected from the hot stage microscopy analysis of Compound 2 Form I as discussed in Example 8. The image was taken at 188.1° C. The birefringent character of the sample continues to change at this temperature and fogging of the coverslip was observed.
Figure 15D:
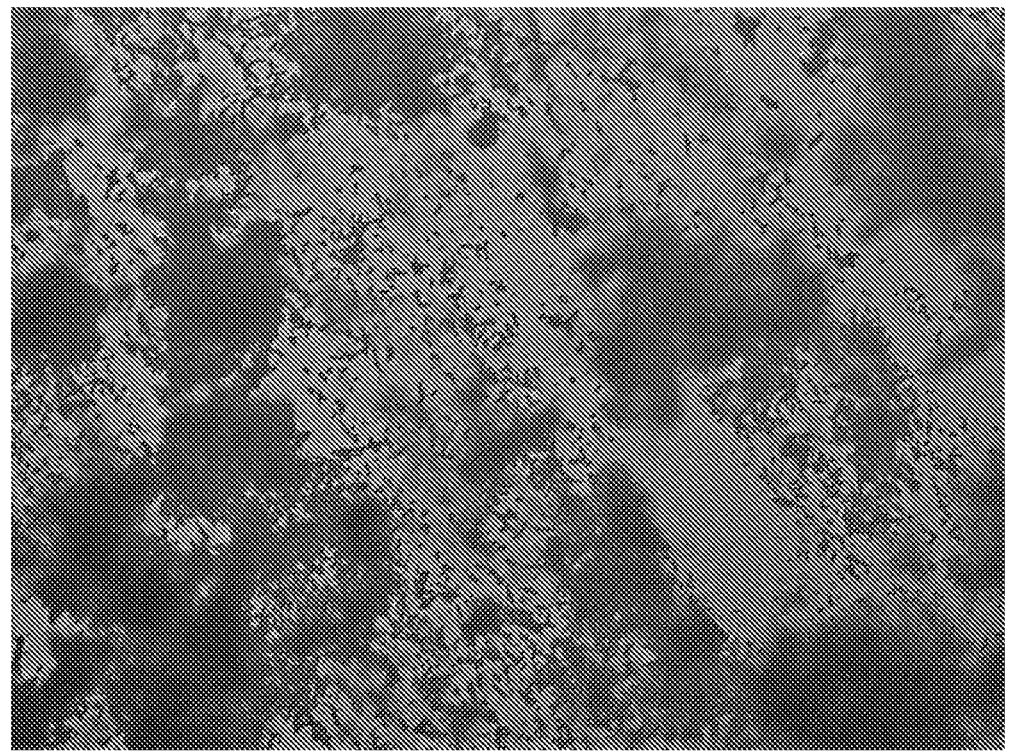
FIG. 15D is an image collected from the hot stage microscopy analysis of Compound 2 Form I as discussed in Example 8. The image was taken at 191.6° C. The fogging of the coverslip was continued to be observed.
Figure 15E:
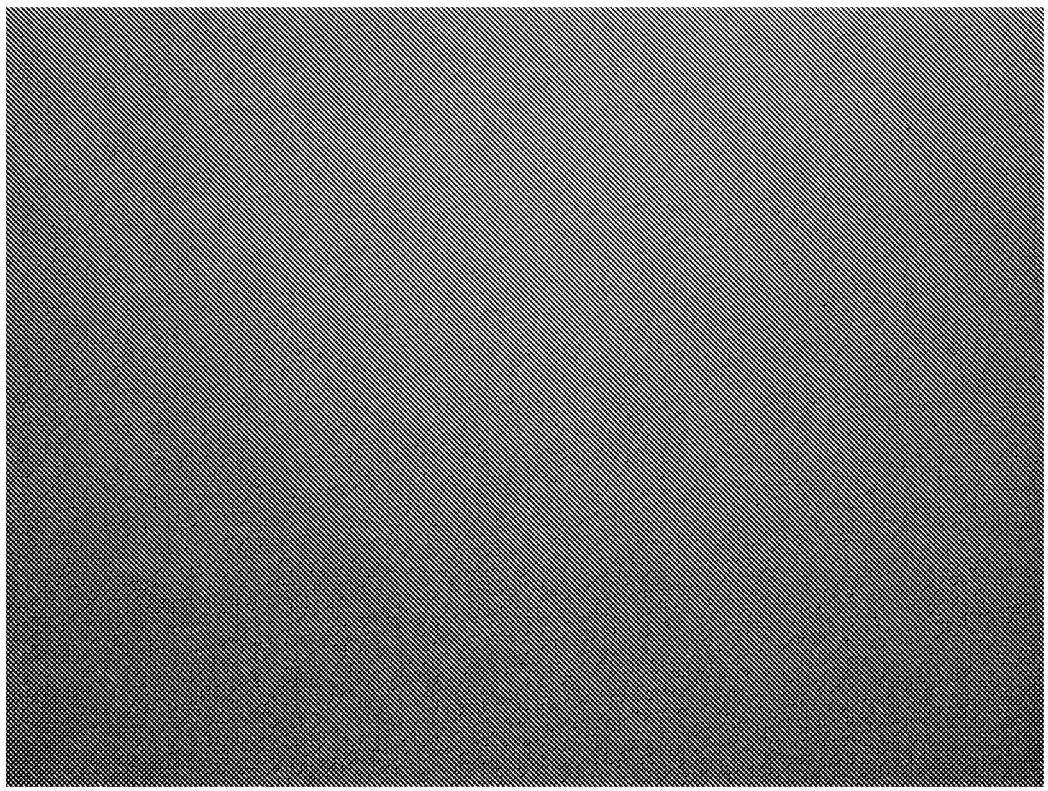
FIG. 15E is an image collected from the hot stage microscopy analysis of Compound 2 Form I as discussed in Example 8. The image was taken between 191.6° C. and 236.4° C.
Figure 15F:
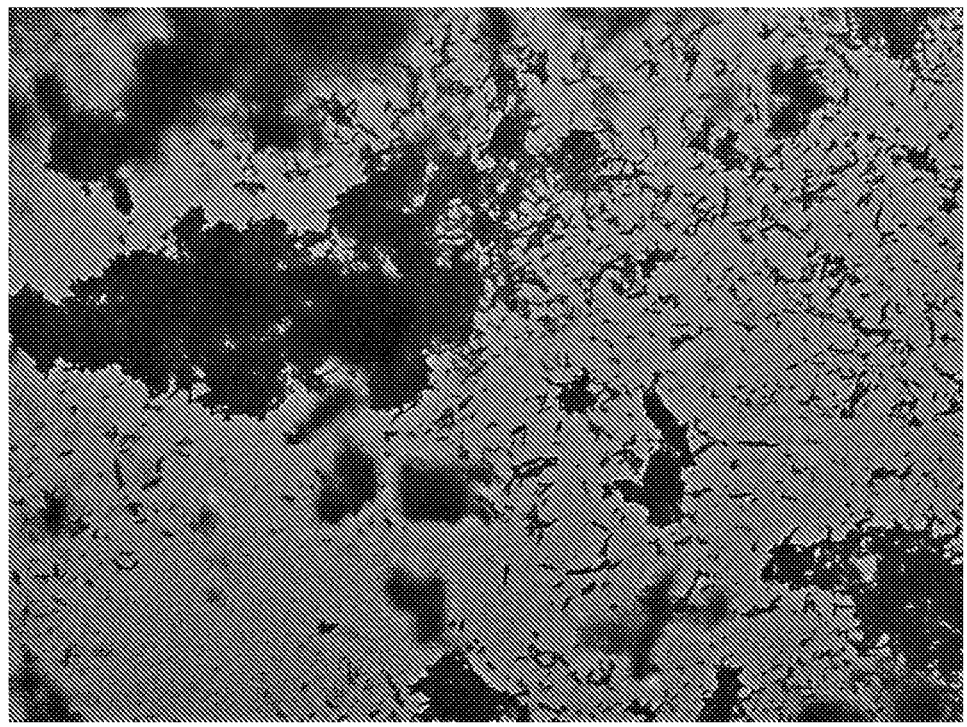
FIG. 15F is an image collected from the hot stage microscopy analysis of Compound 2 Form I as discussed in Example 8. The image was taken at 236.4° C.
Figure 15G:
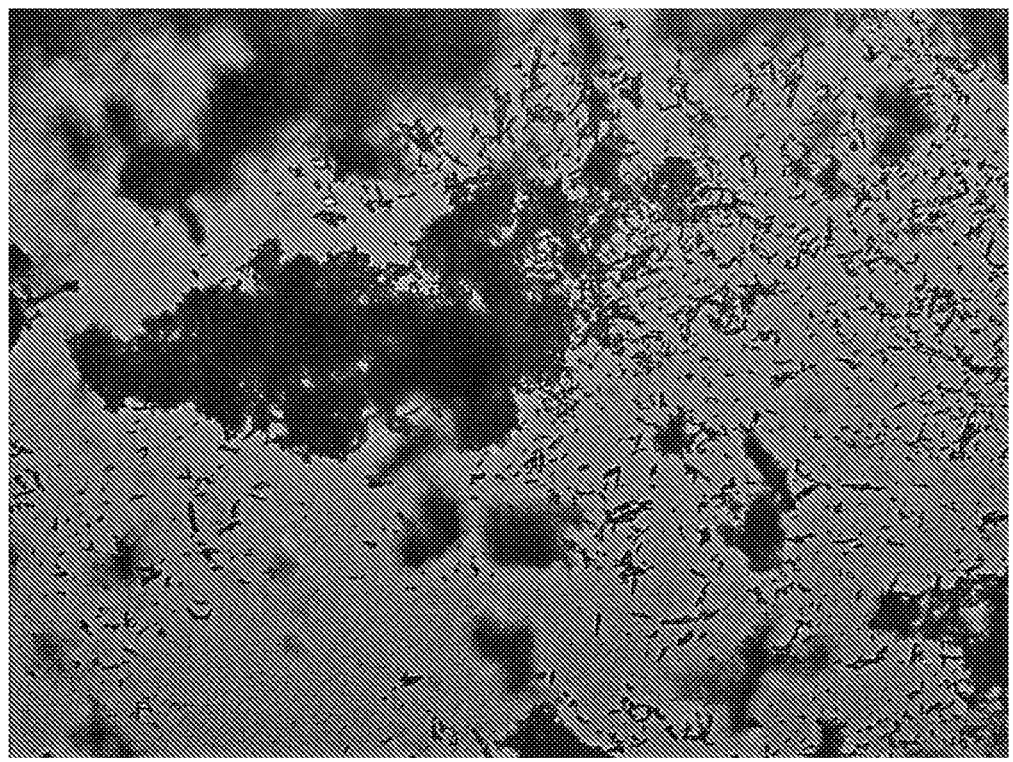
FIG. 15G is an image collected from the hot stage microscopy analysis of Compound 2 Form I as discussed in Example 8. The image was taken at 250.9° C. and the onset of melting was observed.
Figure 15H:
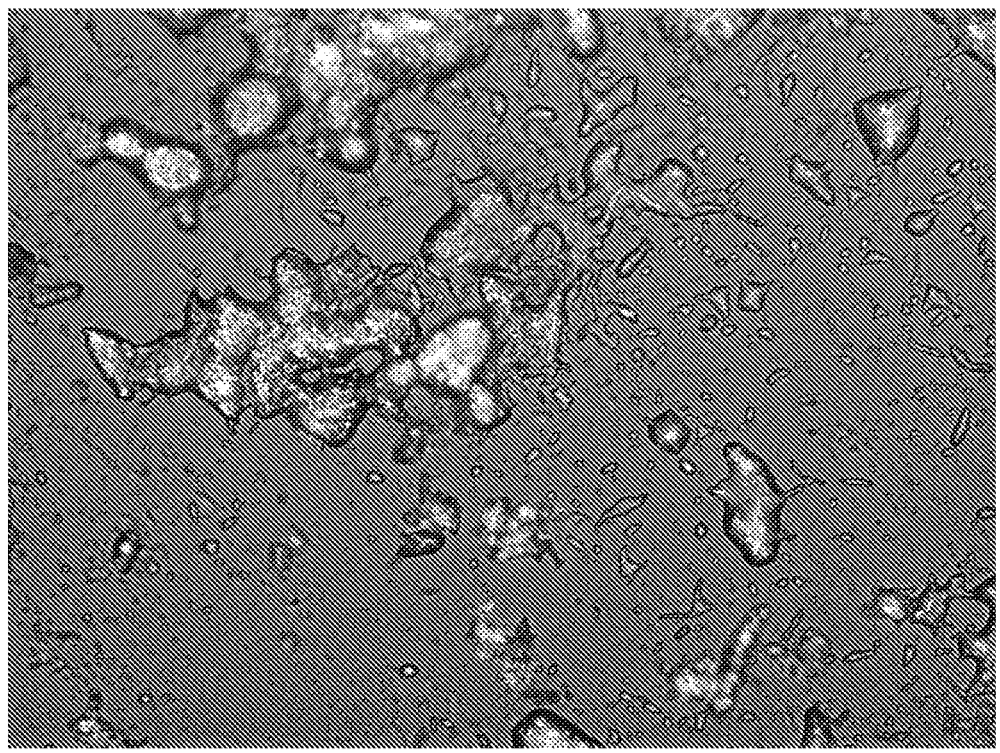
FIG. 15H is an image collected from the hot stage microscopy analysis of Compound 2 Form I as discussed in Example 8. The image was taken at 260° C. and melting was observed.
Figure 15I:
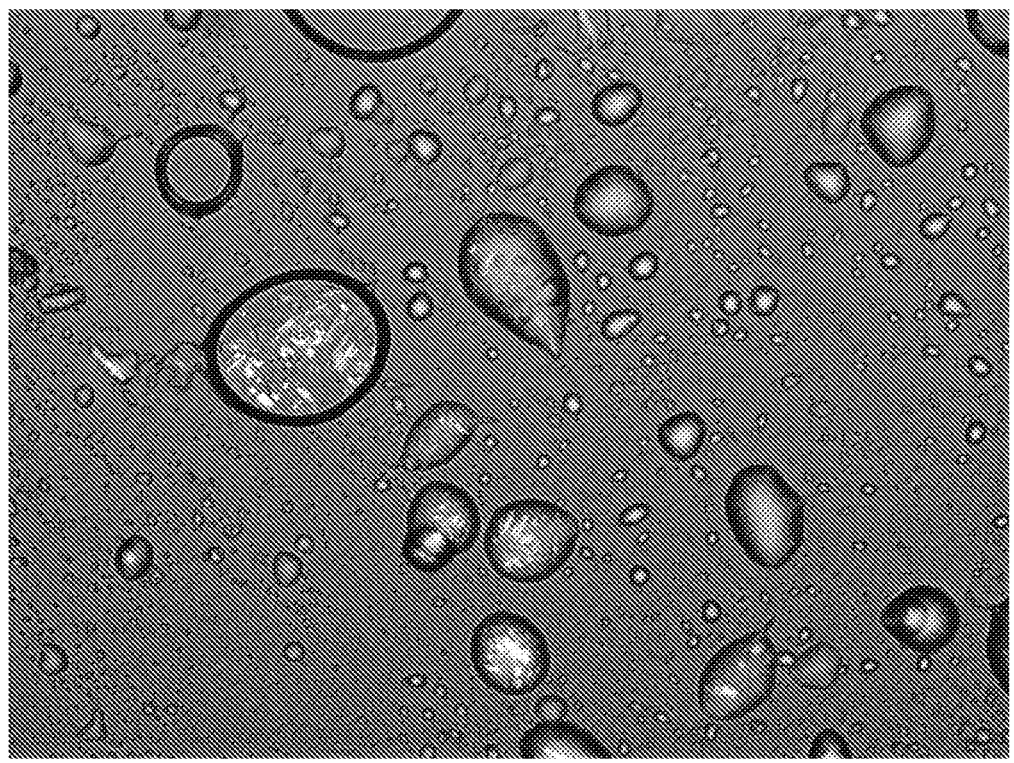
FIG. 15I is an image collected from the hot stage microscopy analysis of Compound 2 Form I as discussed in Example 8. The image was taken at 262.9° C. and melting was observed.
Figure 15J:
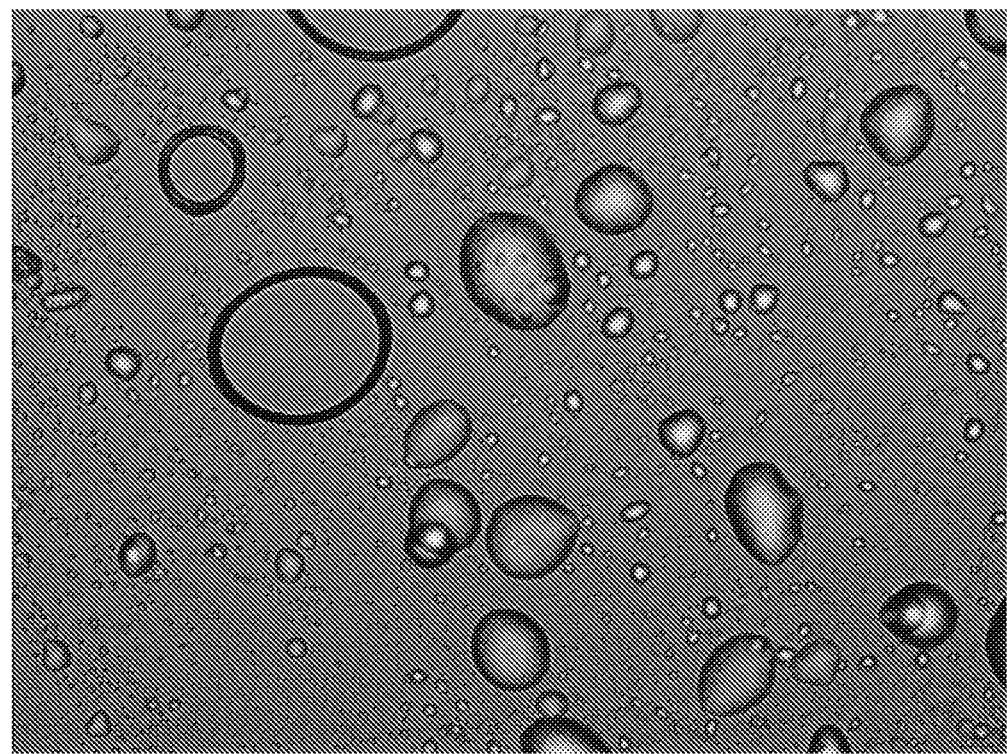
FIG. 15J is an image collected from the hot stage microscopy analysis of Compound 2 Form I as discussed in Example 8. The image was taken at 263.4° C. at which point the melting was complete. The heat was turned off.
Figure 15K:
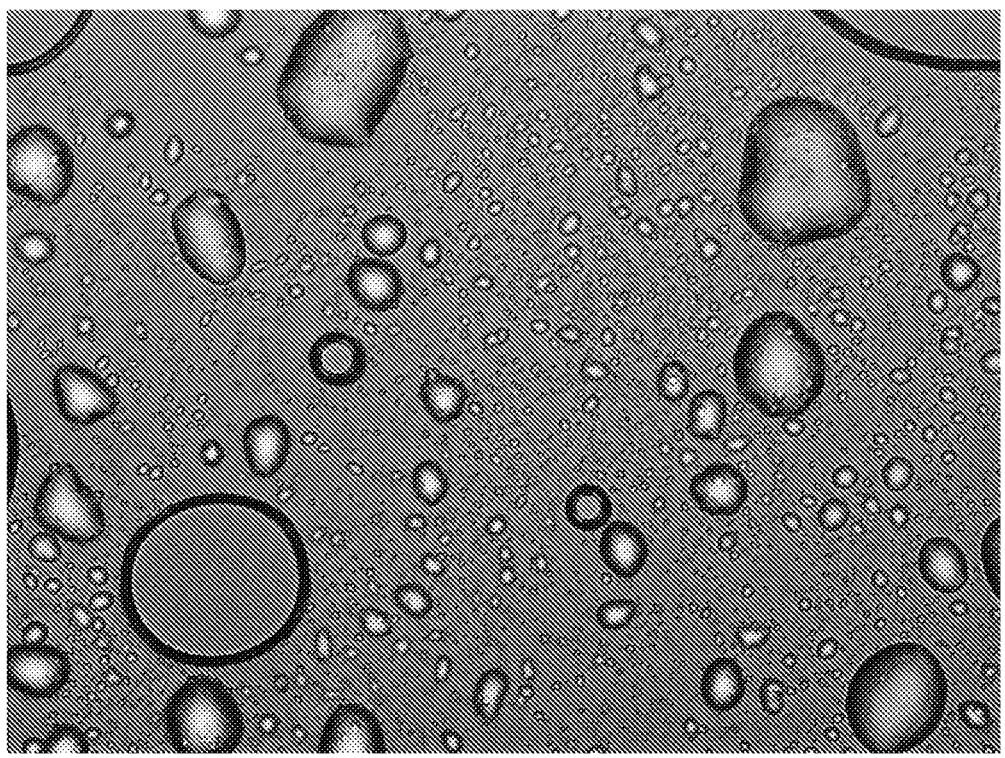
FIG. 15K is an image collected from the hot stage microscopy analysis of Compound 2 Form I as discussed in Example 8. The image was taken at 30° C. and no signs of recrystallization were observed.
Figure 15L:
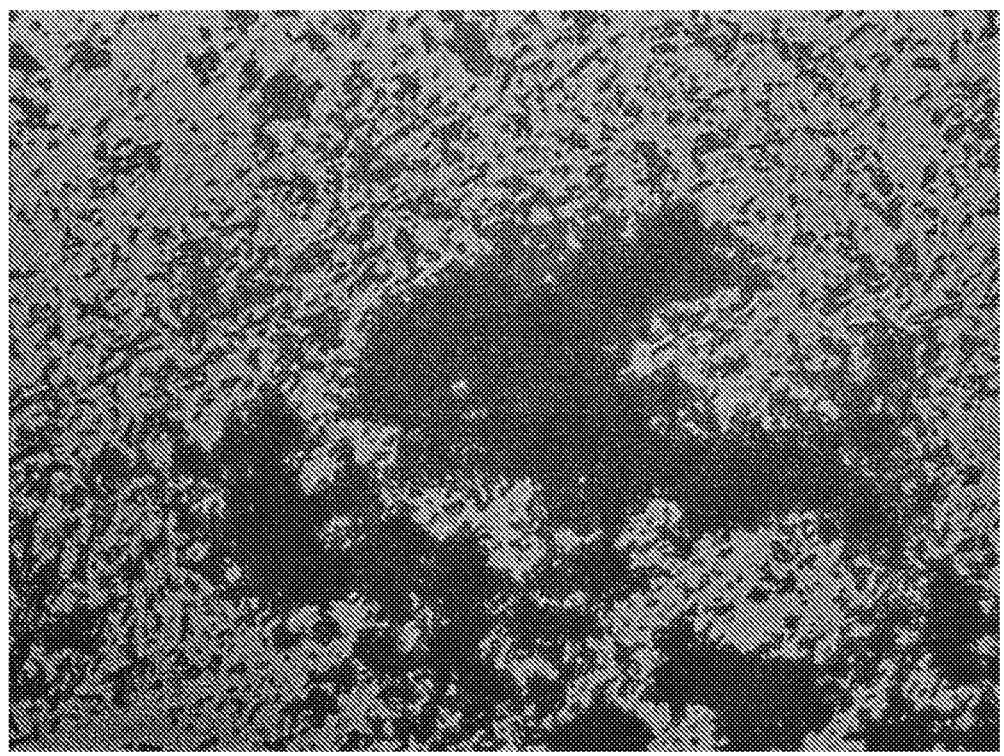
FIG. 15L is an image collected from the hot stage microscopy analysis of Compound 2 Form I as discussed in Example 8. The image was taken at 25.7° C. at which point the sample was subjected to reheating.
Figure 15M:
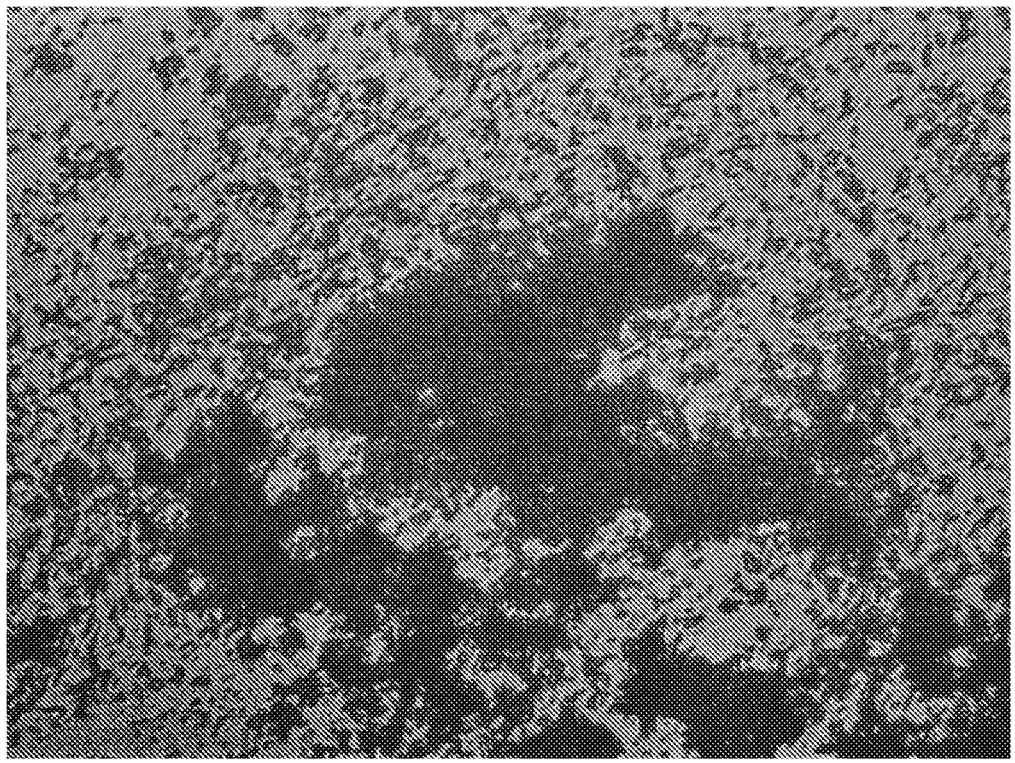
FIG. 15M is an image collected from the hot stage microscopy analysis of Compound 2 Form I as discussed in Example 8. The image was taken at 99.3° C. at which point no change to the sample was observed.
Figure 15N:
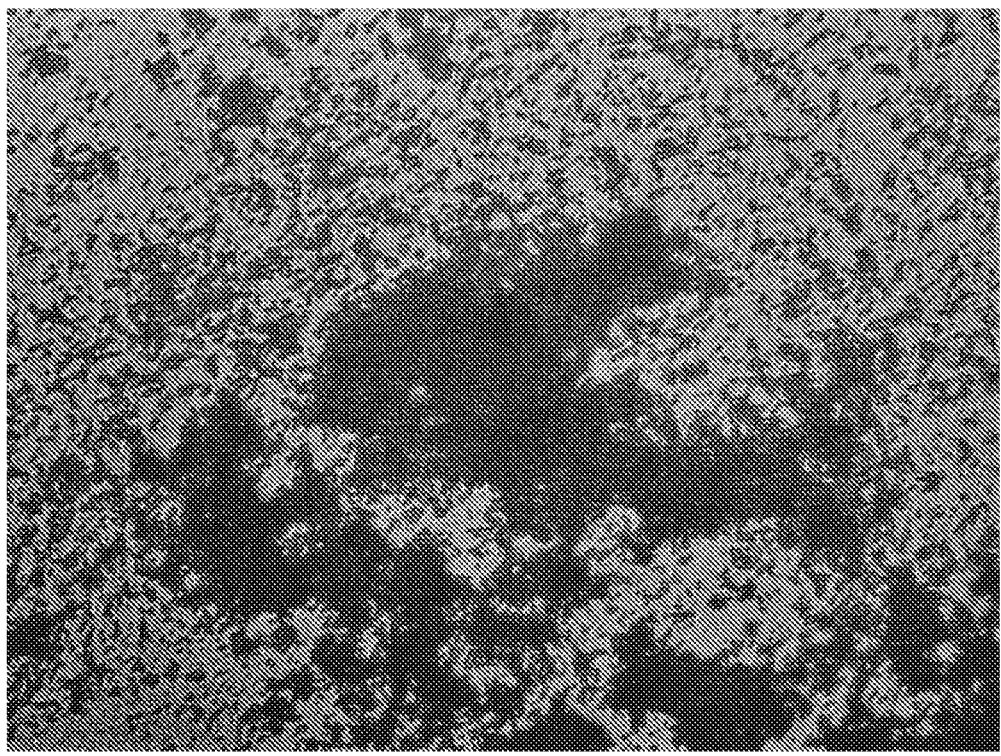
FIG. 15N is an image collected from the hot stage microscopy analysis of Compound 2 Form I as discussed in Example 8. The image was taken at 123.4° C. at which point no change to the sample was observed.
Figure 16:
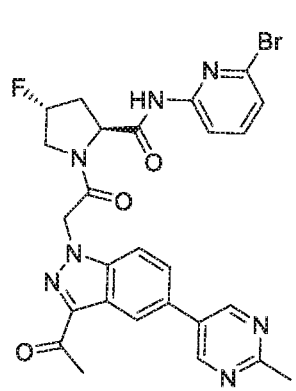
FIG. 16 is Factor D inhibitors Compound 1 and Compound 2.
Figure 16:
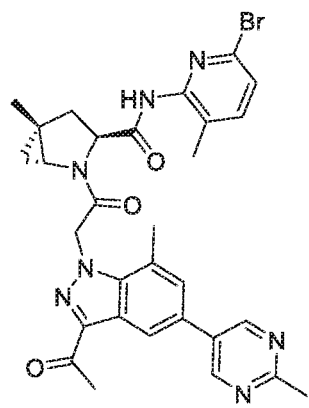

The characteristics of Compound 2 Form I Polymorph are shown in Table 9. The XRPD pattern indicated that the material was crystalline. The pattern was successfully indexed (FIG. 13) indicating that the material was of a single solid phase. Thermal analysis of the material (FIG. 14) indicated a wide, weak exothermic feature at approximately 118° C. preceding a sharp endotherm (with an onset at approximately 242° C.). While a very minor weight loss was detected up to 150° C., the endothermic transition coincided with a more substantial weight loss. Decomposition of the material was apparent soon after the endothermic event. Hot stage microscopy data was collected (FIG. 15A-FIG. 15N). A slight shift in the birefringent character of the sample was detected at approximately 116° C., while fogging of the coverslip was detected at approximately 190° C. The sample melted between 251 and 263° C. Discoloration of the sample was noted when the sample was cooled to ambient temperature indicating that the material may have undergone a decomposition step during the melt.

TABLE 9

Summary of Characteristics of Compound 2 Form I

| Material | Analytical Technique | Results |
|---|---|---|
| Compound 2 Form I | XRPD | Crystalline Form 1 |
| | DSC | Wd, wk exo centered at ~118° C. Sharp endo, onset ~242° C. |
| | TG | 0.2% wt loss to 150° C. |
| | HS | Melt: 251-263° C., discoloration of sample noted when melt was complete |

FIG. 13 is the indexed XRPD pattern. Table 10 provides the data measurement of Compound 2 Form I. Table 11 provides the observed peaks of the XRPD and the prominent peaks are labeled with an asterisk.

TABLE 10

Data Measurement of XRPD Pattern of Compound 2 Form I

| Bravais Type | Primitive Monoclinic |
|---|---|
| a [Å] | 10.739 |
| b [Å] | 6.600 |
| c [Å] | 19.551 |
| α [deg] | 90 |
| β [deg] | 92.91 |
| γ [deg] | 90 |
| Volume [Å$^3$/cell] | 1,384.0 |
| Chiral contents? | Chiral |
| Extinction Symbol | P 1 2$_1$ 1 |
| Space Group(s) | P2$_1$ (4) |

TABLE 11

Peaks of XRPD Pattern for Compound 2 Form I

| °2θ | d space (Å) | Intensity (%) |
|---|---|---|
| 4.51 ± 0.20* | 19.578 ± 0.868 | 58 |
| 8.23 ± 0.20* | 10.734 ± 0.260 | 39 |
| 9.19 ± 0.20* | 9.619 ± 0.209 | 26 |
| 9.59 ± 0.20* | 9.211 ± 0.192 | 47 |
| 11.93 ± 0.20* | 7.413 ± 0.124 | 25 |
| 12.55 ± 0.20 | 7.048 ± 0.112 | 9 |
| 13.59 ± 0.20 | 6.511 ± 0.095 | 10 |
| 14.15 ± 0.20 | 6.254 ± 0.088 | 9 |
| 15.75 ± 0.20* | 5.623 ± 0.071 | 68 |
| 16.22 ± 0.20* | 5.460 ± 0.067 | 88 |
| 16.51 ± 0.20 | 5.366 ± 0.065 | 19 |
| 16.91 ± 0.20 | 5.240 ± 0.062 | 14 |
| 17.35 ± 0.20* | 5.106 ± 0.058 | 66 |
| 17.98 ± 0.20* | 4.928 ± 0.054 | 29 |
| 18.43 ± 0.20* | 4.811 ± 0.052 | 61 |
| 19.14 ± 0.20 | 4.634 ± 0.048 | 26 |
| 19.58 ± 0.20 | 4.530 ± 0.046 | 7 |
| 20.59 ± 0.20 | 4.311 ± 0.041 | 10 |
| 20.91 ± 0.20 | 4.244 ± 0.040 | 21 |
| 21.14 ± 0.20* | 4.199 ± 0.039 | 54 |
| 21.64 ± 0.20 | 4.103 ± 0.037 | 19 |
| 21.99 ± 0.20* | 4.038 ± 0.036 | 50 |
| 22.64 ± 0.20* | 3.925 ± 0.034 | 100 |
| 22.88 ± 0.20 | 3.884 ± 0.033 | 30 |
| 23.55 ± 0.20 | 3.775 ± 0.032 | 32 |
| 23.81 ± 0.20* | 3.734 ± 0.031 | 40 |
| 24.01 ± 0.20 | 3.703 ± 0.030 | 20 |
| 24.45 ± 0.20 | 3.637 ± 0.029 | 27 |
| 24.92 ± 0.20 | 3.570 ± 0.028 | 13 |
| 25.27 ± 0.20 | 3.522 ± 0.027 | 8 |
| 25.54 ± 0.20 | 3.485 ± 0.027 | 10 |
| 25.84 ± 0.20 | 3.445 ± 0.026 | 23 |
| 26.09 ± 0.20 | 3.413 ± 0.026 | 16 |
| 26.50 ± 0.20 | 3.360 ± 0.025 | 27 |
| 26.99 ± 0.20 | 3.301 ± 0.024 | 8 |
| 27.43 ± 0.20* | 3.249 ± 0.023 | 44 |
| 27.84 ± 0.20 | 3.202 ± 0.023 | 18 |
| 28.27 ± 0.20 | 3.154 ± 0.022 | 25 |
| 28.55 ± 0.20 | 3.124 ± 0.021 | 21 |
| 28.71 ± 0.20 | 3.107 ± 0.021 | 25 |
| 29.08 ± 0.20 | 3.069 ± 0.021 | 23 |

*Prominent peaks

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report.

DSC (Differential Scanning calorimetry) was performed using a TA Instruments Q2000 differential scanning calorimeter. Temperature calibration was performed using NIST-traceable indium metal. The sample was placed into an aluminum DSC pan, covered with a lid, and the weight was accurately recorded. A weighed aluminum pan configured as the sample pan was placed on the reference side of the cell. The data acquisition parameters and pan configuration for each thermogram are displayed in the image in the Data section of this report. The method code on the thermogram is an abbreviation for the start and end temperature as well as the heating rate; e.g., −30-250-10 means "from −30° C. to 250° C., at 10° C./min". The following table summarizes the abbreviations used in each image for pan configurations:

Modulated Differential Scanning calorimetry (mDSC) data were obtained on a TA Instruments Q2000 differential scanning calorimeter equipped with a refrigerated cooling system (RCS). Temperature calibration was performed using NIST-traceable indium metal. The sample was placed into an aluminum DSC pan, and the weight was accurately recorded. The pan was covered with a lid perforated with a laser pinhole, and the lid was crimped. A weighed, crimped aluminum pan was placed on the reference side of the cell. Data were obtained using a modulation amplitude of ±0.8° C. and a 60 second period with an underlying heating rate of 2° C./minute from 30 to 250° C. The reported glass transition temperatures are obtained from the inflection point of the step change in the reversing heat flow versus temperature curve.

Thermogravimetric (TG) TG analyses were performed using a TA Instruments Q5000 IR thermogravimetric analyzer. Temperature calibration was performed using nickel and Alumel™. Each sample was placed in an aluminum pan. The sample was hermetically sealed, the lid pierced, then inserted into the TG furnace. The furnace was heated under nitrogen. The data acquisition parameters for each thermogram are displayed in the image in the Data section of this report. The method code on the thermogram is an abbreviation for the start and end temperature as well as the heating rate; e.g., 25-350-10 means "from 25° C. to 350° C., at 10° C./min".

Hot stage microscopy was performed using a Linkam hot stage (FTIR 600) mounted on a Leica DM LP microscope equipped with a SPOT Insight™ color digital camera. Temperature calibrations were performed using USP melting point standards. Samples were placed on a cover glass, and a second cover glass was placed on top of the sample. As the stage was heated, each sample was visually observed using crossed polarizers and a first order red compensator. Images were captured using SPOT software (v. 4.5.9).

This specification has been described with reference to embodiments of the invention. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

We claim:

1. An isolated crystalline Form II of Compound 1:

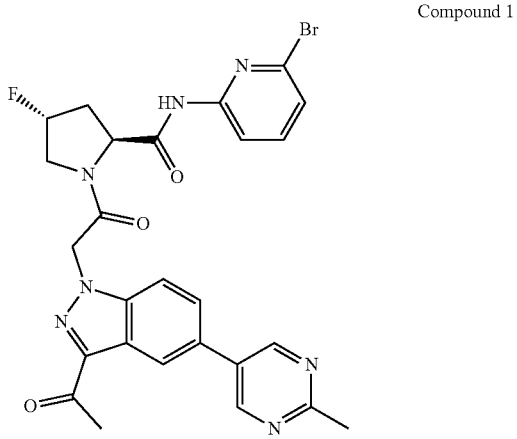 [SMILES: CC(=O)c1nn(CC(=O)N2C[C@H](F)C[C@H]2C(=O)Nc2cccc(Br)n2)c2ccc(-c3cnc(C)nc3)cc12]

Compound 1 characterized by a powder X-ray diffraction (PXRD) pattern comprising at least five 2theta values selected from 5.1±0.2°, 7.8±0.2°, 13.5±0.2°, 14.0±0.2°, 15.4±0.2°, 15.6±0.2°, 18.6±0.2°, 20.5±0.2°, 20.7±0.2°, and 23.4±0.2°.

2. The isolated crystalline Form II of claim 1, wherein the PXRD pattern comprises at least six 2theta values selected from 5.1±0.2°, 7.8±0.2°, 13.5±0.2°, 14.0±0.2°, 15.4±0.2°, 15.6±0.2°, 18.6±0.2°, 20.5±0.2°, 20.7±0.2°, and 23.4±0.2°.

3. The isolated crystalline Form II of claim 1, wherein the PXRD pattern comprises at least seven 2theta values selected from 5.1±0.2°, 7.8±0.2°, 13.5±0.2°, 14.0±0.2°, 15.4±0.2°, 15.6±0.2°, 18.6±0.2°, 20.5±0.2°, 20.7±0.2°, and 23.4±0.2°.

4. The isolated crystalline Form II of claim 1, wherein the PXRD pattern comprises at least eight 2theta values selected from 5.1±0.2°, 7.8±0.2°, 13.5±0.2°, 14.0±0.2°, 15.4±0.2°, 15.6±0.2°, 18.6±0.2°, 20.5±0.2°, 20.7±0.2°, and 23.4±0.2°.

5. The isolated crystalline Form II of claim 1, wherein the PXRD pattern comprises at least nine 2theta values selected from 5.1±0.2°, 7.8±0.2°, 13.5±0.2°, 14.0±0.2°, 15.4±0.2°, 15.6±0.2°, 18.6±0.2°, 20.5±0.2°, 20.7±0.2°, and 23.4±0.2°.

6. The isolated crystalline Form II of claim 1, wherein the PXRD pattern comprises 2theta values selected from 5.1±0.2°, 7.8±0.2°, 13.5±0.2°, 14.0±0.2°, 15.4±0.2°, 15.6±0.2°, 18.6±0.2°, 20.5±0.2°, 20.7±0.2°, and 23.4±0.2°.

7. The isolated crystalline Form II of claim 1, wherein the PXRD pattern comprises at least the 2theta value of 5.1±0.2°.

8. The isolated crystalline Form II of claim 1, wherein the PXRD pattern comprises at least the 2theta value of 14.0±0.2°.

9. The isolated crystalline Form II of claim 1, wherein the PXRD pattern comprises at least the 2theta value of 15.4±0.2°.

10. The isolated crystalline Form II of claim 1, having the 2theta values of FIG. 4C.

11. The isolated crystalline Form II of claim 1, characterized by a differential scanning calorimetry (DSC) endotherm from about 40° C. to about 125±20° C.

12. The isolated crystalline Form II of claim 1, characterized by a differential scanning calorimetry (DSC) endotherm of about 155° C.

13. A pharmaceutical composition comprising the isolated crystalline Form II of claim 1 in a pharmaceutically acceptable excipient for solid dosage delivery.

14. A method of inhibiting Complement Factor D in a subject in need thereof comprising administering to the subject in need thereof a therapeutically effective amount of the isolated crystalline Form II of claim 1.

15. The method of claim 14, wherein the subject is a human.

* * * * *